(12) United States Patent
Xiao

(10) Patent No.: US 7,510,867 B2
(45) Date of Patent: *Mar. 31, 2009

(54) DNA SEQUENCES ENCODING DYSTROPHIN MINIGENES AND METHODS OF USE THEREOF

(75) Inventor: Xiao Xiao, Wexford, PA (US)

(73) Assignee: Asklepios Biopharmaceutical Inc., Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/032,569

(22) Filed: Jan. 10, 2005

(65) Prior Publication Data

US 2006/0073586 A1 Apr. 6, 2006

Related U.S. Application Data

(63) Continuation of application No. 09/845,416, filed on Apr. 30, 2001, now Pat. No. 7,001,761.

(60) Provisional application No. 60/200,777, filed on Apr. 28, 2000.

(51) Int. Cl.
*C12N 15/00* (2006.01)
(52) U.S. Cl. .................................................. 435/320.1
(58) Field of Classification Search ............... 435/320.1
See application file for complete search history.

(56) References Cited

U.S. PATENT DOCUMENTS

| | | | |
|---|---|---|---|
| 4,868,116 A | 9/1989 | Morgan et al. | |
| 5,173,414 A | 12/1992 | Lebkowski et al. | |
| 5,399,346 A | 3/1995 | Anderson et al. | |
| 5,449,614 A | 9/1995 | Danos et al. | |
| 5,661,033 A | 8/1997 | Ho et al. | |
| 5,985,846 A | 11/1999 | Kochanek et al. | |
| 6,083,750 A | 7/2000 | Chamberlain et al. | |
| 6,207,455 B1 | 3/2001 | Chang et al. | |
| 6,410,300 B1 * | 6/2002 | Samulski et al. | 435/239 |
| 7,001,761 B2 * | 2/2006 | Xiao | 435/320.1 |
| 2002/0076754 A1 * | 6/2002 | Sun et al. | 435/69.1 |
| 2003/0216332 A1 | 11/2003 | Chamberlain et al. | |

FOREIGN PATENT DOCUMENTS

| | | |
|---|---|---|
| JP | 19999318467 A | 11/1999 |
| WO | WO 89/06286 | 7/1989 |
| WO | WO 97/22696 A1 | 8/1997 |
| WO | WO 98/09657 A2 | 3/1998 |
| WO | WO 01/29243 A1 | 4/2001 |
| WO | WO 02/29056 A2 | 4/2002 |

OTHER PUBLICATIONS

Clemens, P.R., et al., Recombinant truncated dystrophin minigenes: construction, expression, and adenoviral delivery, Human Gene Therapy, Nov. 1995, pp. 1477-1485, vol. 6, No. 11.
Dhermy, Didier, The spectrin super-family, Biol. Cell, 1991, pp. 249-254, vol. 71, No. 3.
Love, Donald R., et al., Dystrophin and dystrophin-related proteins: A review of protein and RNA studies , Neuromuscular Disorders, 1993, pp. 5-21, vol. 3, No. 1.
Turner, Gaynor, et al., Gene therapy of Duchenne muscular dystrophy, Dystrophin: Gene, Protein and Cell Biology; Brown, S. and Lucy, J., Eds., 1997, pp. 274-309, Publisher: Cambridge University Press, Published in: Cambridge, UK.
Roberts, et al., Determination of the Exon Structure of the Distal Portion of the Dystrophin Gene by Vectorette PCR. Genomics. 1992, vol. 13, pp. 942-950.
Rosenthal, et al., Two Human cDNA Molecules Coding for the Duchenne Muscular Dystrophy (DMD) Locus are Highly Homologus. Nucleic Acid Research. 1989, vol. 17, No. 13, p. 5391.
Haj-Ahmad, et al., Development of a Helper-Independent Human Adenovirus Vector in its use in the Transfer of the Herpes Simplex Virus Thymidine Kinase Gene. J. of Virology. Jan. 1986, vol. 57, No. 1, pp. 267-273.
Ragot, et al., Efficient Adenovirus-Mediated Transfer of a Human Minidystrophin Gene to Skeletal Muscle of mdx Mice. Nature. Feb. 18, 1993, vol. 361, pp. 647-650.
Howell, et al., High-Level Dystrophin Expression after Adeno-Virus Mediated Dystrophin Minigene Transfer to Skeletal Muscle of Dystrophic Dogs: Prolongation of Expression With Immunosuppression. Human Gene Therapy. Mar. 1998, vol. 9, pp. 629-634.
Inui, Koji et al., Gene Therapy in Duchenne Muscular Dystrophy, Brain Dev. 1996, vol. 18, pp. 357-361.
Hoffman, Eric P., Muscular Dystrophy: Identification and Use of Genes for Diagnostic and Therapuetics. Arch Patho Lab Med. Nov. 1999, vol. 123, pp. 1050-1052.
Hartigan-O'Connor, et al., Developments in Gene Therapy for Musclar Dystrophy. Microscopy Research and Technique. 2000, vol. 48, pp. 223-238.
Blake, DJ, et al., Coiled-coil Regions in the Carboxy-terminal Domains of Dystrophin and Related Proteins: Potentials for Protein-Protein Interactions. 1995, vol. 20, pp. 133-135.
Blake, Derek J., et al., Function and Genetics of Dystrophin and Dystrophin-Related Proteins in Muscle. Physiol Rev. 2002, vol. 82, pp. 291-329.
Pruchnic, et al., The Use of Adeno-Associated Virus to Circumvent the Maturation-Dependent Viral Transduction of Muscle Fibers. Human Gene Therapy. Mar. 1, 2000, vol. 11, pp. 521-536.

(Continued)

*Primary Examiner*—Brian Whiteman
(74) *Attorney, Agent, or Firm*—Steven J. Hultquist; Intellectual Property/Technology Law

(57) ABSTRACT

The present invention provides a series of novel dystrophin minigenes that retain the essential biological functions. The expression of the dystrophin minigenes may be controlled by a regulatory element along with a small polyadenylation signal. The entire gene expression cassettes may be readily packaged into a viral vector, preferably an AAV vector. The present invention further defines the minimal functional domains of dystrophin and provides ways to optimize and create new versions of dystrophin minigenes. Finally, the present invention provides a method of treatment for Duchenne muscular dystrophy (DMD) and Becker muscular dystrophy (BMD).

14 Claims, 8 Drawing Sheets

OTHER PUBLICATIONS

Greelish, et al., Stable Restoration of the Sarcoglycan Complex in Dystrophic Muscle Perfused with Histamine and a Recombinant Adeno-Associated Viral Vector. Nature Medicine. Apr. 1999, vol. 5, No. 4, pp. 439-443.
Song, et al., Sustained Secretion of Human Alpha-1-Antitrypsin from Murine Muscle Transduced with Adeno-Associated Virus Vectors. Proc. Natl. Acad. Sci. USA. Nov. 1998, vol. 95, pp. 14384-14388.
Kay, et al., Evidence for Gene Transfer and Expression of Factor IX in Haemophilia B Patients Treated with an AAV Vector. Nature Genetics. Mar. 2000, vol. 24, pp. 257-261.
Chen, et al., Low-Dose Vaccinia Virus-Mediated Cytokine Gene Therapy of Glioma. J. of Immunotherapy. 2001, pp. 46-57.
Bledsoe, et al., Cytokine Production in Motor Neurons by Polivirus Replicon Vector Gene Therapy. Nature Biotechnology. Sep. 18, 2000, vol. 18, pp. 964-969.
Wahlfors, et al., Evaluation of Recombinant Alphavirus as Vectors in Gene Therapy. Gene Therapy. 2000, vol. 7, pp. 472-480.
Romano, et al., Latest Developments in Gene Transfer Technology: Achievements, Perspectives, and Controversies over Therapeutic Applications. Stem Cells. 2000, vol. 18, pp. 19-39.
Lee, et al., Lipidic Vector Systems for Gene Transfer. Critical Reviews in Therapeutic Drug Carrier Systems. 1997, vol. 14, No. 2, pp. 173-206.
Zhang, et al., Long-Term Expression of Human Alpha 1-Antitrypsin Gene in Mouse Liver Achieved by Intravenous Administration of Plasmid DNA Using a Hydrodynamics-Based Procedure. Gene Therapy. 2000, vol. 7, pp. 1344-1349.
Yamashita, et al., Electroporation-Mediated Interleukin-12 Gene Therapy for Hepatocellular Carcinoma In the Mice Model. Cancer Research. Feb. 1, 2001, vol. 61, pp. 1005-1013.
Acsadi, et al., Human Dystrophin Expression in mdx Mice After Intramuscular Injection of DNA Constructs. Nature. 1991, vol. 352, pp. 815-818.
Rando, et al., Rescue of Dystrophin Expression in mdx Mouse Muscle by RNA/DNA Oligonucleotides. Proc. Natl. Acad. Sci. USA. May 9, 2000, vol. 97, No. 10, pp. 5363-5368.
Curiel, et al., Strategies to Adapt Adenoviral Vectors for Targeted Delivery. Annals New York Acad. Sci. 1999, vol. 886, pp. 158-171.
Greenberg, et al., Exogenous Dp71 Restores the Levels of Dystrophin Associated Proteins but Does Not Alleviate Muscle Damage in mdx Mice. Nature Genetics. Dec. 1994, vol. 8, pp. 340-344.
Yuasa, et al., Effective Restoration of Dystrophin-Associated Proteins in Vivo by Adenovirus-Mediated Transfer of Truncated Dystrophin cDNAs. Feb. 1998, vol. 425, pp. 329-336.
Yamamoto, et al., Immune Response to Adenovirus-Delivered Antigens Upregulates Utrophin and Results in Mitigation of Muscle Pathology in mdx Mice. Human Gene Therapy. Mar. 20, 2000, vol. 11, pp. 669-680.
Wu, et al., Mutational Analysis of the Adeno-Associated Virus Type 2(AAVZ) Capsid Gene and Construction of AAV2 Vectors with Altered Tropsim. J. of Virology, Sep. 2000, vol. 74, No. 18, pp. 8635-8647.
Girod, et al., Genetic Capsid Modifications Allow Efficient Re-Targeting of Adeno-Associated Virus Type 2. Nature Medicine. Sep. 1999, vol. 5, No. 9, pp. 1052-1056.
Lebkowski, et al., Adeno-Associated Virus: a Vector System for Efficient Introduction and Integration of DNA into a Variety of Mammalian Cell Types. Molecular and Cellular Biology. Oct. 1988, vol. 8, No. 10, pp. 3988-3996.
Zhou, et al., Adeno-Associated Virus 2-Mediated High Efficiency Gene Transfer Into Immature and Mature Subsets of Hermatopoietic Progenitor Cells in Human Umbilical Cord Blood. J. Exp. Med. Jun. 1994, vol. 179, pp. 1867-1875.
England, et al., Very Mild Muscular Dystrophy Associated with the Deletion of 46% of Dystrophin. Nature. Jan. 11, 1990, vol. 343, pp. 180-182.
Li, et al., Synthetic Muscle Promoters: Activities Exceeding Naturally Occurring Regulatory Sequences. Nature Biotechnology. Mar. 1999, vol. 17, pp. 241-245.
Tinsley, et al., Primary Structure of Dystrophin-Related Protein. Nature. Dec. 10, 1992, vol. 360, pp. 591-593.

Tinsley, et al., Amelioration of the Phenotype of mdx Mice Using a Truncated Utrophin Transgene. Nov. 28, 1996, vol. 384, pp. 349-353.
Rafael, et al., Skeletal Muscle-Specific Expression of a Utrophin Transgene Rescues Utrophin-Dystrophin Deficient Mice. Nature Genetics. May 19, 1998, vol. 19, pp. 79-82.
Li, et al., rAAV Vector-mediated Sarcoglycan Gene Transfer in a Hamster Model for Limb Girdle Muscular Dystrophy. Gene Therapy. 1999, vol. 6, pp. 74-82.
Matsuda, et al., Visualization of Dystrophic Muscle Fibers in Mdx Mouse by Vital Staining with Evans Blue: Evidence of Apoptosis in Dystrophin-Deficient Muscle. J. Biochem. 1995, vol. 118, pp. 959-964.
Shield, et al., E-Box Sites and a Proximal Regulatory Region of the Muscle Creatine Kinase Gene Differentially Regulate Expression in Diverse Skeletal Muscles and Cardiac Muscle of Transgenic Mice. Molecular and Cellular Biology. Sep. 1996, vol. 16, No. 9, pp. 5058-5068.
Xiao, et al., Production of High-Titer Recombinant Adeno-Associated Virus Vectors in the Absence of Helper Adenovirus. J. of Virology. Mar. 1998, vol. 72, No. 3, pp. 2224-2232.
Chapter 12 Vectors for Gene Therapy, by Snyder, et al. in Current Protocols in Human Genetics, eds. Dracopoli, et al. [Copyright 1996 John Wiley & Sons, Inc.], pp. 12.0.1-12.1.23.
Martin, et al., Regeneration of Dystrophic Muscle Following Multiple Injections of Bupivacaine. Muscle & Nerve. Jun. 1988, vol. 11, pp. 588-596.
Muzyczka, N. Use of Adeno-Associated Virus as a General Transduction Vector for Mammalian Cells. Curr. Topics in Micro. and Immunol. 1992, vol. 158, pp. 97-129.
Deconinck, et al., Expression of Truncated Utrophin Leads to Major Functional Improvements in Dystrophin-Deficient Muscles of Mice. Nature Medicine. Nov. 1997, vol. 3, No. 11, pp. 1216-1221.
Schwarze, et al, In Vivo Protein Transduction: Delivery of a Biologically Active Protein Into the Mouse. Science. Sep. 3, 1999, vol. 285, pp. 1569-1572.
Kunkel, et al., Analysis of Deletions in DNA From Patients with Becker and Duchenne Muscular Dystrophy. Nature. Jul. 1986, vol. 322, No. 3, pp. 73-77.
Watkins, et al., Immunoelectron Microscopic Localization of Dystrophin in Myofibres. Nature. Jun. 1988, vol. 333 No. 30, pp. 863-866.
Koenig, et al., Detailed Analysis of the Repeat Domain of Dystrophin Reveals Four Potential Hinge Segments that May Confer Flexibility. J. BiologicalChemistry. Mar. 1990, vol. 265, No. 8, pp. 4560-4566.
Monaco, et al., An Explanation for the Phenotypic Differences Between Patients Bearing Partial Deletions of the DMD Locus. Genomics2. 1988, pp. 90-95.
Hoffman, et al. Characterization of Dystrophin in Muscle-Biopsy Specimens from Patients with Duchenne's or Becker's Muscular Dystrophy. New England J. of Medicine. May 26, 1988, vol. 318, No. 21, pp. 1363-1368.
Bulfield, et al., X Chromosome-Linked Muscular Dystrophy (mdx) in the Mouse. Proc. Natl. Acad. Sci. USA. Feb. 1984, vol. 81, pp. 1189-1192.
Gussoni, et al., The Fate of Individual Myoblasts After Transplantation into Muscles of DMD Patients. Nature Medicine. Sep. 1997, vol. 3, No. 9, pp. 970-977.
Wang, et al., Adeno-Associated Virus Vector Carrying Human Minidystrophin Genes Effectively Ameliorates Muscular Dystrophy in mdx Mouse Model. Dec. 2000, vol. 97, No. 25, pp. 13714-13719.
Gieseler, et al., In Vitro Interactions of Caenorhabditis elegans Dystrophin with Dystrobrevin and Syntrophin. FEBS Letters. 1999, vol. 461, pp. 59-62.
Wang, et al., Efficient Functional Correction of Muscular Dystrophy in mdx Mice by AAV Vectors Carrying Novel Human Mini-Dystrophin Genes. Molecular Therapy. May 2000, vol. 1, No. 5.
Harper, et al., Modular Flexibility of Dystrophin: Implications for Gene Therapy of Duchenne Musclar Dystrophy. Nature Medicine. Mar. 2002, vol. 8, No. 3, pp. 253-261.
Cox, et al., Dp71 Can Restore the Dystrophin-associated Gylcoprotein Complex in Muscle but Fails to Prevent Dystrophy. Nature Genetics. Dec. 1994, vol. 8.

Fujimore, Keita, et al., Interleukin 6 Induces Overexpression of the Sarcolemmal Utrophin in Neonatal mdx Skeletal Muscle. Human Gene Therapy. Mar. 1, 2002, vol. 13, pp. 509-518.

Fabb, et al., Adeno-associated Virus Vector Gene Transfer and Sarcolemmal Expression of a 144 kDa Micro-dystrophin . . . Human Molecular Genetics. 2002, vol. 11, No. 7, pp. 733-741.

Harper, et al., Modular Flexibility of Dystrophin: Implications for Gene Therapy of Duchenne Muscular Dystrophy. Nature Medicine. Mar. 2002, vol. 8, No. 3, pp. 253-261.

Fink, et al., Gene Transfer to Neurons Using Herpes Simplex Virus-Based Vectors. Annu. Rev. Neuroscience. 1986, pp. 265-287.

Naldini, et al., In Vivo Gene Delivery and Stable Transduction of Nondividing Cells by a Lentiviral Vector. Science. Apr. 12, 1996, vol. 272, pp. 263-267.

Flotte, et al., Gene Expression from Adeno-Associated Virus Vectors in Airway Epithelial Cells. Am J. Respiratory Cell and Molecular Biology. 1992, vol. 7, pp. 349-356.

Samulski, et al., Helper-Free Stocks of Recombinant Adeno-Associated Viruses: Normal Integration Does Not Require Viral Gene Expression. J. of Virology. Sep. 1989, vol. 63, No. 9, pp. 3822-3828.

Xiao, et al., Efficient Long-Term Gene Transfer into Muscle Tissue of Immunocompetent Mice by Adeno-Associated Virus Vector. J. Virology. Nov. 1996, vol. 70, No. 11, pp. 8098-8108.

Kessler, et al., Gene Delivery to Skeletal Muscle Results in Sustained Expression and Systemic Delivery of a Therapeutic Protein. Proc. Natl. Acad. Sci. USA. Nov. 1996, vol. 93, pp. 14082-14087.

Xiao, et al., Adeno-Associated Virus as a Vector for Liver-Directed Gene Therapy. J. of Virology. Dec. 1998, vol. 72, No. 12, pp. 10222-10226.

Koenig, et al., Complete Cloning of the Duchenne Muscular Dystrophy (DMD) cDNA and Preliminary Genomic Organization of the DMD Gene in Normal and Affected Individuals. Cell. Jul. 31, 1997, vol. 50, pp. 509-517.

Huang, et al., Structure of a WW Domain Containing Fragment of Dystrophin in Complex with B-Dystroglycan. Nature Structural Biology. Aug. 2000, vol. 7, No. 8, pp. 634-638.

Kahana, et al., Conformation and Phasing of Dystrophin Structural Repeats. J. Mol. Biol. 1994, vol. 235, pp. 1271-1277.

Kahana, et al., Physical Properties of Dystrophin Rod Domain. Cell Motility and the Cytoskeleton. 1997, vol. 36, pp. 246-252.

Moores, et al., Structure of the Utrophin Actin-Binding Domain Bond to F-Actin Reveals Binding by an Induced Fit Mechanism. J. Mol. Biol. 2000, vol. 297, pp. 465-480.

Norwood, et al., The Structure of the N-Terminal Actin-binding Domain of Human Dystrophin and How Mutations in this Domain May Cause Duchenne or Becker Muscular Dystrophy. Research article, pp. 481-491.

Barton-Davis, et al., Aminoglycoside Antibiotics Restore Dystrophin Function to Skeletal Muscles of mdx Mice. j. Clinical Investigation. Aug. 1999, vol. 104, No. 4, pp. 375-381.

Chiu, et al., Optimizing Energy Potentials for Success in Protein Tertiary Structure Prediction. Folding and Design. May 1998, vol. 3, pp. 223-228.

Ngo, et al., Computational Complexity, Protein Structure Prediction and the Levinthal Paradox. The Protein Folding Problem and Tertiary Structure Prediction. 1994, pp. 433 and 492-495.

Koenig, et al., The Complete Sequence of Dystrophin Predicts a Rod-Shaped Cytoskeletal Protein. Cell. Apr. 1998, vol. 35, pp. 219-228.

Anderson, W.F., Human Gene Therapy. Apr. 1998, vol. 392, pp. 25-30.

Keep, Nicholas H., et al., Crystal structure of the actin-binding region of utrophin reveals a head-to-tail dimer, Structure, Dec. 15, 1999, pp. 1539-1546, vol. 7, No. 12.

Keep, Nicholas H., et al., The 2.0 A structure of the second calponin homology domain from the actin-binding region of the dystrophin homologue utr, J. Mol. Biol., Jan. 22, 1999, pp. 1257-1264, vol. 285, No. 3.

Miller, A. Dusty, Progress toward human gene therapy, Blood, Jul. 15, 1990, pp. 271-278, vol. 76, No. 2.

* cited by examiner

DNA SEQUENCES ENCODING DYSTROPHIN MINIGENES AND METHODS OF USE THEREOF

CROSS-REFERENCE TO RELATED APPLICATION

This is a continuation of U.S. patent application Ser. No. 09/845,416 filed Apr. 30, 2001 and issued Feb. 21, 2006 as U.S. Pat. No. 7,001,761, claiming the benefit of U.S. Provisional Patent Application No. 60/200,777 filed Apr. 28, 2000. The disclosures of U.S. patent application Ser. No. 09/845,416 and U.S. Provisional Patent Application No. 60/200,777 are hereby incorporated by reference herein in their respective entireties.

TECHNICAL FIELD

The present invention relates to novel dystrophin minigenes that retain the essential biological functions of a full length dystrophin gene, and methods of treatment for Duchenne muscular dystrophy (DMD) and Becker muscular dystrophy (BMD) in a mammalian subject using the dystrophin minigenes.

BACKGROUND OF INVENTION

Duchenne muscular dystrophy (DMD) is an X-linked genetic muscle disease affecting 1 of every 3,500 newborn males (Kunkel et al. Nature (London) 322,73-77 [1986]). The progressive muscle degeneration and weakness usually confine the patients to wheelchairs by their early teens, and lead to death by their early twenties. DMD is caused by recessive mutations in the dystrophin gene, the largest gene known to date, which spans nearly 3 million base-pairs on the X-chromosome with 79 exons, a coding sequence of about 11 kb, and a high rate of de novo mutations. (Koenig et al. Cell 50, 509-517 [1987]).

Dystrophin is an enormous rod-like protein of 3,685 amino acids (aa) localized beneath the inner surface of muscle cell membrane (Watkins, S. C. et al. Nature 333, 863-866 [1988]). It functions through four major structural domains: a N-terminal domain (1-756 aa), a central rod domain (757-3122 aa), a cysteine rich (CR) domain (3123-3409aa), and a distal C-terminal domain (3410-3685 aa). The N-terminal domain binds to the F-actin of cytoskeletal structures, while the CR domain along with the distal C-terminal domain anchors to the cell membrane via dystrophin-associated protein (DAP) complexes, thus, dystrophin crosslinks and stabilizes the muscle cell membrane and cytoskeleton. The central rod domain contains 24 triple-helix rod repeats (R1-R24) and 4 hinges (H1-H4). Each repeat is approximately 109 aa long. (Koenig et al. J Biol Chem 265, 4560-4566 [1990]). The central rod domain presumably functions as a "shock absorber" during muscle contraction. Dystrophin crosslinks and stabilizes the muscle cell membrane and cytoskeleton. The absence of a functional dystrophin results in the loss of DAP complexes and causes instability of myofiber plasma membrane. These deficiencies in turn lead to chronic muscle damage and degenerative pathology.

The vast majority of DMD mutations disrupt the dystrophin mRNA reading frame or introduce a stop codon that prematurely ends protein translation (Monaco et al. Genomics 2, 90-95 [1988]). In the less severe allelic form of the disease, Becker muscular dystrophy (BMD), dystrophin gene mutations are usually such that the mRNA reading frame is maintained. Thus in BMD patients, some functional gene product, albeit of reduced quantity and/or quality, is synthesized that contributes to the milder phenotype (Hoffman et al. N. Engl. J Med. 318, 1363-1368 [1988]).

The mdx mouse (Bulfield et al. Proc. Natl. Acad. Sci. USA 81, 1189-1192 [1984]) is an animal model of DMD. The genetic lesion in the mdx dystrophin gene is a nonsense mutation at base 3185 of the mRNA that causes premature termination of translation within exon 23. This nonsense mutation precludes synthesis of a functional protein.

Due to the lack of effective treatment for DMD, novel genetic approaches including cell therapy and gene therapy have been actively explored. However, clinical trials of myoblast transplantation have met with little success owing to the poor survival of the transplanted cells (Gussoni et al., Nature Med 3, 970-977 [1997]). It was recently reported that gentamicin treatment in mdx mice led to the suppression of the premature stop codon in the dystrophin gene, and the subsequent expression and localization of functional dystrophin to the cell membrane (Barton-Davis et al. J Clin Invest. 104, 375-381 [1999]). This treatment could prove effective in up to 15% of patient with DMD.

Somatic gene transfer offers a new approach to replace the defective dystrophin gene. A preferred approach for introducing genetic material encoding a gene product into an organ or a tissue is by use of a viral vector. In this situation, the genetic material encoding the gene product is inserted into the viral genome (or a partial viral genome). The regulatory elements directing the expression of the gene product can be included with the genetic material inserted into the viral genome (i.e., linked to the gene inserted into the viral genome) or can be provided by the viral genome itself, for example, a retrovirus long terminal repeat (LTR) or an adeno-associated virus (AAV) inverted terminal repeat (ITR). Infection of cells with a viral vector has the advantage that molecules encoded within the viral vector, e.g., by a cDNA contained in the viral vector, are expressed efficiently in cells which have taken up viral vector nucleic acid and viral vector systems can be used in vivo. Different viral vectors are described separately in the subsections below.

1. Adenovirus vectors: The genome of an adenovirus can be manipulated such that it encodes and expresses a gene product of interest but is inactivated in terms of its ability to replicate in a normal lytic viral life cycle (Curiel, Ann N Y Acad Sci 886, 158-71 [1999]). Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium, endothelial cells and muscle cells. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Haj-Ahmand et al. J. Virol. 57, 267-273 [1986]). Most replication-defective adenoviral vectors currently in use are deleted for all or parts of the viral E1 and E3 genes but retain as much as 80% of the adenoviral genetic material. Adenoviral vectors deleted for all viral coding regions are also described by Kochanek et al. and Chamberlain et al. (U.S. Pat. Nos. 5,985,846 and 6,083,750).

Adenovirus vectors have been successfully tested in dystrophic animal models (Ragot et al. Nature 361, 647-50 [1993]; Howell et al. Hum Gene Ther 9, 629-34 [1998]). Nonetheless, the immunogenicity and inefficiency of infecting mature muscle cells remain major hurdles to overcome before the adenovirus vectors can be safely used in humans.

2. Herpes simplex virus (HSV) vectors: The main feature of an HSV vector is that it has very large packaging capacity, is usually replication defective and does not integrate into the host genome. HSV infects cells of the nervous system (Fink et al. Annu Rev Neurosci 19, 265-287, [1996]). The virus contains more than 80 genes, one of which (IE3) can be replaced to create the vector. The generation of HSV vectors with deletions in many of the immediate early gene products has resulted in vectors with reduced toxicity and antigenicity, as well as prolonged expression in vivo. However, these modifications also result in a lower virus yield. Construction of HSV vectors is described in U.S. Pat. No. 5,661,033.

3. Retrovirus vectors: Defective retroviruses are well characterized for use in gene transfer for gene therapy purposes (Miller A D Blood 76, 271-278 [1990]. The members of the family Retroviridae are characterized by the presence of reverse transcriptase in their virions. There are several genera included within this family, including Cisternavirus A, Oncovirus A, Oncovirus B, Oncovirus C, Oncovirus D, Lentivirus, and Spumavirus.

A recombinant retrovirus can be constructed having a nucleic acid encoding a gene product of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in "Current Protocols in Molecular Biology, Ausubel, F. M. et al. (eds.) Greene Publishing Associates, (1989), Sections 9.10-9.14" and other standard laboratory manuals. Examples of suitable retroviruses include pLJ, pZIP, pWE and pEM which are well known to those skilled in the art. Examples of suitable packaging virus cell lines include .psi-.Crip, .psi.Cre, .psi.2 and .psi.Am.

Retroviruses have been used to introduce a variety of genes into many different cell types, including epithelial cells, endothelial cells, lymphocytes, myoblasts, hepatocytes, hematopoietic stem cells, in vitro, and/or in vivo (U.S. Pat. Nos. 4,868,116; 5,449,614 and 6,207,455). Retroviral vectors require target cell division in order to be integrated into the host genome to stably introduce nucleic acid into the cell. Thus, it may be necessary to stimulate replication of the target cell. Successful transductions of hematopoietic stem or progenitor cells with retroviral vectors in an ex vivo setting have been reported. However, Recombinant retroviral vectors can only accommodate about 8 kb to 10 kb of foreign DNA. This packaging capacity also limits its use in the genetic treatment of DMD.

4. Lentivirus vectors. Lentiviruses also belong to the retrovirus family, but they can infect both dividing and non-dividing cells. The best-known lentivirus is the human immunodeficiency virus (HIV), which has been disabled and developed as a vector for in vivo gene delivery. Like the simple retroviruses, HIV has three genes termed gag, pol and env, it also carries genes for six accessory proteins termed tat, rev, vpr, vpu, nef and vif. Using the retrovirus vectors as a model, lentiviral vectors have been made, with the transgene enclosed between the LTRs and a packaging sequence (Naldni et al. Science 272, 263-267 [1996]). Some of the accessory proteins can be eliminated without affecting production of the vector or efficiency of infection.

When lentiviral vectors are injected into rodent brain, liver, muscle, eye or pancreatic islet cells, they give sustained expression for over six months. Little is known about the possible immune problems associated with lentiviral vectors. Furthermore, there seems to be no potent antibody response. A major concern about lentiviral vector is its safety in human applications. However, recent development in producing the third generation lentiviral vectors with more deletion in viral genes and improved safety may allow for the general application of lentiviral vectors to in vivo gene therapy.

5. Adeno-associated viruses (AAV) vectors: AAV is a naturally occurring defective virus that requires another virus, such as an adenovirus or a herpes virus, as a helper virus for efficient replication and a productive life cycle (Muzyczka et al. Curr. Topics in Micro. and Immunol. 158, 97-129 [1992]). AAV vector is the only viral vector system that is based on a non-pathogenic and replication defective virus. It is also one of the few viruses that may integrate its DNA into non-dividing cells, and exhibits a high frequency of stable integration (Flotte et al. Am. J Respir. Cell. Mol. Biol. 7, 349-356 [1992]; Samulski et al. J. Virol. 63, 3822-3828 [1989]). Vectors containing as little as 300 base pairs of AAV DNA can be packaged.

AAV vectors have been successfully used to establish efficient and long-term gene expression in vivo in a variety of tissues without significant immune response or toxicity (Xiao et al. J. Virol. 70, 8098-108 [1996]; Kessler et al. Proc Natl Acad Sci USA 93, 14082-7 [1996]; Xiao et al. J Virol 72, 10222-6 [1998]). Unlike other viral vectors, AAV readily bypasses extracellular barriers due to its small viral particle size (20 nm) that facilitates efficient transduction of muscle myofibers of various maturity (Pruchnic et al. Hum Gene Ther 11, 521-36 [2000]). AAV can also be delivered into a large number of muscle groups via the blood vessels (Greelish et al. Nat. Med. 5, 439-443 [1999]) The unparalleled efficiency and safety have led to an increasing interest in AAV-mediated gene therapy for genetic muscle disorders, as well as for metabolic diseases. However, a major obstacle for AAV vectors is the limited packaging size that only allows for genes smaller than 4.7 kb (Song et al. Proc Natl Acad Sci USA 95, 14384-8 [1998]; Kay et al. Nat Genet 24, 257-261 [2000]), therefore precludes such large gene as dystrophin with a cDNA of 14 kb.

Other viral vector systems that may have application in the subject invention have been derived from vaccinia virus (Chen et al. J Immunother 24, 46-57 [2001]), and several RNA viruses. The plus-strand RNA viridae, such as polio (Bledsoe et al. Nat Biotechnol. 18, 964-9 [2000]), hepatitis A (Romano G. Stem Cells; 18, 19-39 [2000]), and sindbis virus (Wahlfors et al. Gene Ther 7, 472-80 [2000]) are being developed for high-level gene expression, following either viral infection or delivery of nucleic acids using a nonviral system. These viruses express a replicase protein that can specifically replicate the viral RNA. By inserting a transgene in place of the viral capsid gene(s), it is possible to generate a chimeric RNA that replicates autonomously in the cell and expresses a high level of protein from the plus-coding strand of RNA. These viral vectors are well suited for immunization strategies in which high, transient gene expression is needed to induce an immune response to the transduced cells.

In addition to the viral gene transfer vectors, powerful non-viral gene transfer vectors have also become available for clinical application in the past several years (Ropert et al. Braz J Med Biol Res. 32,163-9 [1999]; Lee R J et al. Crit Rev Ther Drug Carrier Syst 14, 173-206 [1997]). These vectors rely on normal mechanisms used by mammalian cells for the uptake and intracellular transport of macromolecules to deliver genetic materials into cells. These vectors include cationic and other liposomes, DNA-viral conjugates, RNA/DNA oligonucleotides and, surprisingly, naked DNA molecules. Physical procedures, such as hydrodynamics-based and electroporation-based procedures have been used to improve gene transfer efficiency of some non-viral vectors (Zhang G. et al. Gene Ther 7, 1344-9 [2000]; Yamashita et al. Cancer Res. 61, 1005-12 [2001]). Recently, it was also reported that intraperitoneal injection of a .beta.-galactosidase fused to the protein transduction domain from the human immunodeficiency virus TAT protein resulted in delivery of the fusion protein to all tissues in mice (Schwarze et al. Science, 3, 1569-1572 [1999])

Somatic gene transfer using non-viral vectors carrying dystrophin gene have been attempted [Acsadi et al. Nature 352, 815-818 [1991]; Rando et al. Proc. Natl. Acad. Sci USA 97, 5363-5368 [2000]). Transgene expression was achieved with only very limited efficiency.

Previous attempts to generate dystrophin minigenes that were shorter than ½ of the full-length dystrophin failed to preserve the essential protective functions. Cox et al. and Greenberg et al. reported that expression of Dp 71, a 71 kD non-muscle product of the dystrophin gene that consists of the cysteine-rich and C-terminal domains of dystrophin (exon 63-79), in the skeletal muscle of dystrophin deficient mar mice restored normal levels dystrophin associated proteins (DAPs). However, expression of Dp71 failed to alleviate symptoms of muscle degeneration [Cox et al. Nature Genet 8, 333-339 [1994]; Greenburg et al. Nature Genet 8, 340-344 [1994]). Similarly, Yuasa et al (Yuasa et al. FEBS Lett 425, 329-336 [1998]; Yamamoto et al. Hum Gene Ther 11, 669-80 [2000]) demonstrated that expression of dystrophin minigenes with both intact N- and C-terminal domains and 1 to 3 central rod repeats in mouse skeletal muscle was sufficient to restore DAP complexes but insufficient to restore myofiber morphology and to prevent dystrophic pathology.

SUMMARY OF THE INVENTION

The present invention provides dystrophin minigenes that are significantly reduced in size without compromising essential functions in protecting muscles from dystrophic phenotypes. The present invention also provides viral vectors carrying the dystrophin minigenes that are capable of mediating efficient and stable correction of both biochemical and physiological defects in a mammalian subject. Furthermore, the present invention provides a method that is more convenient and less time-consuming to discern the dystrophin functional domains in vivo and to optimize the minigenes for DMD gene therapy. Finally, the present invention provides a method for treatment of muscular dystrophy.

DETAILED DESCRIPTION AND PREFERRED EMBODIMENTS OF THE INVENTION

Figure 1:
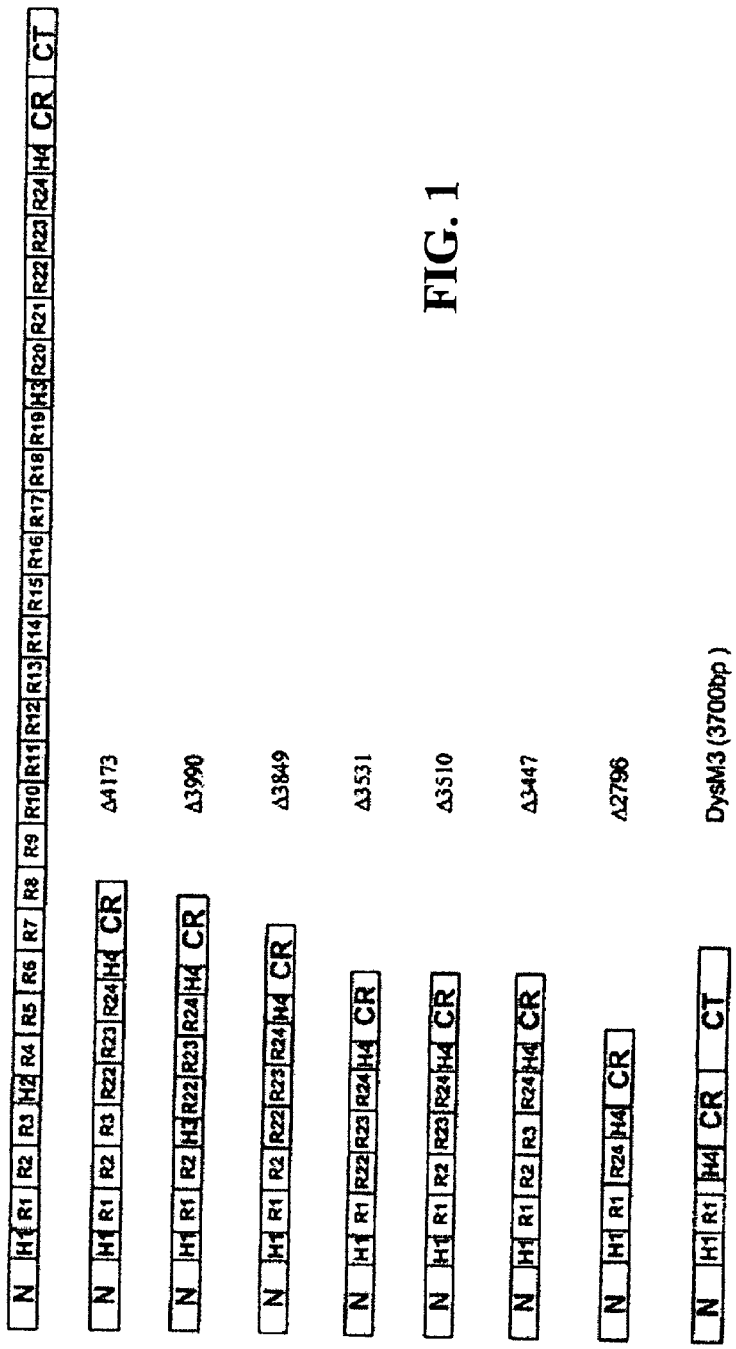
FIG. 1 shows the construction of highly truncated dystrophin minigenes and AAV vectors carrying the dystrophin minigene.
Figure 1:
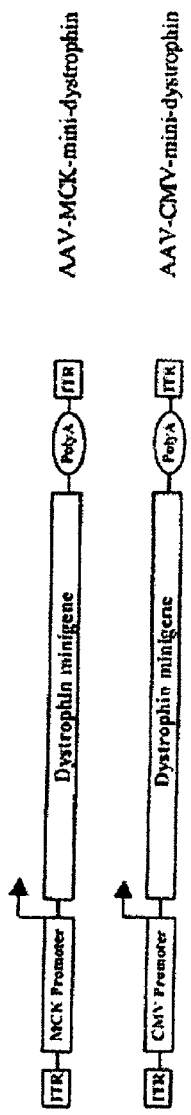

The practice of the present invention will employ, unless other wise indicated, conventional methods of histology, virology, microbiology, immunology, and molecular biology within the skill of the art. Such techniques are explained fully in the literature. All publications, patents and patent applications cited herein, whether supra or infra, are hereby incorporated by reference in their entirety.

As used in this specification and the appended claims, the singular forms "a," "an" and "the" include plural references unless the content clearly dictates other wise.

A. Definitions

In describing the present invention, the following terms will be employed, and are intended to be defined as indicated below.

"Gene transfer" or "gene delivery" refers to methods or systems for reliably introducing a particular nucleotide sequence (e.g., DNA) into targeted cells. The introduced nucleotide sequences may persist in vivo in episomal forms or integrate into the genome of the target cells. Gene transfer provides a unique approach for the treatment of acquired and inherited diseases, and a number of systems have been developed in the art for gene transfer into mammalian cells. See, e.g., U.S. Pat. No. 5,399,346.

As used herein, the term "effective amount" refers to a level of infection which brings about at least partially a desired therapeutic or prophylactic effect in an organ or tissue infected by the method of the present invention. The infection with an effective amount of the vector carrying genetic material of interest can then result in the modification of the cellular activities, e.g., a change in phenotype, in an organ or a tissue that has been infected by the method of the present invention. In a preferred embodiment, the infection with an effective amount of the vector carrying genetic material of interest results in modulation of cellular activity in a significant number of cells of an infected organ or a tissue.

A gene transfer "vector" refers to any agent, such as a plasmid, phage, transposon, cosmid, chromosome, liposome, DNA-viral conjugates, RNA/DNA oligonucleotides, virus, bacteria, etc., which is capable of transferring gene sequences into cells. Thus, the term includes cloning and expression vehicles, as well as viral and non-viral vectors. A vector may be targeted to specific cells by linking a target molecule to the vector. A targeting molecule is any agent that is specific for a cell or tissue type of interest, including for example, a ligand, antibody, sugar, receptor, or other binding molecule. The invention is also intended to include such other forms of vectors which serve equivalent functions and which become known in the art subsequently hereto.

An "AAV vector" refers to vectors derived from an adeno-associated virus serotype, including human AAV-1, AAV-2, AAV-3, AAV-4, AAV-5, AAV-6, avian AAV, ovian AAV, etc., and to vectors derived from more than one AAV serotype (hybrid AAV vectors). For example, a hybrid AAV vector may contain DNA sequences derived from both AAV-1 and AAV-2. An AAV vectors can have one or more of the AAV wild-type genes deleted in whole or part, preferably the rep and/or cap genes, but retain functional flanking ITR sequences. AAV vectors can be constructed using recombinant techniques that are known in the art to include one or more heterologous nucleotide sequences flanked on both ends (5' and 3') with functional AAV ITRs. In the practice of the invention, an AAV vector can include at least one AAV ITR and a suitable promoter sequence positioned upstream of the heterologous nucleotide sequence and at least one AAV ITR positioned downstream of the heterologous sequence.

A "recombinant AAV vector plasmid" refers to one type of recombinant AAV vector wherein the vector comprises a plasmid. As with AAV vectors in general, 5' and 3' ITRs flank the selected heterologous nucleotide sequence. AAV vectors can also include transcription sequences such as polyadenylation sites, as well as selectable markers or reporter genes, enhancer sequences, and other control elements which allow for the induction of transcription. Such control elements are described more fully below. In addition, an "AAV vector" can be stably introduced into a cell line or cell lines for the purpose of viral particle production. Such a cell line is usually termed as AAV packaging cell line.

As used herein, the term "recombinant AAV", "recombinant AAV particle" or "recombinant AAV virion" is defined as an infectious, replication-defective virus composed of an AAV protein shell encapsidating (i.e., surrounding with a protein coat) a heterologous nucleotide sequence, which in turn is flanked 5' and 3' by AAV ITRs. In this regard, single-stranded AAV nucleic acid molecules (either the sense/coding strand or the antisense/anticoding strand as those terms are generally defined) can be packaged into an AAV virion; both the sense and the antisense strands are equally infectious. When the recombinant AAV DNA is equal to or smaller than 50% of the full length viral genome (about 5,000 nucleotides), it can also be packaged as double-stranded hairpin-like DNA into AAV virion. Such virion is also fully infectious.

The term "recombinant AAV particle" or "recombinant AAV virion" also refers to a hybrid AAV particle in which the AAV protein shell and the encapsulated nucleotide sequence may be derived from AAVs of different serotype. For example, a hybrid AAV particle may contain AAV-1 capsid proteins and AAV-2 ITRs, or vice versa. It is also possible to create hybrid AAV capsid proteins using coding sequences from two or more AAV capsid genes. In addition, the capsid protein of a recombinant AAV may be manipulated by mutation, deletion, and/or insertion of amino acid sequence in order to modify the tropism of the recombinant AAV (Wu et al. J. Virol 74, 8635-47 [2000]; Girod et al. Nat Med 5, 1052-1056 [1999]).

A number of techniques for constructing recombinant AAV are known in the art. See, e.g., U.S. Pat. No. 5,173,414, Lebkowski et al. Mol Cell Biol 8, 3988-3996 [1988]; Carter B J, Current Opinion in Biotechnology 3, 533-539 [1992]; Muzyczka N, cited supra; and Zhou et al. J. Exp. Med. 179, 1867-1875 [1994]; Xiao et al. J. Virol. 72, 2224-32 [1998].

The term "expression control element" or "regulatory element" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. The term "promoter" is used herein in its ordinary sense to refer to a DNA regulatory sequence that are sufficient for RNA polymerase recognition, binding and transcription initiation. Additionally, a promoter includes sequences that modulate the recognition, binding and transcription initiation activity of RNA polymerase. Such sequences may be cis acting or may be responsive to trans acting factors. Depending upon the nature of the regulation, promoters may be constitutive or regulated. Examples of promoters are SP6, T4, T7,SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, muscle creatine kinase (MCK) promoter, myosin promoter, .alpha.-actin promoter and the like. Alternatively, the modified versions of the above promoters and even the synthetic muscle promoters (Li et al. Nat Biotechnol 17, 241-245, [1999]) may be included. Finally, the promoter may be an endogenous AAV promoter or AAV inverted terminal repeat (ITR).

The term "transduction" denotes the delivery of a DNA molecule to a recipient cell either in vivo or in vitro, via a replication-defective viral vector, such as via a recombinant AAV virion.

The term "muscle cell" or "tissue" refers to a cell or group of cells derived from muscle, including but not limited to cells and tissue derived from skeletal muscle; cardiac muscle, smooth muscle, e.g., from the digestive tract, urinary bladder and blood vessels. The term captures muscle cells both in vitro and in vivo. Thus, for example, an isolated cardiomyocyte would constitute a "muscle cell" for purposes of the present invention, as would a muscle cell as it exists in muscle tissue present in a subject in vivo. The term also encompasses both differentiated and nondifferentiated muscle cells, such as myocytes, myotubes, myoblasts, cardiomyocytes and cardiomyoblasts, and progenitor cells, for example, the muscle derived stem cells or the bone marrow derived stem cells that can become muscle cells after differentiation "Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "dystrophin minigene" refers to the novel dystrophin constructs created by extensive deletions in the central rod domain plus extensive deletion in the C-terminal domain of the human dystrophin cDNA. In addition, the dystrophin minigenes may contain a modified N-terminal domain in which DNA sequences surrounding the original protein translation initiation codon ATG are modified. The modified sequences enhance the mini-dystrophin protein synthesis. Alternatively, the dystrophin minigene may be a hybrid gene in which some of the domains are substituted with homologous domains from utrophin or spectrin genes (Tinsley et al, Nature 360, 591-593 [1992]; Koenig et al. Cell 53, 219-216 [1988]). In particular, utrophin is highly homologous to dystrophin in both structure and functions, so that their major domains should be interchangeable (Tinsley et al, Nature. 384, 349-353 [1996]; Deconinck et al, Nat Med. 3, 1216-21 [1997]; Rafael et al Nat Genet. 19, 79-82 [1998];). For example, the N-terminal and/or the C-terminal domains of dystrophin may be substituted with the utrophin counterparts in the dystrophin minigenes. Similarly, the central rod domain may consist of rod repeats from utrophin or spectrin genes. The dystrophin minigenes are smaller than the 5 kb packaging limit of AAV viral vectors. Furthermore, it is also plausible to construct a minigene of utrophin in a similar fashion as of the dystrophin minigene described in this invention. Because some DMD patients completely lack the dystrophin protein, the dystrophin minigene product may be a neo-antigen. Substitution of dystrophin domains with those of utrophin may lower immune responses.

The term "mini-dystrophin" refers to the polypeptides encoded by the dystrophin minigenes. Most importantly, the mini-dystrophins harbor biological functions that can protect the muscle from dystrophic pathology and symptoms.

The symbol ".DELTA." (delta) is a prefix for the dystrophin minigenes that contain deletions as described above.

By "mammalian subject" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The term "expression cassette" refers to a construct of genetic material that contains coding sequences and enough regulatory information to direct proper transcription and translation of the coding sequences in a recipient cell.

B. Detailed Description of the Invention

To explore the feasibility of using viral vectors for DMD gene therapy, we have devised strategies to create novel dystrophin minigenes, which are small enough to be packaged into retrovirus or AAV vectors, and yet retain the essential functions needed for protecting muscle from the pathological symptoms. We have created minigenes in which up to 75% of the central rod domain (20 of the 24 rods; 2 of the 4 hinges), as well as nearly all the C-terminal domain (exons 71-78), are deleted (FIG. 1). These novel dystrophin minigenes, as small as only one third (⅓) of the 11 kb full-length dystrophin coding sequence, are significantly smaller than the 6.3 kb Becker-form mini-dystrophin gene (England et al. Nature 343, 180-2 [1990]) that was widely used in transgenic and gene therapy studies in mdx mice. The minigene comprises the N-terminus sequence of the dystrophin gene, the C-terminal cysteine-rich (CR) domain of the dystrophin gene, at least hinges H1 and H4 of dystrophin gene, and at least four rod repeats. The rod repeats may be chosen from the rod repeats of dystrophin, utrophin or spectrin genes, preferably from the 24 rod repeats of dystrophin gene, and most preferably from the group consisting of rod repeats R1, R2, R3, R22, R23 and R24 of dystrophin gene. The N-terminus of the dystryphin minigene may be modified to improve expression efficiency without affecting the functionality of the gene product. For example, the original sequence surrounding the translation initiation ATG codon of the dystrophin gene may be substituted by the Kozak sequence to increase the efficiency of protein synthesis. In one embodiment of the current invention, the three nucleotides upstream of the coding sequence may be changed from "AAA" to "CCA" and the fourth nucleotide in the coding sequence may be changes from "C" to "G". In addition, a portion or the entire N-terminus may be substituted by its counterpart of the utrophin gene. Similarly, the CR domain of the dystrophin minigene can also be substituted by its counterpart of the utrophin gene.

The dystrophin minigenes may be introduced into a mammalian subject using a variety of methods. It may be introduced into the subject in an expression cassette as a naked DNA with or without hydrodynamic-based or electroporation-based procedures. It may be introduced into the subject using non-viral vectors such as liposomes or virus-liposome complexes, or with viral vectors such as adenovirus, HSV, baculovirus, retrovirus, lentivirus, and preferably AAV. Expression of the dystrophin minigenes may be controlled by a number of regulatory elements, including but not limited to, AAV inverted terminal repeat (ITR), retrovirus long terminal repeat (LTR), cytomeglovirus (CMV) immediate early promoter and/or enhancer, CMV enhancer and chicken beta.-actin promoter (CB promoter), .alpha.-actin promoter, myosin promoter, muscle-specific creatine kinase (MCK) promoter and/or enhancer, and the like. Alternatively, the modified versions of the above promoters and the synthetic muscle promoters (Li et al. cited supra) etc. may also be used.

Expression of dystrophin minigene may be detected by immunofluorescent staining and immunoblotting (Western blotting). The functionality of mini-dystrophin may be examined by determining whether the mini-dystrophins are capable of restoring the missing DAP complexes on the myofiber plasma membrane, including the sarcoglycan complex which is not found in untreated dystrophic muscle due to the primary deficiency of dystrophin. To further investigate the functionality of the novel mini-dystrophins, it is essential to demonstrate that they can protect muscle from the pathological phenotypes. The onset of the pathology in mdx mice starts at around three weeks of age with massive waves of myofiber degeneration/regeneration. This process is characterized by the presence of central nuclei in myofibers, a primary pathological sign of muscular dystrophies. The absence or reduction of central nucleation after gene therapy would suggest that the therapy is successful. The position of nuclei in a muscle fiber may be determined by DAPI staining or H & E staining.

Muscle cryosections of 8 .mu.m thickness may be immunofluorescently stained with the Mouse-on-Mouse Kit from the Vector Laboratories (Burlingame, Calif.) according to the manufacturer's protocol, except that the cryosections may be immediately treated with the blocking buffer without the fixation step (Li et al. Gene Ther 6, 74-82 [1999]). Monoclonal antibodies against dystrophin (NCL-Dys3 and NCL-Dys2) and against alpha.-, .beta.-, and .gamma.-sarcoglycans (NCL-.alpha.-SARC, NCL-.beta.-SARC and NCL-.gamma.-SARC) may be purchased from Novocastra Laboratories Ltd (Burlingame, Calif.). Muscle cell nuclei may be counterstained with 0.01% DAPI (Sigma, St. Louis, Mo.) for 10 minutes. Photographs may be taken with a Nikon TE-300 fluorescent microscope.

Plasma membrane damage and leakage in dystrophic muscle is a major physiological defect and also a major pathological cause. To determine whether AAV mini-dystrophin treatment would be effective in protecting plasma membrane from mechanical damage, myofiber membrane integrity test may be performed by intravenous injection of Evans Blue dye. Evans Blue is a widely used vital red-fluorescent dye that is excluded by the healthy myofibers, but is taken up by the dystrophic myofibers containing leaky cell membrane due to contractile damages. A previous study of max mice revealed that the apoptotic myonuclei were mostly found in Evans Blue dye positive myofibers, thus correlating plasma membrane leakage and muscle cell apoptosis (Matsuda et al. J Biochem (Tokyo) 118, 959-64 [1995]).

Evans Blue dye (10 mg/ml in PBS) may be injected into the tail vein of C57/B10 mice, max mice, and AAV vector-treated mar mice at the dose of 0.1 mg/gram of body weight. Following dye injection, mice may be allowed continuous swimming for 20 minutes. At 15 hours after Evans Blue injection, muscles may be collected and cryosectioned. Evans Blue dye positive myofibers may be observed under the fluorescent microscope with Rhodamine filters.

Muscle constrctile force improvement was evaluated in the mdx mice after treatment with AAV vectors containing the dystrophin minigene. Tibialis anterior (TA) muscles of 2 to 3 month old mdx mice were injected with AAV-MCK-3990 vector. The injection was given in such a way that one leg was treated while the other leg in the same animal was left untreated. The latter was used as a control. At 6 months after AAV treatment, the mdx mice were anesthetized with pentobarbital sodium (70 mg/kg, i.p.) and the entire TA muscle was removed and mounted in a vertical tissue chamber for in vitro force measurement. The muscle was stimulated (Grass model S-88 stimulator and current amplifier) by use of monophasic rectangular pulses of cathodal current (1.0-ms duration). Maximum tetanic force ($P_o$) was assessed using a stimulation frequency of 75 pps delivered in a 500 ms duration train. Following the determination of $P_o$, the ability of the TA muscle to sustain force generation during repetitive lengthening activations (which should induce maximal damage to the muscle) was assessed. Peak force measured prior to lengthening was termed $P_{ISO}$. Subsequently, the muscle was lengthened at a constant velocity of 1.0 $L_o$/s from 100 to 110% $L_o$. Stimulus trains were repeated every 2-min (duty cycle 0.004) for a total of 10 cycles. Changes in $P_{ISO}$ were used to index impairment of muscle function associated with the damages caused by lengthening activations.

C. Preferred Embodiments

The following examples are meant merely to exemplify several embodiments, and should not be interpreted as limiting the scope of the claims, which are delimited only by the specification.

EXAMPLE 1

Dystrophin Minigenes and AAV Vectors Carrying the Minigenes

This example describes the construction of highly truncated dystrophin minigenes and AAV vectors carrying the minigenes. The dystrophin minigene constructs were made mainly by PCR cloning method using Pfu polymerase (Stratagene, Calif.) and human dystrophin cDNA (GenBank # NM 004006) as the template. For consistency, the numbering of the nucleotide only includes the 11,058 bp dystrophin protein coding sequence (SEQ ID NO: 1).

As depicted in FIG. 1, dystrophin minigene .DELTA.4173 (SEQ ID NO:2) contains nucleotides 1-1992 (N-terminus, hinge H1 and rods R1, R2 & R3, SEQ ID NO:3) and 8059-10227 (rods R22, R23 & R24, hinge H4 and CR domain, SEQ ID NO:4) and 11047-11058 (the last 3 amino acids of dystrophin, SEQ ID NO:5).

Dystrophin minigene .DELTA.3990 (SEQ ID NO:6) contains nucleotides 1-1668 (N-terminus, hinge H1 and rods R1 & R2, SEQ ID NO:7), 7270-7410 (hinge H3, SEQ ID NO:8), 8059-10227 (rods R22, R23 & R24, hinge H4 and CR domain, SEQ ID NO:4) and 11047-11058 (the last 3 amino acids of dystrophin, SEQ ID NO:5).

Dystrophin minigene .DELTA.3849 (SEQ ID NO:9) contains nucleotides 1-1668 (N-terminus, hinge H1 and rods R1 & R2, SEQ ID NO:7), 8059-10227 (rods R22, R23 & R24, hinge H4 and CR domain, SEQ ID NO:4), and 11047-11058 (the last 3 amino acids of dystrophin, SEQ ID NO:5).

Dystrophin minigene .DELTA.3531 (SEQ ID NO:10) contains nucleotide 1-1341 (N-terminus, hinge H1 and rods R1, SEQ ID NO:11), 8059-10277 (rods R22, R23 & R24, hinge H4 and CR domain, SEQ ID NO:4), and 11047-11058 (the last 3 amino acids of dystrophin, SEQ ID NO:5).

Dystrophin minigene .DELTA.3510 (SEQ ID NO:12) contains nucleotide 1-1668 (N-terminus, hinge H1 and rods R1 & R2, SEQ ID NO:7), 8407-10277 (rods R23 & R24, hinge H4 and CR domain, SEQ ID NO: 13) and 11047-11058 (the last 3 amino acids of dystrophin, SEQ ID NO:5).

Dystrophin minigene .DELTA.3447 (SEQ ID NO: 14) contains nucleotide 1-1992 (N-terminus, hinge H1 and rods R1, R2 & R3, SEQ ID NO:3), 8794-10277 (rod R24, hinge H4 and CR domain, SEQ ID NO:15) and 11047-11058 (the last 3 amino acids of dystrophin, SEQ ID NO:5).

The above constructs were made by blunt-end ligation of the Pfu amplified PCR products of each individual segment, so that all the protein coding sequences are precisely spliced together in frame. The PCR primers used in the reactions are listed in Table 1:

TABLE 1

PCR primers used in the cloning of dystrophin fragments

| Primer Names | Primer Sequence (5'-3') | Sequence position | |
|---|---|---|---|
| Forward primers: | | | |
| F1 (ATG-A) | ATTTTCACCATGGTTTCGTCCCAAGAAG | 1-19 (28 bp) | SEQ ID NO:16 |
| F2 (H3-1) | CAGCCTGACCTAGCTCCTGGACTGA | 7270-7294 (25 bp) | SEQ ID NO:17 |
| F3 (R22-1) | ACTCATAGATTACTGCAACAGTTCC | 8059-8083 (25 bp) | SEQ ID NO:18 |
| F4 (R23-1) | AGTTCTGACCAGTGGAAGCG | 8407-8427 (20 bp) | SEQ ID NO:19 |
| F5 (R24-1) | ACCCTTGAAAGACTCCAGGAAC | 8794-8816 (22 bp) | SEQ ID NO:20 |
| Reverse primers: | | | |
| R1 (R1-2) | TCTATGTAAATTGCTTTGTT | 1341-1361 (20 bp) | SEQ ID NO:21 |
| R2 (R2-2) | GTCTTGTAAAAGAACCCAGCGGTCT | 1668-1644 (25 bp) | SEQ ID NO:22 |
| R3 (R3-2) | CTGTGCTGTACTCTTTTCAAGTTTT | 1992-1968 (25 bp) | SEQ ID NO:23 |
| R4 (H3-2) | AGGTACCTCCAACATCAAGGAAGAT | 7410-7386 (25 bp) | SEQ ID NO:24 |
| R5 (Tail-2A) | CTACATTGTGTCGGGAGTTTCCATGTTGTC | 11058-11047, 10227-10210 (30 bp) | SEQ ID NO:25 |

The dystrophin minigenes were then subcloned into an AAV vector plasmid (SEQ ID NO:26) containing an MCK promoter, a 595 bp Hind III/BstE II fragment from plasmid p(+enh206) 358MCKCAT (Shield et al. Mol Cell Biol 16, 5058-68 [1996]), and a 60 bp small polyA signal sequence, resulting in AAV vector constructs AAV-MCK-.DELTA.4173 (SEQ ID NO:27), AAV-MCK-.DELTA.3990 (SEQ ID NO:28), AAV-MCK-.DELTA.3849 (SEQ ID NO:29), AAV-MCK-3531 (SEQ ID NO:30), AAV-MCK-3510 (SEQ ID NO:31) and AAV-MCK-3447 (SEQ ID NO:32).

Similarly, the dystrophin minigenes were also cloned into an AAV vector plasmid (SEQ ID NO:33) containing a CMV promoter (620 bp) and the small polyA signal sequence, resulting in AAV vector constructs AAV-CMV-.DELTA.3990 (SEQ ID NO:34), AAV-CMV-.DELTA.3849 (SEQ ID NO:35). In addition, the dystrophin minigene .DELTA.3849 was cloned into an AAV vector plasmid containing an MCK enhancer, a CMV promoter, and the small polyA signal sequence, resulting AAV vector construct AAV-E-CMV-3849 (SEQ ID NO:36).

The recombinant viral vector stocks were produced precisely according to the three-plasmid co-transfection method as described by Xiao et al. (cited supra). The AAV viral vectors were subsequently purified twice through CsCl density gradient ultracentrifugation using the previously published protocols (Snyder et al. in Current Protocols in Human Genetics, eds. Dracopoli et al. [John Wiley & Sons Ltd., New York], pp. 12.1.1-12.2.23. [1996]). The vector titers of viral particle number were determined by DNA dot blot method (Snyder et al. cited supra), and were approximately 5.times.10.sup.12 genome copies (GC) per ml.

EXAMPLE 2

Restoration of DAP Complexes

This example describes whether dystrophin minigene products still retain the major biochemical functionality including submembrane localization and interaction with dystrophin associated protein (DAP) complexes. Healthy C57/B10 mice and dystrophic mdx mice were purchased from The Jackson Laboratory (Bar Harbor, Me.). Ten-day old mdx pups or 50-day old mdx adult mice were injected into the hindleg gastrocnemius muscle with 50.mu.l (5.times.10.sup.10 GC) of different AAV mini-dystrophin vectors.

At three months and six months after vector injection, the muscles were collected for evaluation of mini-dystrophin expression and biochemical restoration of the DAP complexes, which were absent due to the primary deficiency of dystrophin. IF staining on thin sections of AAV treated muscles, using an antibody (Dys3) specific to human dystrophin, revealed widespread vector transduction and correct submembrane location of the mini-dystrophins in a majority of the myofibers, especially in muscles treated with AAV vectors containing dystrophin minigene .DELTA.3849 or .DELTA.3990 (FIGS. 2A, 2B and 2C; FIG. 3A). As expected, the equivalent muscle from the age-matched healthy C57/B 10 mice showed indistinguishable dystrophin staining pattern, when stained with an antibody (Dys2) that recognizes both mouse and human dystrophin C-terminal region (FIG. 2C). As expected, this antibody (Dys2) failed to stain the AAV treated mdx muscle due to deletion of the C-terminal region in our dystrophin minigenes (data not shown). This result further confirmed the identity of mini-dystrophins that were derived from the AAV vectors. Consistently, the untreated mdx control muscle showed no dystrophin staining (FIG. 2C) except the very few somatic revertant myofibers recognized by Dys2 antibody. Furthermore, injection of AAV mini-dystrophin vectors into the adult mdx muscle (gastrocnemius) showed similar results when examined for dystrophin expression at 2 and 4 months after injection of AAV MCK vectors (FIGS. 3C-3F), or at 6 months after injection of AAV CMV vectors (FIGS. 3G and 3H). Importantly, there was no cytotoxic T-lymphocyte (CTL) destruction against the myofibers that persistently expressed mini-dystrophins of human origin from AAV vectors, either driven by a CMV promoter or by a muscle-specific MCK promoter.

Immunofluorescent staining using three antibodies against .alpha., .beta., and .gamma. sarcoglycans respectively, showed positive results in all of the consecutive thin sections adjacent to those stained with dystrophin antibodies (FIG. 2C). These results provided evidence of biochemical functionality of the mini-dystrophins, which lack the C-terminal domain but are still capable of interacting with the DAP complexes.

EXAMPLE 3

Amelioration of Dystrophic Pathology

This example demonstrates that dystrophin minigene products can protect muscle from the pathological phenotypes. The onset of the pathology in mdx mice starts at around three weeks of age with massive waves of myofiber degeneration/regeneration. This process is characterized by the presence of central nuclei in myofibers, a primary pathological sign of muscular dystrophies. The absence or reduction of central nucleation after gene therapy would suggest that the therapy is successful. Therefore, we initially chose to test the AAV mini-dystrophin constructs in young mdx mice (10-day old) before the onset of central nucleation, to see whether muscle degeneration/regeneration can be prevented.

Figure 2B:
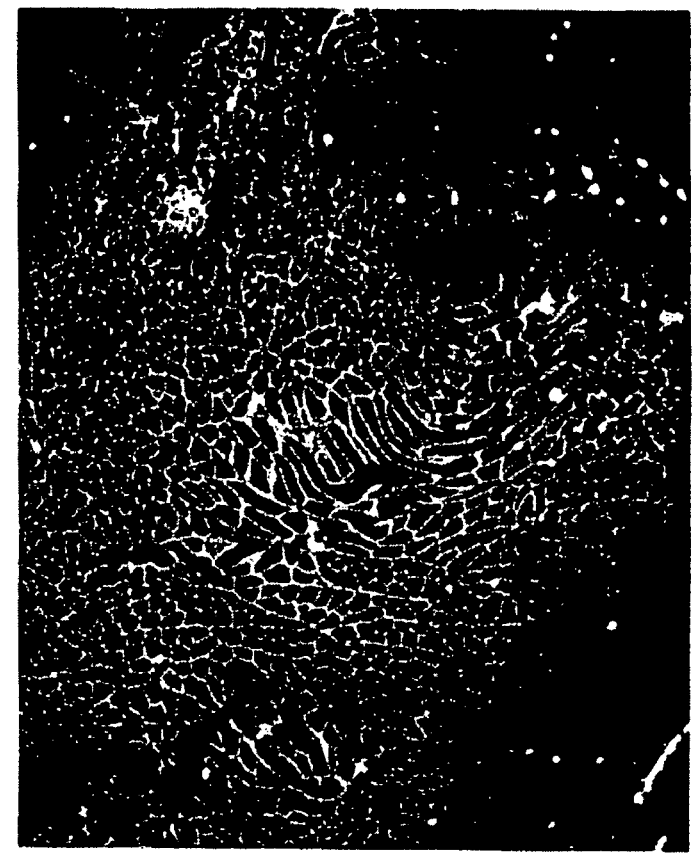
FIGS. 2A and 2B show immunofluorescent (IF) analysis of the dystrophin and DAP complexes in gastrocnemius muscle of mdx muscle at 3-months after treatment with construct AAV-MCK-.DELTA.3849 or AAV-MCK-.DELTA.3990, respectively.
Figure 2A:
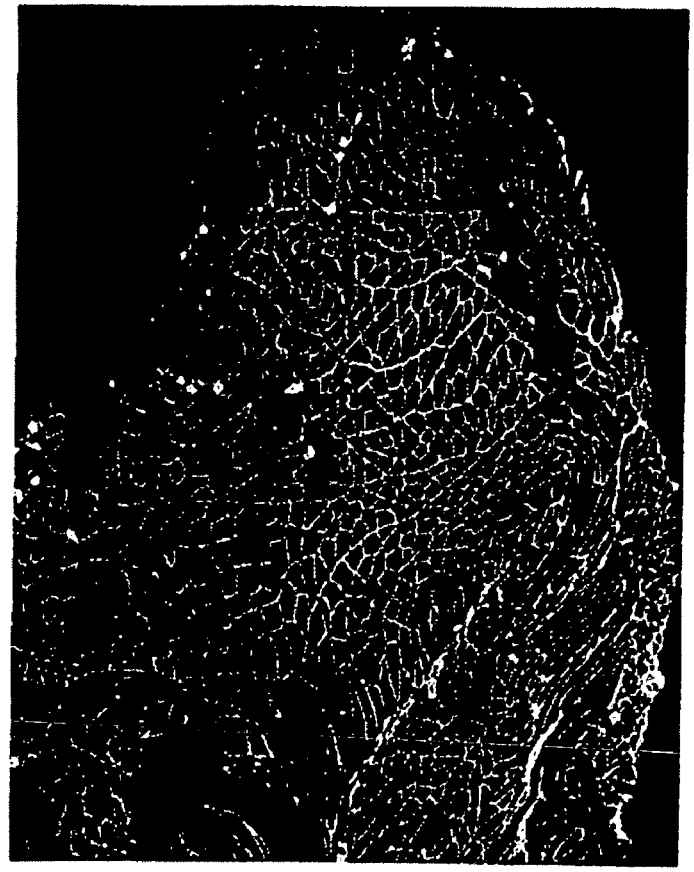
Figure 2C:
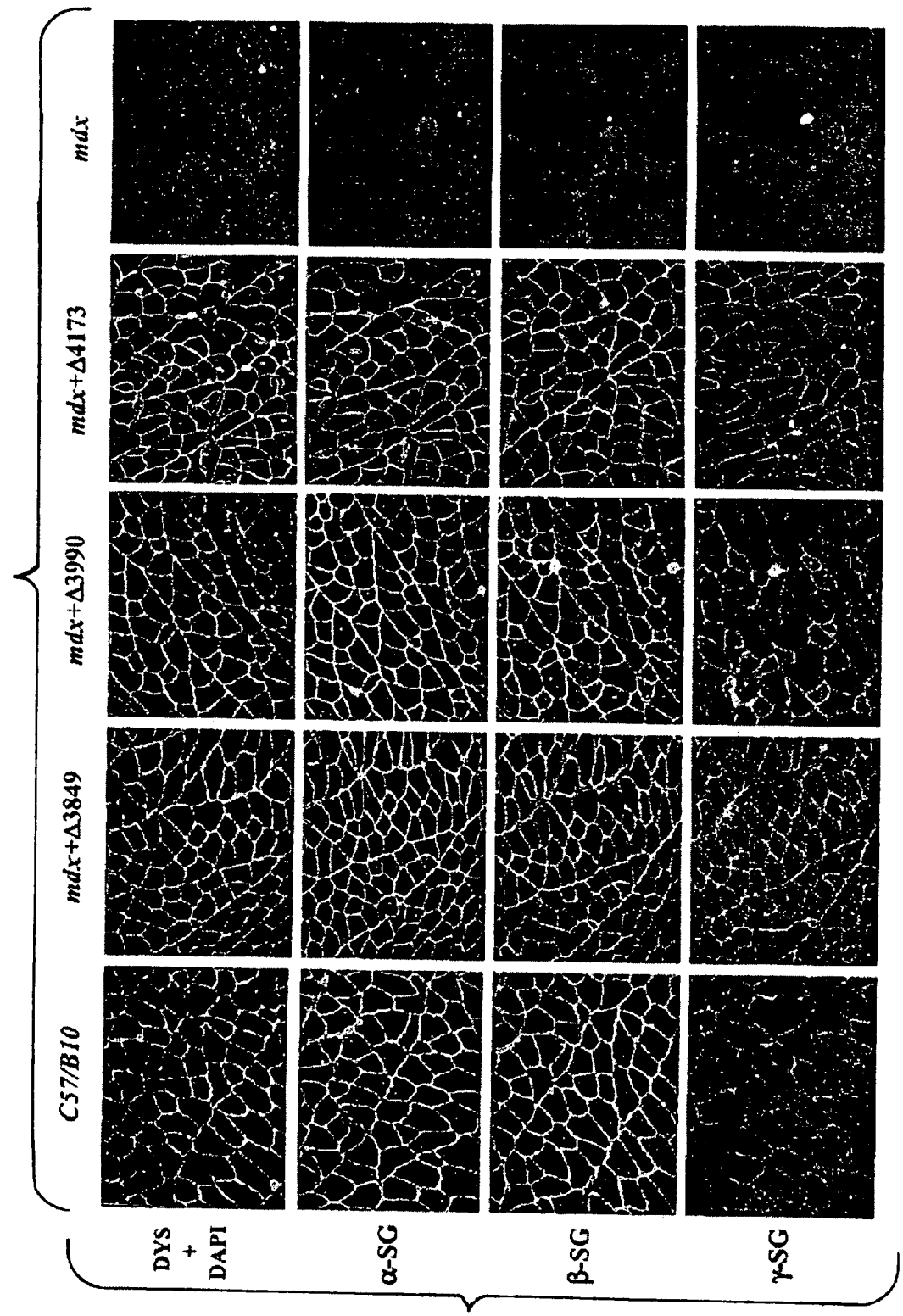
FIG. 2C shows IF analysis of the dystrophin and DAP complexes in gastrocnemius muscle from 15-week old normal C57/B10 mice, from mdx mice treated either with vector AAV-MCK-.DELTA.3849, AAV-MCK-.DELTA.3990 or AAV-MCK-.DELTA.4173, or from untreated mdx mice.
Figure 3A:
FIG. 3A shows mini-dystrophin expression in mdx mice treated with AAV-MCK-.DELTA.3849 at 10 days of age. The animals were sacrificed 6 months post viral injection.
Figure 5B:
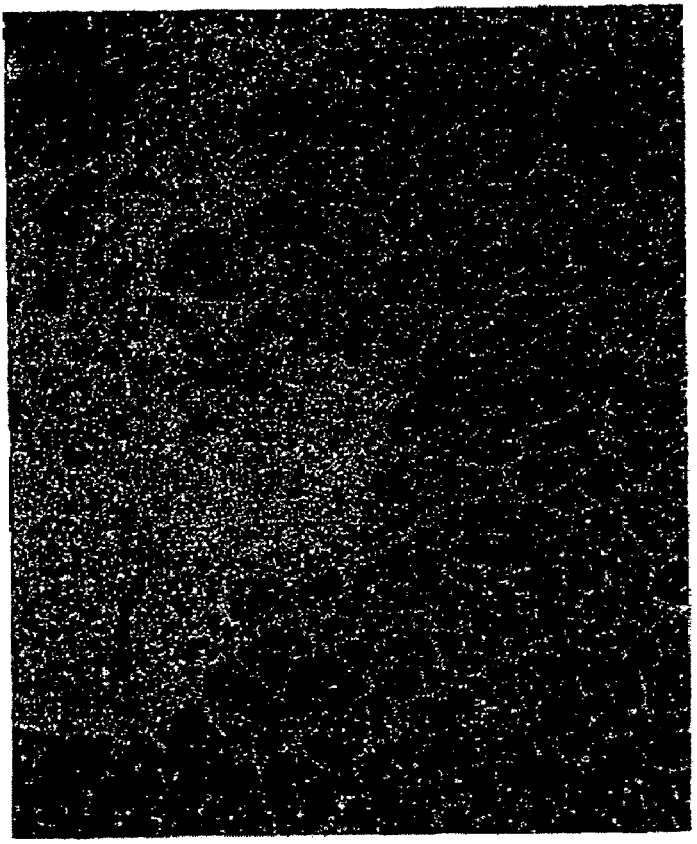
FIG. 5B shows the IF analysis of mini-dystrophin expression from construct CMV-M3, which contains 1 rod (a hybrid rod between rod R1 & rod R24, see FIG. 1 and Yuasa et al). Note that the muscle cell morphology and central nucleation were not improved after its injection into young mdx mice.
Figure 5A:
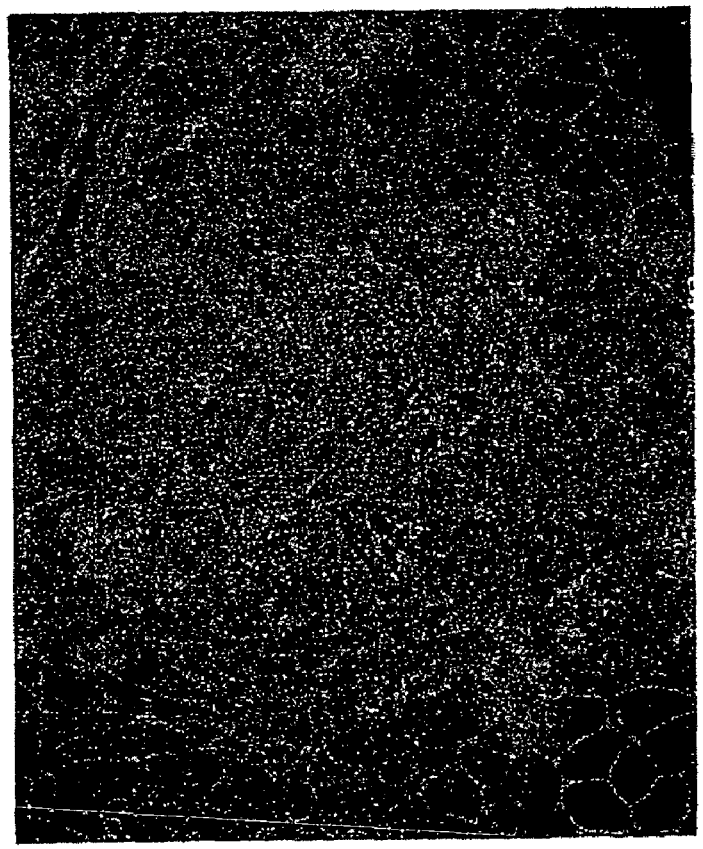
FIG. 5A shows the IF analysis of mini-dystrophin expression from construct .DELTA.2796, which contains two rods (rod1 & rod24, see FIG. 1). Note that the muscle cell morphology and central nucleation were not improved after its injection into young mdx mice.

Histological examination of the mdx muscles at 3 and 6 months after AAV mini-dystrophin (containing more than 2 rod domains) treatment, which was prior to the onset of central nucleation, showed nearly exclusive (.about.98%) peripheral nucleation in the mini-dystrophin positive myofibers, as revealed by dystrophin immunostaining and myonuclei counterstaining with DAPI (FIG. 2A, FIG. 2B, FIG. 2C first column; FIG. 3A and Table 2). The mutual exclusivity between mini-dystrophin expression and central nucleation in the vector treated mdx muscle precisely mirrored that of the normal muscle (FIG. 2C and Table 2). In addition, the myofibers positive for mini-dystrophin expression also exhibited consistent myofiber sizes and polygonal shapes indistinguishable from those of the normal muscle (FIGS. 2A, 2B and 2C). By contrast, the untreated mdx muscle showed extensive (75.4%) central nucleation (Table 2)), with additional signs of dystrophic pathology including wide variation of myofiber sizes, round myofiber shapes, and fibrosis (FIG. 2C). Noticeably, the mdx muscle treated with constructs .DELTA.2796 and M3 (containing 2 rods and 1 rod, respectively, see FIG. 1.) showed the same morphology as the untreated mdx muscle, except for the positive IF staining of the mini-dystrophin, which is not functional in terms of improving muscle morphology, pathology and preventing muscle degeneration/regeneration and central nucleation (FIGS. 5A and 5B; Table 2). Hence, treatment of dystrophic muscle by AAV vector with minigenes containing more than 2 rods (See FIG. 1.) prevented dystrophic pathology and led to normal histology in terms of peripheral nucleation, consistent myofiber size and lack of fibrosis in the mini-dystrophin positive areas. These results unequivocally demonstrated the absence of muscle degeneration due to the therapeutic effects of the novel mini-dystrophins in young mdx mice.

Figure 3B:
FIG. 3B shows dystrophin expression in untreated 6-month-old mdx mice.
Figure 3C:
FIG. 3C shows mini-dystrophin expression in mdx mice treated with AAV-MCK-.DELTA.3849 as adult. The animals were sacrificed 2-months post viral injection.
Figure 3D:
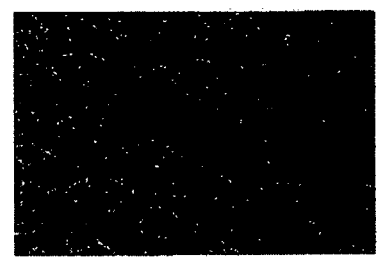
FIG. 3D shows mini-dystrophin expression in mdx mice treated with AAV-MCK-.DELTA.3990 as adult. The animals were sacrificed 2 months post viral injection.
Figure 3E:
FIG. 3E shows mini-dystrophin expression in mdx mice treated with AAV-MCK-.DELTA.3849 as adult. The animals were sacrificed 4 months post viral injection.
Figure 3F:
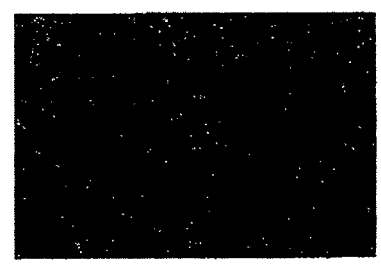
FIG. 3F shows mini-dystrophin expression in mdx mice treated with AAV-MCK-.DELTA.3990 as adult. The animals were sacrificed 4 months post viral injection.
Figure 3G:
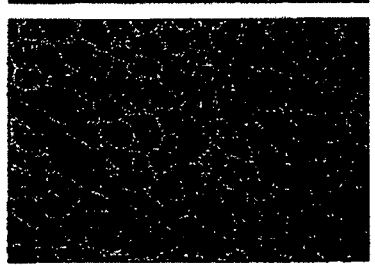
FIG. 3G shows mini-dystrophin expression in mdx mice treated with AAV-CMV-.DELTA.3849 as adult. The animals were sacrificed 6 months post viral injection.
Figure 3H:
FIG. 3H shows mini-dystrophin expression in mdx mice treated with AAV-CMV-.DELTA.3990 as adult. The animals were sacrificed 6 months post viral injection.

We subsequently tested AAV vectors containing dystrophin minigenes with more than 2 rods in treating adult mdx mice (45 days of age) after the onset of massive waves of degeneration/regeneration, to see whether the pathological process can be stopped or reversed. At the time of vector injection, a majority (.about.75%) of the myofibers already underwent degeneration/regeneration process and displayed central nucleation. At 2 months, 4 months and 6 months after AAV mini-dystrophin injection, widespread dystrophin expression was observed accompanied by normal myofiber morphology and lack of fibrosis in the dystrophin positive areas (FIGS. 3A and 3B). By contrast, muscle of untreated mdx mice (FIG. 3B), or areas of treated muscle without successful vector gene transfer, manifested progressive degeneration and fibrosis. In addition, a reduction of central nucleation in mini-dystrophin positive myofibers was observed (from approximately 75% before vector treatment to 35-50% after vector treatment; see Table 2). The partial reversal of central nucleation was also observed in healthy mouse muscle, where a majority of the myonuclei remained centrally located once experiencing a transient pathology such as myotoxin treatment (Martin et al. Muscle Nerve 11:588-96 [1988]). Persistence of central nucleation was also observed after treatment of adult mdx muscle with a gutless adenovirus vector containing the full-length dystrophin cDNA. Based on the above observations, our novel mini-dystrophin genes (containing more than 2 rods) demonstrated therapeutic effects in ameliorating dystrophic pathology in both young and adult mdx muscles.

EXAMPLE 4

Protection of Myofiber Membrane Integrity

Figure 4A:
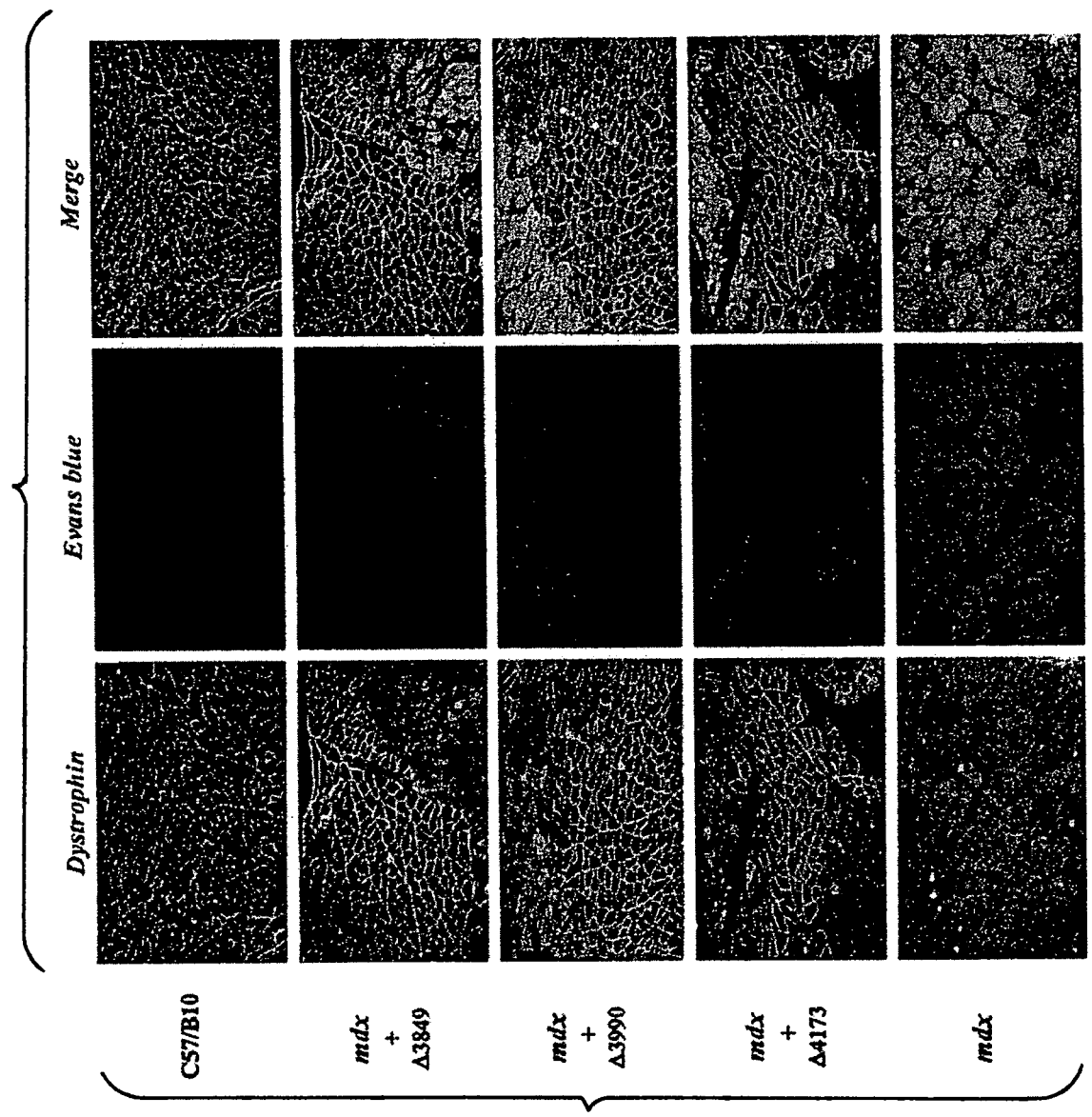
FIG. 4A shows protection of muscle plasma membrane integrity by dystrophin minigenes in mdx mice treated at 10 days of age.
Figure 4B:
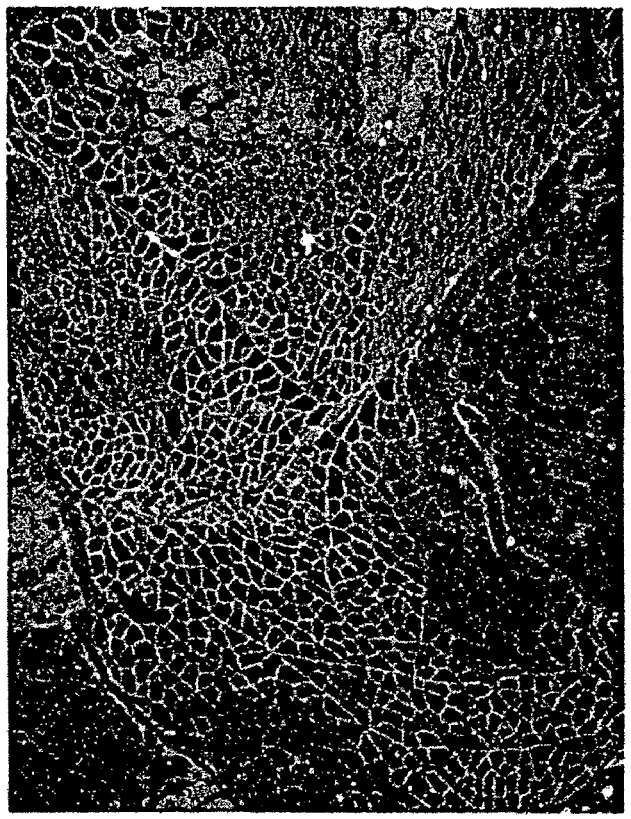
FIG. 4B shows protection of muscle plasma membrane integrity by dystrophin minigenes in mdx mice treated as adult.
Figure 4B:

This example demonstrates that mini-dystrophins containing more than 2 rods (see FIG. 1.) are capable of protect myofiber membrane integrity. Initially, Evans Blue was administered into the tail vein of mdx mice that were treated at young age (10-day old) with AAV vectors three months before. The age-matched untreated mdx mice and healthy C57/B10 mice were used as controls. To induce mechanical stress, the mice were allowed to exercise by continuous swimming for 20 minutes. Muscles were then collected and examined for dystrophin expression as well as for Evans Blue dye uptake. As expected, muscle from healthy mice revealed uniform dystrophin staining across the muscle sections and no uptake of the dye by the myofibers (FIG. 4A, top row). The AAV vector treated mdx muscle showed results consistent with the healthy muscle, thus mutual exclusivity of dystrophin expression and dye uptake (FIG. 4A second to fourth rows). Dye uptake (red fluorescence) was found only in myofibers that lacked mini-dystrophin expression in the areas not transduced by AAV vectors (FIG. 4A, $2^{nd}$, $3^{rd}$ and $4^{th}$ rows). By contrast, the untreated mdx muscle revealed absence of dystrophin and extensive dye uptake (FIG. 4A, bottom row). More importantly, AAV mini-dystrophin treatment of adult mdx muscle also achieved similar results in protecting myofibers from plasma membrane leakage when analyzed at 2 months and 6 months after vector injection (FIG. 4B). These results unequivocally demonstrated the physiological functionality of the novel mini-dystrophins in maintaining membrane integrity and protecting myofibers from mechanical damages in both young and adult mdx mice.

TABLE 2

| AAV mini-dystrophin gene transfer in young and adult mdx mice | | | | |
|---|---|---|---|---|
| Animals* & vectors | n | Age at Vector injection | Months post injection | % Dystrophin positive fibers | % Central nuclei** |
| mdx + A3510 | 4 | 12 days | 3 | 35-80 | 1.06 (68/6413) |
| mdx + A3531 | 4 | 12 days | 3 | 25-40 | 1.72 (37/2140) |
| mdx + A3849 | 4 | 10 days | 3 | 56-88 | 1.02 (72/7098) |
| mdx + A3990 | 4 | 10 days | 3 | 50-80 | 0.99 (56/5652) |
| mdx + A4173 | 4 | 10 days | 3 | 15-25 | 0.93 (26/2791) |
| mdx + A3849 | 4 | 10 days | 6 | 40-60 | 2.80 (51/1824) |

TABLE 2-continued

AAV mini-dystrophin gene transfer in young and adult mdx mice

| Animals* & vectors | n | Age at Vector injection | Months post injection | % Dystrophin positive fibers | % Central nuclei** |
|---|---|---|---|---|---|
| mdx + A3990 | 2 | 10 days | 6 | 35-45 | 2.30 (34/1478) |
| mdx + A3849 | 2 | 50 days | 2 | 35-50 | 34.76 (510/1467) |
| mdx + A3990 | 2 | 50 days | 2 | 35-40 | 34.18 (685/2004) |
| mdx + A3849 | 4 | 50 days | 4 | 20-25 | 44.24 (615/1390) |
| mdx + A3990 | 4 | 50 days | 4 | 20-30 | 46.18 (695/1505) |
| C57/B10 | 4 | No injection | N/A | 100 | 1.45 (56/3860) |
| mdx | 4 | No injection | N/A | <1 | 75.4 (2382/3160) |
| mdx + A2796 | 4 | 12 days | 3 | 30-45 | 72 (3888/5400) |
| mdx + M3 | 8 | 10-12 days | 3 | 20-65 | 81 (5589/6900) |

Note:
*Untreated control mdx and C57/B10 mice were about 3 months old at the endpoints of experiments. AAV vectors were driven by n MCK promoter.
**All numbers were collected from dystrophin-positive myofibers which were photographed following immunofluorescent staining and DAPI counterstaining, except in untreated mdx mice which had extensive central nucleation and very few dystrophin-positive

EXAMPLE 5

Restoration of Muscle Strength

Figure 6:
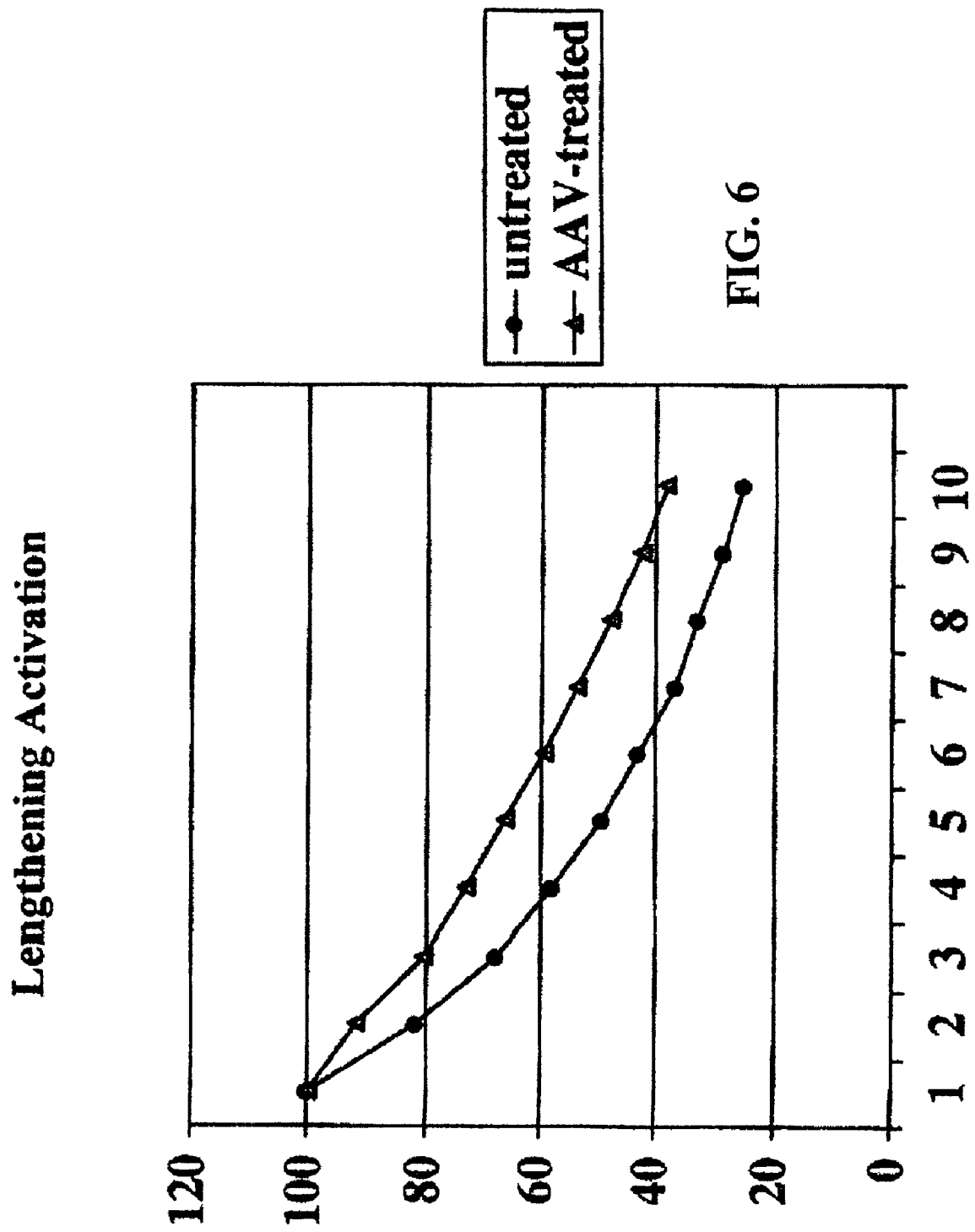
FIG. 6 shows muscle force improvement after AAV-MCK-.DELTA.3990 vector injection into the TA muscle of adult mdx mice. After 10 cycles of lengthening activation the untreated mdx TA muscles (n=8) had only 23% of the force output remaining, while the AAV treated mdx TA muscles (n=8) had nearly 40% of the force output remaining.

This example demonstrates that mini-dystrophins restore muscle strength in mdx mice. Muscle contractile force improvement was evaluated in the mdx mice after treatment with AAV vectors containing the dystrophin minigene. Tibialis anterior (TA) muscles of 2 to 3 month old mdx mice were injected with AAV-MCK-3990 vector. The injection was given in such a way that one leg was treated while the other leg in the same animal was left untreated. The latter was used as a control. At 6 months after AAV treatment, the mdx mice were anesthetized and the entire TA muscle was removed and mounted in a vertical tissue chamber for in vitro force measurement. The muscle was stimulated by the use of monophasic rectangular pulses of cathodal current (1.0-ms duration). Maximum tetanic force ($P_o$) was assessed using a stimulation frequency of 75 pps delivered in a 500 ms duration train. Following the determination of $P_o$, the ability of the TA muscle to sustain force generation during repetitive lengthening activations (which should induce maximal damage to the muscle) was assessed. Peak force measured prior to lengthening was termed $P_{ISO}$. Subsequently, the muscle was lengthened at a constant velocity of 1.0 $L_o$/s from 100 to 110% $L_o$. Stimulus trains were repeated every 2-min (duty cycle 0.004) for a total of 10 cycles. Changes in $P_{ISO}$ were used to index impairment of muscle function associated with the damages caused by lengthening activations. As shown in FIG. 6, after 10 cycles of lengthening activations the untreated TA muscles (n=8) had only 23% of the force output remaining, while the AAV treated TA muscles (n=8) had nearly 40% of the force output remaining. This result strongly indicates that the dystrophin minigene can protect the muscle from mechanical force induced damage, therefore, restore the muscle strength.

In summary, these examples demonstrate that dystrophin gene can be successfully reduced to one third (⅓) of its 11 kb full-length coding sequence, without compromising essential functions in protecting muscles from dystrophic phenotypes. Moreover, we have demonstrated for the first time that intramuscular injection of AAV vectors carrying the novel human dystrophin minigenes can achieve efficient and long-term therapeutic effects in a mammalian animal model. Long-term correction of both biochemical and physiological defects in the dystrophic muscles was realized by the persistent mini-dystrophin expression from AAV vectors, and the apparent lack of CTL immune response against myofibers expressing human dystrophin.

EXAMPLE 6

Construction and Testing of Retroviral Vectors

Retrovirus based gene transfer vectors are widely used to introduce transgenes permanently into the in vitro cultured cells. Those target cells may be stable cell lines or primary cell cultures derived from freshly isolated tissues or bone marrow. Some of the primary cell cultures may contain progenitor cells or stem cells, for example, hematopoietic stem cells and muscle derived stem cells. Those stem cells possess the capability of differentiating into mature muscle cells, i.e. myotubes and myofibers. Therefore, ex vivo gene transfer of the dystrophin minigenes via the retroviral vector may be a useful method to treat muscular dystrophin by infecting the stem cells isolated from the patients, who lack the dystrophin protein due to mutations in the dystrophin gene. To examine the usefulness of retroviral vectors, we cloned dystrophin minigene .DELTA.3990 or .DELTA.3849 (PCR product) into the Stu I site of a retroviral vector plasmid pLNCX (Clontech, Calif., USA). Two retroviral vector plasmids were obtained respectively carrying dystrophin minigene .DELTA.3990 or .DELTA.3849 under the control of a CMV promoter. The retroviral vector particles were produced by transfecting the vector plasmid pLNCX.DELTA.3990 or pLNCX.DELTA.3849 into the packaging cell line Ampho-Pack 293 (Clontech, Calif., USA). The above retrovirus particles were used to infect the myoblast cells isolated from the muscle tissue of mdx mice. Selection drug G418 was used to kill the cells not infected by the retroviral vector, which carried a Neo.sup.r gene to confer the G418 resistance. The G418 resistant myoblast cells containing the A3990 or A3849 minigene were induced to differentiation into myotubes by culturing with 2% horse serum in DMED media. The differentiated myotubes were subjected to immunofluorescent staining using monoclonal antibody (Dys-3) against the minigene protein product. A majority of the myotubes were stained positive for the dystrophin minigene expression, demonstrating the minigene can be successfully introduced into muscle progenitor cells by retroviral vectors. Such retroviral vector infected progenitor cells or stem cells may be used for the purpose of ex vivo gene therapy for Duchenne and Becker muscular dystrophies.

The Sequence Listing of U.S. patent application Ser. No. 09/845,416 hereby is incorporated herein by reference in its entirety.

What is claimed is:

1. An isolated nucleotide sequence comprising a dystrophin minigene encoding a protein consisting of:
   (a) a N-terminal domain;
   (b) not less than five nor more than six rod repeats;
   (c) an H1 domain of a dystrophin protein and an H4 domain of the dystrophin protein; and
   (d) a cysteine-rich domain,
   wherein:
   the N-terminal domain is selected from a group consisting of a N-terminal domain of the dystrophin protein, a modified N-terminal domain of the dystrophin protein, and a N-terminal domain of a utrophin protein;
   the rod repeats are selected from a group consisting of rod repeats in the dystrophin protein, rod repeats in the utrophin protein, and rod repeats in a spectrin protein;
   the cysteine-rich domain is the cysteine-rich domain of the dystrophin protein or the utrophin protein, and
   wherein the dystrophin minigene is capable of ameliorating dystrophic pathology when expressed in a dystrophic muscle.

2. An isolated nucleotide sequence comprising a dystrophin minigene encoding a protein consisting of:
   (a) a N-terminal domain;
   (b) not less than five nor more than six rod repeats;
   (c) H1 domain of a dystrophin protein and an H4 domain of the dystrophin protein;
   (d) a cysteine-rich domain; and
   (e) the last three amino acids of a C-terminal domain of the dystrophin protein,
   wherein:
   the N-terminal domain is selected from a group consisting of a N-terminal domain of the dystrophin protein, a modified N-terminal domain of the dystrophin protein, and a N-terminal domain of a utrophin protein;
   the rod repeats are selected from a group consisting of rod repeats in the dystrophin protein, rod repeats in the utrophin protein, and rod repeats in a spectrin protein;
   the cysteine-rich domain is the cysteine-rich domain of the dystrophin protein or the utrophin protein, and
   wherein the dystrophin minigene is capable of ameliorating dystrophic pathology when expressed in a dystrophic muscle.

3. An isolated nucleotide sequence comprising a dystrophin minigene encoding a protein or the complement of the dystrophin minigene, wherein the dystrophin minigene is capable of ameliorating dystrophic pathology when expressed in a dystrophic muscle, and wherein the protein comprises:
   (a) a N-terminal domain of a dystrophin protein or a modified N-terminal domain of the dystrophin protein;
   (b) not less than five nor more than six rod repeats of the dystrophin protein;
   (c) an H1 domain of a dystrophin protein and an H4 domain of the dystrophin protein; and
   (d) a cysteine-rich domain of the dystrophin protein, wherein said nucleotide sequence has fewer than 5,000 nucleotides.

4. The isolated nucleotide sequence of claim 3, wherein said protein further comprises an H2 domain of the dystrophin protein or an H3 domain of the dystrophin protein.

5. An isolated nucleic acid sequence comprising a dystrophin minigene encoding a central rod domain consisting of not less than five nor more than six central rod repeats, and having a length less than 5 kilobases.

6. A recombinant adeno-associated virus vector, comprising the nucleotide sequence of claim 1 operably linked to an expression control element.

7. The recombinant adeno-associated virus vector of claim 6, wherein the expression control element is an MCK promoter or a CMV promoter.

8. An AAV vector including a dystrophin, utrophin or spectrin nucleotide sequence encoding a shortened rod domain consisting of not less than five nor more than six rod repeats and operably linked to an expression control element effective to express a corresponding dystrophin, utrophin or spectrin polypeptide sequence effective for treating Duchenne Muscular Dystrophy or Becker Muscular Dystrophy.

9. An AAV vector including a dystrophin minigene encoding a central rod domain consisting of not less than five nor more than six central rod domain repeats.

10. The AAV vector according to claim 9, wherein the central rod domain of the dystrophin minigene consists of five central rod repeats.

11. The isolated nucleotide sequence of claim 1, wherein the number of rod repeats is five.

12. The isolated nucleotide sequence of claim 1, wherein the number of rod repeats is six.

13. The AAV vector according to claim 8,
    wherein the dystrophin nucleotide sequence encodes a shortened rod domain consisting of five rod domain repeats.

14. The AAV vector according to claim 8,
    wherein the dystrophin nucleotide sequence encodes a shortened rod domain consisting of six rod domain repeats.

* * * * *

SEQUENCE LISTING

<160> NUMBER OF SEQ ID NOS: 36

<210> SEQ ID NO 1
<211> LENGTH: 11058
<212> TYPE: DNA
<213> ORGANISM: Homo sapiens

<400> SEQUENCE: 1

| | | | | | |
|---|---|---|---|---|---:|
| atgctttggt | gggaagaagt | agaggactgt | tatgaaagag | aagatgttca | aaagaaaaca | 60 |
| ttcacaaaat | gggtaaatgc | acaattttct | aagtttggga | agcagcatat | tgagaacctc | 120 |
| ttcagtgacc | tacaggatgg | gaggcgcctc | ctagacctcc | tcgaaggcct | gacagggcaa | 180 |
| aaactgccaa | agaaaaagg | atccacaaga | gttcatgccc | tgaacaatgt | caacaaggca | 240 |
| ctgcgggttt | tgcagaacaa | taatgttgat | ttagtgaata | ttggaagtac | tgacatcgta | 300 |
| gatgaaatc | ataaactgac | tcttggtttg | atttggaata | taatcctcca | ctggcaggtc | 360 |
| aaaaatgtaa | tgaaaaatat | catggctgga | ttgcaaccaa | ccaacagtga | aaagattctc | 420 |
| ctgagctggg | tccgacaatc | aactcgtaat | tatccacagg | ttaatgtaat | caacttcacc | 480 |
| accagctggt | ctgatggcct | ggctttgaat | gctctcatcc | atagtcatag | gccagaccta | 540 |
| tttgactgga | atagtgtggt | ttgccagcag | tcagccacac | aacgactgga | acatgcattc | 600 |
| aacatcgcca | gatatcaatt | aggcatagag | aaactactcg | atcctgaaga | tgttgatacc | 660 |
| acctatccag | ataagaagtc | catcttaatg | tacatcacat | cactcttcca | agttttgcct | 720 |
| caacaagtga | gcattgaagc | catccaggaa | gtggaaatgt | tgccaaggcc | acctaaagtg | 780 |
| actaaagaag | aacattttca | gttacatcat | caaatgcact | attctcaaca | gatcacggtc | 840 |
| agtctagcac | agggatatga | gagaacttct | tcccctaagc | ctcgattcaa | gagctatgcc | 900 |
| tacacacagg | ctgcttatgt | caccacctct | gaccctacac | ggagcccatt | tccttcacag | 960 |
| catttggaag | ctcctgaaga | caagtcattt | ggcagttcat | tgatggagag | tgaagtaaac | 1020 |
| ctggaccgtt | atcaaacagc | tttagaagaa | gtattatcgt | ggcttctttc | tgctgaggac | 1080 |
| acattgcaag | cacaaggaga | gatttctaat | gatgtggaag | tggtgaaaga | ccagtttcat | 1140 |
| actcatgagg | ggtacatgat | ggatttgaca | gcccatcagg | gccgggttgg | taatattcta | 1200 |
| caattgggaa | gtaagctgat | tggaacagga | aaattatcag | aagatgaaga | aactgaagta | 1260 |
| caagagcaga | tgaatctcct | aaattcaaga | tgggaatgcc | tcagggtagc | tagcatggaa | 1320 |
| aaacaaagca | atttacatag | agttttaatg | gatctccaga | atcagaaact | gaagagttg | 1380 |
| aatgactggc | taacaaaaac | agaagaaaga | acaaggaaaa | tggaggaaga | gcctcttgga | 1440 |
| cctgatcttg | aagacctaaa | acgccaagta | caacaacata | aggtgcttca | agaagatcta | 1500 |
| gaacaagaac | aagtcagggt | caattctctc | actcacatgg | tggtggtagt | tgatgaatct | 1560 |
| agtggagatc | acgcaactgc | tgctttggaa | gaacaactta | aggtattggg | agatcgatgg | 1620 |
| gcaaacatct | gtagatggac | agaagaccgc | tgggttcttt | tacaagacat | cctgctcaaa | 1680 |
| tggcaacgtc | ttactgaaga | acagtgcctt | tttagtgcat | ggcttcaga | aaagaagat | 1740 |
| gcagtgaaca | agattcacac | aactggcttt | aaagatcaaa | atgaaatgtt | atcaagtctt | 1800 |
| caaaaactgg | ccgttttaaa | agcggatcta | gaaaagaaaa | agcaatccat | gggcaaactg | 1860 |
| tattcaatca | aacaagatct | tctttcaaca | ctgaagaata | agtcagtgac | ccagaagacg | 1920 |
| gaagcatggc | tggataactt | tgcccggtgt | gggataatt | tagtccaaaa | acttgaaaag | 1980 |
| agtacagcac | agatttcaca | ggctgtcacc | accactcagc | catcactaac | acagacaact | 2040 |

```
gtaatggaaa cagtaactac ggtgaccaca agggaacaga tcctggtaaa gcatgctcaa    2100
gaggaacttc caccaccacc tccccaaaag aagaggcaga ttactgtgga ttctgaaatt    2160
aggaaaaggt tggatgttga tataactgaa cttcacagct ggattactcg ctcagaagct    2220
gtgttgcaga gtcctgaatt tgcaatcttt cggaaggaag gcaacttctc agacttaaaa    2280
gaaaaagtca atgccataga gcagaaaaaa gctgagaagt tcagaaaact gcaagatgcc    2340
agcagatcag gtcaggccct ggtggaacag atggtgaatg agggtgttaa tgcagatagc    2400
atcaaacaag cctcagaaca actgaacagc cggtggatcg aattctgcca gttgctaagt    2460
gagagactta actggctgga gtatcagaac aacatcatcg ctttctataa tcagctacaa    2520
caattggagc agatgacaac tactgctgaa aactggttga aaatccaacc caccacccca    2580
tcagagccaa cagcaattaa aagtcagtta aaaatttgta aggatgaagt caaccggcta    2640
tcaggtcttc aacctcaaat tgaacgatta aaaattcaaa gcatagccct gaaagagaaa    2700
ggacaaggac ccatgttcct ggatgcagac tttgtggcct ttacaaatca ttttaagcaa    2760
gtcttttctg atgtgcaggc cagagagaaa gagctacaga caattttttga cactttgcca    2820 ccaatgcgct atcaggagac catgagtgcc atcaggacat gggtccagca gtcagaaacc    2880
aaactctcca tacctcaact tagtgtcacc gactatgaaa tcatggagca gagactcggg    2940
gaattgcagg ctttacaaag ttctctgcaa gagcaacaaa gtggcctata ctatctcagc    3000
accactgtga agagatgtc gaagaaagcg ccctctgaaa ttagccggaa atatcaatca    3060
gaatttgaag aaattgaggg acgctggaag aagctctcct cccagctggt tgagcattgt    3120
caaaagctag aggagcaaat gaataaactc cgaaaaattc agaatcacat acaaaccctg    3180
aagaaatgga tggctgaagt tgatgttttt ctgaaggagg aatggcctgc ccttggggat    3240
tcagaaattc taaaaaagca gctgaaacag tgcagacttt tagtcagtga tattcagaca    3300
attcagccca gtctaaacag tgtcaatgaa ggtgggcaga agataaagaa tgaagcagag    3360
ccagagtttg cttcgagact tgagacagaa ctcaaagaac ttaacactca gtgggatcac    3420
atgtgccaac aggtctatgc cagaaaggag gccttgaagg gaggtttgga gaaaactgta    3480
agcctccaga aagatctatc agagatgcac gaatggatga cacaagctga agaagagtat    3540
cttgagagag attttgaata taaaactcca gatgaattac agaaagcatt tgaagagatg    3600
aagagagcta agaagagggc ccaacaaaaa gaagcgaaag tgaaactcct tactgagtct    3660
gtaaatagtg tcatagctca agctccacct gtagcacaag aggccttaaa aaaggaactt    3720
gaaactctaa ccaccaacta ccagtggctc tgcactaggc tgaatgggaa atgcaagact    3780
ttggaagaag tttgggcatg ttggcatgag ttattgtcat acttggagaa agcaaacaag    3840
tggctaaatg aagtagaatt taaacttaaa accactgaaa acattcctgg cggagctgag    3900
gaaatctctg aggtgctaga ttcacttgaa aatttgatgc acattcaga ggataaccca    3960 aatcagattc gcatattggc acagacccta acagatggcg gagtcatgga tgagctaatc    4020
aatgaggaac ttgagacatt taattctcgt tggagggaac tacatgaaga ggctgtaagg    4080
aggcaaaagt tgcttgaaca gagcatccag tctgcccagg agactgaaaa ttccttacac    4140
ttaatccagg agtccctcac attcattgac aagcagttgg cagcttatat tgcagacaag    4200
gtggacgcag ctcaaatgcc tcaggaagcc cagaaaatcc aatctgattt gacaagtcat    4260
gagatcagtt tagaagaaat gaagaaacat aatcagggga aggaggctgc ccaaagagtc    4320
ctgtctcaga ttgatgttgc acagaaaaaa ttacaagatg tctccatgaa gtttcgatta    4380
```

-continued

```
ttccagaaac cagccaattt tgagcagcgt ctacaagaaa gtaagatgat tttagatgaa    4440
gtgaagatgc acttgcctgc attggaaaca aagagtgtgg aacaggaagt agtacagtca    4500
cagctaaatc attgtgtgaa cttgtataaa agtctgagtg aagtgaagtc tgaagtggaa    4560
atggtgataa agactggacg tcagattgta cagaaaagc agacggaaaa tcccaaagaa     4620
cttgatgaaa gagtaacagc tttgaaattg cattataatg agctgggagc aaaggtaaca    4680
gaaagaaagc aacagttgga gaaatgcttg aaattgtccc gtaagatgcg aaaggaaatg    4740
aatgtcttga cagaatggct ggcagctaca gatatggaat tgacaaagag atcagcagtt    4800
gaaggaatgc ctagtaattt ggattctgaa gttgcctggg aaaggctac tcaaaaagag     4860 attgagaaac agaaggtgca cctgaagagt atcacagagg taggagaggc cttgaaaaca    4920
gttttgggca agaaggagac gttggtgaaa gataaactca gtcttctgaa tagtaattgg    4980
atagctgtca cctcccgagc agaagagtgg ttaaatcttt tgttggaata ccagaaacac    5040
atggaaactt tgaccagaa tgtggaccac atcacaaagt ggatcattca ggctgacaca     5100
cttttggatg aatcagagaa aagaaaccc cagcaaaaag aagacgtgct taagcgttta     5160
aaggcagaac tgaatgacat acgcccaaag gtggactcta cacgtgacca agcagcaaac    5220
ttgatggcaa accacggtga ccactgcagg aaattagtag agccccaaat ctcagagctc    5280
aaccatcgat ttgcagccat ttcacacaga attaagactg gaaaggcctc cattcctttg    5340
aaggaattgg agcagtttaa ctcagatata caaaaattgc ttgaaccact ggaggctgaa    5400
attcagcagg gggtgaatct gaaagaggaa gacttcaata agatatgaa tgaagacaat     5460 gagggtactg taaagaatt gttgcaaaga ggagacaact acaacaaag aatcacagat      5520 gagagaaaga gcgaggaaat aaagataaaa cagcagctgt tacagacaaa acataatgct    5580
ctcaaggatt tgaggtctca aagaagaaaa aaggctctag aaatttctca tcagtggtat    5640
cagtacaaga ggcaggctga tgatctcctg aaatgcttgg atgacattga aaaaaaatta    5700
gccagcctac ctgagcccag agatgaaagg aaaataaagg aaattgatcg ggaattgcag    5760
aagaagaaag aggagctgaa tgcagtgcgt aggcaagctg agggcttgtc tgaggatggg    5820
gccgcaatgg cagtggagcc aactcagatc cagctcagca agcgctggcg ggaaattgag    5880
agcaaatttg ctcagtttcg aagactcaac tttgcacaaa ttcacactgt ccgtgaagaa    5940
acgatgatgg tgatgactga agacatgcct ttggaaattt cttatgtgcc ttctacttat    6000
ttgactgaaa tcactcatgt ctcacaagcc ctattagaag tggaacaact tctcaatgct    6060
cctgacctct gtgctaagga ctttgaagat ctctttaagc aagaggagtc tctgaagaat    6120
ataaaagata gtctacaaca aagctcaggt cggattgaca ttattcatag caagaagaca    6180
gcagcattgc aaagtgcaac gcctgtggaa agggtgaagc tacaggaagc tctctcccag    6240
cttgatttcc aatgggaaaa agttaacaaa atgtacaagg accgacaagg gcgatttgac    6300
agatctgttg agaaatggcg gcgttttcat tatgatataa agatatttaa tcagtggcta    6360
acagaagctg aacagtttct cagaaagaca caaattcctg agaattggga acatgctaaa    6420
tacaaatggt atcttaagga actccaggat ggcattgggc agcggcaaac tgttgtcaga    6480
acattgaatg caactgggga agaaataatt cagcaatcct caaaaacaga tgccagtatt    6540
ctacaggaaa aattgggaag cctgaatctg cggtggcagg aggtctgcaa acagctgtca    6600
gacagaaaaa agaggctaga agaacaaaag aatatcttgt cagaatttca aagagattta    6660
aatgaatttt ttttatggtt ggaggaagca gataacattg ctagtatccc acttgaacct    6720
ggaaaagagc agcaactaaa agaaaagctt gagcaagtca agttactggt ggaagagttg    6780
```

```
cccctgcgcc agggaattct caaacaatta aatgaaactg gaggacccgt gcttgtaagt    6840
gctcccataa gcccagaaga gcaagataaa cttgaaaata agctcaagca gacaaatctc    6900
cagtggataa aggtttccag agctttacct gagaaacaag gagaaattga agctcaaata    6960
aaagaccttg ggcagcttga aaaaagctt gaagaccttg aagagcagtt aaatcatctg     7020
ctgctgtggt tatctcctat taggaatcag ttggaaattt ataaccaacc aaaccaagaa    7080
ggaccatttg acgttaagga aactgaaata gcagttcaag ctaaacaacc ggatgtggaa    7140
gagattttgt ctaaagggca gcatttgtac aaggaaaaac cagccactca gccagtgaag    7200
aggaagttag aagatctgag ctctgagtgg aaggcggtaa accgtttact tcaagagctg    7260
agggcaaagc agcctgacct agctcctgga ctgaccacta ttggagcctc tcctactcag    7320
actgttactc tggtgacaca acctgtggtt actaaggaaa ctgccatctc caaactagaa    7380
atgccatctt ccttgatgtt ggaggtacct gctctggcag atttcaaccg ggcttggaca    7440
gaacttaccg actggctttc tctgcttgat caagttataa aatcacagag ggtgatggtg    7500
ggtgaccttg aggatatcaa cgagatgatc atcaagcaga aggcaacaat gcaggatttg    7560
gaacagaggc gtccccagtt ggaagaactc attaccgctg cccaaaattt gaaaaacaag    7620
accagcaatc aagaggctag aacaatcatt acggatcgaa ttgaaagaat tcagaatcag    7680
tgggatgaag tacaagaaca ccttcagaac cggaggcaac agttgaatga aatgttaaag    7740
gattcaacac aatggctgga agctaaggaa gaagctgagc aggtcttagg acaggccaga    7800
gccaagcttg agtcatggaa ggagggtccc tatacagtag atgcaatcca aaagaaaatc    7860
acagaaacca agcagttggc caaagacctc cgccagtggc agacaaatgt agatgtggca    7920
aatgacttgg ccctgaaact tctccgggat tattctgcag atgataccag aaaagtccac    7980
atgataacag agaatatcaa tgcctcttgg agaagcattc ataaaagggt gagtgagcga    8040
gaggctgctt tggaagaaac tcatagatta ctgcaacagt tccccctgga cctgaaaaag    8100
tttcttgcct ggcttacaga agctgaaaca actgccaatg tcctacagga tgctacccgt    8160
aaggaaaggc tcctagaaga ctccaaggga gtaaagagc tgatgaaaca atggcaagac    8220
ctccaaggtg aaattgaagc tcacacagat gtttatcaca acctggatga aaacagccaa    8280
aaaatcctga tccctggaa aggttccgat gatgcagtcc tgttacaaag acgtttggat    8340
aacatgaact tcaagtggag tgaacttcgg aaaaagtctc tcaacattag gtcccatttg    8400
gaagccagtt ctgaccagtg gaagcgtctg cacctttctc tgcaggaact tctggtgtgg    8460
ctacagctga aagatgatga attaagccgg caggcaccta ttggaggcga cttttccagca   8520 gttcagaagc agaacgatgt acatagggcc ttcaagaggg aattgaaaac taaagaacct    8580
gtaatcatga gtactcttga gactgtacga atatttctga cagagcagcc tttggaagga    8640
ctagagaaac tctaccagga gcccagagag ctgcctcctg aggagagagc ccagaatgtc    8700
actcggcttc tacgaaagca ggctgaggag gtcaatactg agtgggaaaa attgaacctg    8760
cactccgctg actggcagag aaaaatagat gagacccttg aaagactcca ggaacttcaa    8820
gaggccacgg atgagctgga cctcaagctg cgccaagctg aggtgatcaa gggatcctgg    8880
cagcccgtgg gcgatctcct cattgactct ctccaagatc acctcgagaa agtcaaggca    8940
cttcgaggag aaattgcgcc tctgaaagag aacgtgagcc acgtcaatga ccttgctcgc    9000
cagcttacca ctttgggcat tcagctctca ccgtataacc tcagcactct ggaagacctg    9060
aacaccagat ggaagcttct gcaggtgccc gtcgaggacc gagtcaggca gctgcatgaa    9120
```

```
gcccacaggg actttggtcc agcatctcag cactttcttt ccacgtcgtg tccagggtccc    9180 tgggagagag ccatctcgcc aaacaaagtg ccctactata tcaaccacga gactcaaaca    9240
acttgctggg accatcccaa aatgacagag ctctaccagt ctttagctga cctgaataat    9300
gtcagattct cagcttatag gactgccatg aaactccgaa gactgcagaa ggcccctttgc   9360 ttggatctct tgagcctgtc agctgcatgt gatgccttgg accagcacaa cctcaagcaa    9420
aatgaccagc ccatggatat cctgcagatt attaattgtt tgaccactat ttatgaccgc    9480
ctggagcaag agcacaacaa tttggtcaac gtccctctct gcgtggatat gtgtctgaac    9540
tggctgctga atgtttatga tacgggacga acagggagga tccgtgtcct gtcttttaaa    9600
actggcatca tttccctgtg taaagcacat ttggaagaca agtacagata cctttttcaag   9660 caagtggcaa gttcaacagg attttgtgac cagcgcaggc tgggcctcct tctgcatgat    9720
tctatccaaa ttccaagaca gttgggtgaa gttgcatcct ttgggggcag taacattgag    9780
ccaagtgtcc ggagctgctt ccaatttgct aataataagc cagagatcga agcggccctc    9840
ttcctagact ggatgagact ggaaccccag tccatggtgt ggctgcccgt cctgcacaga    9900
gtggctgctg cagaaactgc caagcatcag gccaaatgta acatctgcaa agagtgtcca    9960
atcattggat tcaggtacag gagtctaaag cactttaatt atgacatctg ccaaagctgc   10020 ttttttttctg gtcgagttgc aaaaggccat aaaatgcact atcccatggt ggaatattgc   10080
actccgacta catcaggaga agatgttcga gactttgcca aggtactaaa aaacaaattt   10140
cgaaccaaaa ggtatttttgc gaagcatccc cgaatgggct acctgccagt gcagactgtc   10200
ttagaggggg acaacatgga aactcccgtt actctgatca acttctggcc agtagattct   10260
gcgcctgcct cgtcccctca gctttcacac gatgatactc attcacgcat tgaacattat   10320
gctagcaggc tagcagaaat ggaaaacagc aatggatctt atctaaatga tagcatctct   10380
cctaatgaga gcatagatga tgaacatttg ttaatccagc attactgcca aagtttgaac   10440
caggactccc ccctgagcca gcctcgtagt cctgcccaga tcttgatttc cttagagagt   10500
gaggaaagag gggagctaga gagaatccta gcagatcttg aggaagaaaa caggaatctg   10560
caagcagaat atgaccgtct aaagcagcag cacgaacata aaggcctgtc cccactgccg   10620 tccccctcctg aaatgatgcc cacctctccc cagagtcccc gggatgctga gctcattgct   10680
gaggccaagc tactgcgtca acacaaaggc cgcctggaag ccaggatgca aatcctggaa   10740
gaccacaata aacagctgga gtcacagtta cacaggctaa ggcagctgct ggagcaaccc   10800
caggcagagg ccaaagtgaa tggcacaacg gtgtcctctc cttctacctc tctacagagg   10860
tccgacagca gtcagcctat gctgctccga gtggttggca gtcaaacttc ggactccatg   10920
ggtgaggaag atcttctcag tcctccccag gacacaagca cagggttaga ggaggtgatg   10980
gagcaactca caactccctt ccctagttca agaggaagaa atacccctgg aaagccaatg   11040
agagaggaca caatgtag                                                 11058
```

<210> SEQ ID NO 2
<211> LENGTH: 4182
<212> TYPE: DNA
<213> ORGANISM: Homo sapiens

<400> SEQUENCE: 2

```
attttcacca tggtttggtg ggaagaagta gaggactgtt atgaaagaga agatgttcaa      60
aagaaaacat tcacaaaatg ggtaaatgca caatttttcta agtttgggaa gcagcatatt    120 gagaaacctct tcagtgacct acaggatggg aggcgcctcc tagacctcct cgaaggcctg    180
```

-continued

```
acagggcaaa aactgccaaa agaaaaagga tccacaagag ttcatgccct gaacaatgtc      240
aacaaggcac tgcgggtttt gcagaacaat aatgttgatt tagtgaatat tggaagtact      300
gacatcgtag atggaaatca taaactgact cttggtttga tttggaatat aatcctccac      360
tggcaggtca aaaatgtaat gaaaaatatc atggctggat tgcaacaaac caacagtgaa      420
aagattctcc tgagctgggt ccgacaatca actcgtaatt atccacaggt taatgtaatc      480
aacttcacca ccagctggtc tgatggcctg gctttgaatg ctctcatcca tagtcatagg      540
ccagacctat ttgactggaa tagtgtggtt tgccagcagt cagccacaca acgactggaa      600
catgcattca acatcgccag atatcaatta ggcatagaga aactactcga tcctgaagat      660
gttgatacca cctatccaga taagaagtcc atcttaatgt acatcacatc actcttccaa      720
gttttgcctc aacaagtgag cattgaagcc atccaggaag tggaaatgtt gccaaggcca      780
cctaaagtga ctaaagaaga acattttcag ttacatcatc aaatgcacta ttctcaacag      840
atcacggtca gtctagcaca gggatatgag agaacttctt cccctaagcc tcgattcaag      900
agctatgcct acacacaggc tgcttatgtc accacctctg accctacacg agcccatttt      960
ccttcacagc atttggaagc tcctgaagac aagtcatttg gcagttcatt gatggagagt     1020
gaagtaaacc tggaccgtta tcaaacagct ttagaagaag tattatcgtg gcttctttct     1080
gctgaggaca cattgcaagc acaaggagag atttctaatg atgtggaagt ggtgaaagac     1140
cagtttcata tctcatgaggg gtacatgatg gatttgacag cccatcaggg ccgggttggt     1200
aatattctac aattgggaag taagctgatt ggaacaggaa aattatcaga agatgaagaa     1260
actgaagtac aagagcagat gaatctccta aattcaagat gggaatgcct cagggtagct     1320
agcatggaaa acaaagcaa tttacataga gttttaatgg atctccagaa tcagaaactg      1380
aaagagttga atgactggct aacaaaaaca gaagaaagaa caaggaaaat ggaggaagag     1440
cctcttggac ctgatcttga agacctaaaa cgccaagtac aacaacataa ggtgcttcaa     1500
gaagatctag aacaagaaca agtcagggtc aattctctca ctcacatggt ggtggtagtt     1560
gatgaatcta gtggagatca cgcaactgct gctttggaag aacaacttaa ggtattggga     1620
gatcgatggg caaacatctg tagatggaca gaagaccgct gggttctttt acaagacatc     1680
cttctcaaat ggcaacgtct tactgaagaa cagtgccttt ttagtgcatg gctttcagaa     1740
aaagaagatg cagtgaacaa gattcacaca actggcttta aagatcaaaa tgaaatgtta     1800
tcaagtcttc aaaaactggc cgtttttaaaa gcggatctag aaaagaaaaa gcaatccatg     1860
ggcaaactgt attcactcaa acaagatctt cttttcaacac tgaagaataa gtcagtgacc     1920
cagaagacgg aagcatggct ggataacttt gcccggtgtt gggataattt agtccaaaaa     1980
cttgaaaaga gtacagcaca gactcataga ttactgcaac agttcccct ggacctggaa      2040 aagtttcttg cctggcttac agaagctgaa acaactgcca atgtcctaca ggatgctacc     2100
cgtaaggaaa ggctcctaga agactccaag ggagtaaaag agctgatgaa acaatggcaa     2160
gacctccaag gtgaaattga agctcacaca gatgtttatc acaacctgga tgaaaacagc     2220
caaaaaatcc tgagatccct ggaaggttcc gatgatgcag tcctgttaca aagacgtttg     2280
gataacatga acttcaagtg gagtgaactt cggaaaaagt ctctcaacat taggtcccat     2340
ttggaagcca gttctgacca gtggaagcgt ctgcaccttt ctctgcagga acttctggtg     2400
tggctacagc tgaaagatga tgaattaagc cggcaggcac ctattggagg cgactttcca     2460
gcagttcaga agcagaacga tgtacatagg gccttcaaga gggaattgaa aactaaagaa     2520
```

-continued

```
cctgtaatca tgagtactct tgagactgta cgaatatttc tgacagagca gcctttggaa      2580
ggactagaga aactctacca ggagcccaga gagctgcctc ctgaggagag agcccagaat      2640
gtcactcggc ttctacgaaa gcaggctgag gaggtcaata ctgagtggga aaaattgaac      2700
ctgcactccg ctgactggca gagaaaaata gatgagaccc ttgaaagact ccaggaactt      2760
caagaggcca cggatgagct ggacctcaag ctgcgccaag ctgaggtgat caagggatcc      2820
tggcagcccg tgggcgatct cctcattgac tctctccaag atcacctcga gaaagtcaag      2880
gcacttcgag gagaaattgc gcctctgaaa gagaacgtga gccacgtcaa tgaccttgct      2940
cgccagctta ccactttggg cattcagctc tcaccgtata acctcagcac tctggaagac      3000
ctgaacacca gatggaagct tctgcaggtg gccgtcgagg accgagtcag gcagctgcat      3060
gaagcccaca gggactttgg tccagcatct cagcactttc tttccacgtc tgtccagggt      3120
ccctgggaga gagccatctc gccaaacaaa gtgccctact atatcaacca cgagactcaa      3180
acaacttgct gggaccatcc caaaatgaca gagctctacc agtctttagc tgacctgaat      3240
aatgtcagat tctcagctta taggactgcc atgaaactcc gaagactgca gaaggccctt      3300
tgcttggatc tcttgagcct gtcagctgca tgtgatgcct tggaccagca caacctcaag      3360
caaaatgacc agcccatgga tatcctgcag attattaatt gtttgaccac tatttatgac      3420
cgcctggagc aagagcacaa caatttggtc aacgtccctc tctgcgtgga tatgtgtctg      3480
aactggctgc tgaatgttta tgatacggga cgaacaggga ggatccgtgt cctgtctttt      3540
aaaactggca tcatttccct gtgtaaagca catttggaag acaagtacag ataccttttc      3600
aagcaagtgg caagttcaac aggattttgt gaccagcgca ggctgggcct ccttctgcat      3660
gattctatcc aaattccaag acagttgggt gaagttgcat cctttggggg cagtaacatt      3720
gagccaagtg tccggagctg cttccaattt gctaataata agccagagat cgaagcggcc      3780
ctcttcctag actggatgag actggaaccc cagtccatgg tgtggctgcc cgtcctgcac      3840
agagtggctg ctgcagaaac tgccaagcat caggccaaat gtaacatctg caaagagtgt      3900
ccaatcattg gattcaggta caggagtcta aagcacttta attatgacat ctgccaaagc      3960 tgctttttttt ctggtcgagt tgcaaaaggc cataaaatgc actatcccat ggtggaatat      4020
tgcactccga ctacatcagg agaagatgtt cgagactttg ccaaggtact aaaaaacaaa      4080
tttcgaacca aaaggtattt tgcgaagcat ccccgaatgg gctacctgcc agtgcagact      4140
gtcttagagg gggacaacat ggaaactccc gacacaatgt ag                        4182
```

<210> SEQ ID NO 3
<211> LENGTH: 1991
<212> TYPE: DNA
<213> ORGANISM: Homo sapiens

<400> SEQUENCE: 3

```
atgctttggt gggaagaagt agaggactgt tatgaaagag aagatgttca aaagaaaaca       60
ttcacaaaat gggtaaatgc acaatttttct aagtttggga agcagcatat tgagaacctc     120
ttcagtgacc tacaggatgg gaggcgcctc ctagacctcc tcgaaggcct gacagggcaa      180
aaactgccaa agaaaaagg atccacaaga gttcatgccc tgaacaatgt caacaaggca      240
ctgcgggttt tgcagaacaa taatgttgat ttagtgaata ttggaagtac tgacatcgta      300
gatggaaatc ataaactgac tcttggtttg atttggaata atcctccact ctggcaggtc      360
aaaaatgtaa tgaaaatat catggctgga ttgcaaccaa ccaacagtga aaagattctc      420
ctgagctggg tccgacaatc aactcgtaat tatccacagg ttaatgtaat caacttcacc      480
```

-continued

```
accagctggt ctgatggcct ggctttgaat gctctcatcc atagtcatag gccagaccta      540
tttgactgga atagtgtggt ttgccagcag tcagccacac aacgactgga acatgcattc      600
aacatcgcca gatatcaatt aggcatagag aaactactcg atcctgaaga tgttgatacc      660
acctatccag ataagaagtc catcttaatg tacatcacat cactcttcca agttttgcct      720
caacaagtga gcattgaagc catccaggaa gtggaaatgt tgccaaggcc acctaaagtg      780
actaaagaag aacattttca gttacatcat caaatgcact attctcaaca gatcacggtc      840
agtctagcac agggatatga gagaacttct tcccctaagc ctcgattcaa gagctatgcc      900
tacacacagg ctgcttatgt caccacctct gaccctacac ggagcccatt tccttcacag      960
catttggaag ctcctgaaga caagtcattt ggcagttcat tgatggagag tgaagtaaac     1020
ctggaccgtt atcaaacagc tttagaagaa gtattatcgt ggcttctttc tgctgaggac     1080
acattgcaag cacaaggaga gatttctaat gatgtggaag tggtgaaaga ccagtttcat     1140
actcatgagg ggtacatgat ggatttgaca gcccatcagg gccgggttgg taatattcta     1200
caattgggaa gtaagctgat tggaacagga aaattatcag aagatgaaga aactgaagta     1260
caagagcaga tgaatctcct aaattcaaga tgggaatgcc tcagggtagc tagcatggaa     1320
aaacaaagca atttacatag agtttttaatg gatctccaga atcagaaact gaaagagttg     1380
aatgactggc taacaaaaac agaagaaaga acaaggaaaa tggaggaaga gcctcttgga     1440
cctgatcttg aagacctaaa acgccaagta caacaacata aggtgcttca agaagatcta     1500
gaacaagaac aagtcagggt caattctctc actcacatgg tggtggtagt tgatgaatct     1560
agtggagatc acgcaactgc tgctttggaa gaacaactta aggtattggg agatcgatgg     1620
gcaaacatct gtagatggac agaagaccgc tgggttcttt tacaagacat cctgctcaaa     1680
tggcaacgtc ttactgaaga acagtgcctt tttagtgcat ggctttcaga aaaagaagat     1740
gcagtgaaca agattcacac aactggcttt aaagatcaaa atgaaatgtt atcaagtctt     1800
caaaaactgg ccgtttttaaa agcggatcta gaaaagaaaa agcaatccat gggcaaactg     1860
tattcaatca aacaagatct tctttcaaca ctgaagaata agtcagtgac ccagaagacg     1920
gaagcatggc tggataactt tgcccggtgt tgggataatt tagtccaaaa acttgaaaag     1980
agtacagcac a                                                         1991
```

<210> SEQ ID NO 4
<211> LENGTH: 2169
<212> TYPE: DNA
<213> ORGANISM: Homo sapiens

<400> SEQUENCE: 4

```
aactcataga ttactgcaac agttcccccct ggacctggaa aagtttcttg cctggcttac       60
agaagctgaa acaactgcca atgtcctaca ggatgctacc cgtaaggaaa ggctcctaga      120
agactccaag ggagtaaaag agctgatgaa acaatggcaa gacctccaag gtgaaattga      180
agctcacaca gatgtttatc acaacctgga tgaaaacagc caaaaaatcc tgagatccct      240
ggaaggttcc gatgatgcag tcctgttaca aagacgtttg gataacatga acttcaagtg      300
gagtgaactt cggaaaaagt ctctcaacat taggtcccat ttggaagcca gttctgacca      360
gtggaagcgt ctgcaccttt tctctgcagga acttctggtg tggctacagc tgaaagatga      420
tgaattaagc cggcaggcac ctattggagg cgacttttcca gcagttcaga agcagaacga      480
tgtacatagg gccttcaaga gggaattgaa aactaaagaa cctgtaatca tgagtactct      540
```

-continued

```
tgagactgta cgaatatttc tgacagagca gcctttggaa ggactagaga aactctacca      600
ggagcccaga gagctgcctc ctgaggagag agcccagaat gtcactcggc ttctacgaaa      660
gcaggctgag gaggtcaata ctgagtggga aaaattgaac ctgcactccg ctgactggca      720
gagaaaaata gatgagaccc ttgaaagact ccaggaactt caagaggcca cggatgagct      780
ggacctcaag ctgcgccaag ctgaggtgat caagggatcc tggcagcccg tgggcgatct      840
cctcattgac tctctccaag atcacctcga gaaagtcaag gcacttcgag agaaaattgc      900
gcctctgaaa gagaacgtga gccacgtcaa tgaccttgct cgccagctta ccactttggg      960
cattcagctc tcaccgtata acctcagcac tctggaagca ctgaacacca gatgaaagct     1020
tctgcaggtg gccgtcgagg accgagtcag gcagctgcat gaagcccaca gggactttgg     1080
tccagcatct cagcactttc tttccacgtc tgtccagggt ccctgggaga gagccatctc     1140
gccaaacaaa gtgccctact atatcaacca cgagactcaa acaacttgct gggaccatcc     1200
caaaatgaca gagctctacc agtctttagc tgacctgaat aatgtcagat ctcagctta     1260 taggactgcc atgaaactcc gaagactgca gaaggccctt tgcttggatc tcttgagcct     1320
gtcagctgca tgtgatgcct tggaccagca caacctcaag caaaatgacc agcccatgga     1380
tatcctgcag attattaatt gtttgaccac tatttatgac cgcctggagc aagagcacaa     1440
caatttggtc aacgtccctc tctgcgtgga tatgtgtctg aactggctgc tgaatgttta     1500
tgatacggga cgaacaggga ggatccgtgt cctgtctttt aaaactggca tcatttccct     1560
gtgtaaagca catttggaag acaagtacag ataccttttc aagcaagtgg caagttcaac     1620
aggattttgt gaccagcgca ggctgggcct ccttctgcat gattctatcc aaattccaag     1680
acagttgggt gaagttgcat cctttggggg cagtaacatt gagccaagtg tccggagctg     1740
cttccaattt gctaataata agccagagat cgaagcggcc ctcttcctag actggatgag     1800
actggaaccc cagtccatgg tgtggctgcc cgtcctgcac agagtggctg ctgcagaaac     1860
tgccaagcat caggccaaat gtaacatctg caaagagtgt ccaatcattg gattcaggta     1920
caggagtcta aagcacttta attatgacat ctgccaaagc tgctttttt ctggtcgagt     1980 tgcaaaaggc cataaaatgc actatcccat ggtggaatat tgcactccga ctacatcagg     2040
agaagatgtt cgagactttg ccaaggtact aaaaaacaaa tttcgaacca aaaggtatt      2100 tgcgaagcat ccccgaatgg gctacctgcc agtgcagact gtcttagagg gggacaacat     2160
ggaaactcc                                                             2169
```

<210> SEQ ID NO 5
<211> LENGTH: 12
<212> TYPE: DNA
<213> ORGANISM: Homo sapiens

<400> SEQUENCE: 5

```
ggacacaatg ta                                                           12
```

<210> SEQ ID NO 6
<211> LENGTH: 3999
<212> TYPE: DNA
<213> ORGANISM: Homo sapiens

<400> SEQUENCE: 6

```
attttcacca tggtttggtg ggaagaagta gaggactgtt atgaaagaga agatgttcaa       60
aagaaaacat tcacaaaatg ggtaaatgca caatttctta agtttgggaa gcagcatatt      120 gagaaacctct tcagtgacct acaggatggg aggcgcctcc tagacctcct cgaaggcctg     180
```

```
acagggcaaa aactgccaaa agaaaaagga tccacaagag ttcatgccct gaacaatgtc    240
aacaaggcac tgcgggtttt gcagaacaat aatgttgatt tagtgaatat tggaagtact    300
gacatcgtag atggaaatca taaactgact cttggtttga tttggaatat aatcctccac    360
tggcaggtca aaaatgtaat gaaaaatatc atggctggat tgcaacaaac caacagtgaa    420
aagattctcc tgagctgggt ccgacaatca actcgtaatt atccacaggt taatgtaatc    480
aacttcacca ccagctggtc tgatggcctg gctttgaatg ctctcatcca tagtcatagg    540
ccagacctat ttgactggaa tagtgtggtt tgccagcagt cagccacaca acgactggaa    600
catgcattca acatcgccag atatcaatta ggcatagaga aactactcga tcctgaagat    660
gttgatacca cctatccaga taagaagtcc atcttaatgt acatcacatc actcttccaa    720
gttttgcctc aacaagtgag cattgaagcc atccaggaag tggaaatgtt gccaaggcca    780
cctaaagtga ctaaagaaga acattttcag ttacatcatc aaatgcacta ttctcaacag    840
atcacggtca gtctagcaca gggatatgag agaacttctt cccctaagcc tcgattcaag    900
agctatgcct acacacaggc tgcttatgtc accacctctg accctacacg agcccattt     960 ccttcacagc atttggaagc tcctgaagac aagtcatttg gcagttcatt gatggagagt   1020
gaagtaaacc tggaccgtta tcaaacagct ttagaagaag tattatcgtg gcttctttct   1080
gctgaggaca cattgcaagc acaaggagag atttctaatg atgtggaagt ggtgaaagac   1140
cagtttcata tcatgagggg gtacatgatg gatttgacag cccatcaggg ccgggttggt   1200
aatattctac aattgggaag taagctgatt ggaacaggaa aattatcaga agatgaagaa   1260
actgaagtac aagagcagat gaatctccta aattcaagat gggaatgcct cagggtagct   1320
agcatggaaa acaaagcaa tttacataga gttttaatgg atctccagaa tcagaaactg   1380
aaagagttga atgactggct aacaaaaaca gaagaaagaa caaggaaaat ggaggaagag   1440
cctcttggac ctgatcttga agacctaaaa cgccaagtac aacaacataa ggtgcttcaa   1500
gaagatctag aacaagaaca agtcagggtc aattctctca ctcacatggt ggtggtagtt   1560
gatgaatcta gtggagatca cgcaactgct gctttggaag aacaacttaa ggtattggga   1620
gatcgatggg caaacatctg tagatggaca gaagaccgct gggttctttt acaagaccag   1680
cctgacctag ctcctggact gaccactatt ggagcctctc ctactcagac tgttactctg   1740
gtgacacaac ctgtggttac taaggaaact gccatctcca aactagaaat gccatcttcc   1800
ttgatgttgg aggtacctac tcatagatta ctgcaacagt tcccctgga cctgaaaaag   1860 tttcttgcct ggcttacaga agctgaaaca actgccaatg tcctacagga tgctacccgt   1920
aaggaaaggc tcctagaaga ctccaaggga gtaaaagagc tgatgaaaca atggcaagac   1980
ctccaaggtg aaattgaagc tcacacagat gtttatcaca acctggatga aaacagccaa   2040
aaaatcctga gatccctgga aggttccgat gatgcagtcc tgttacaaag acgtttggat   2100
aacatgaact tcaagtggag tgaacttcgg aaaaagtctc tcaacattag gtcccatttg   2160
gaagccagtt ctgaccagtg gaagcgtctg cacctttctc tgcaggaact tctggtgtgg   2220
ctacagctga aagatgatga attaagccgg caggcaccta ttggaggcga ctttccagca   2280
gttcagaagc agaacgatgt acatagggcc ttcaagaggg aattgaaaac taaagaacct   2340
gtaatcatga gtactcttga gactgtacga atatttctga cagagcagcc tttggaagga   2400
ctagagaaac tctaccagga gcccagagag ctgcctcctg aggagagagc ccagaatgtc   2460
actcggcttc tacgaaagca ggctgaggag gtcaatactg agtgggaaaa attgaacctg   2520
```

-continued

```
cactccgctg actggcagag aaaaatagat gagacccttg aaagactcca ggaacttcaa      2580
gaggccacgg atgagctgga cctcaagctg cgccaagctg aggtgatcaa gggatcctgg      2640
cagcccgtgg gcgatctcct cattgactct ctccaagatc acctcgagaa agtcaaggca      2700
cttcgaggag aaattgcgcc tctgaaagag aacgtgagcc acgtcaatga ccttgctcgc      2760
cagcttacca ctttgggcat tcagctctca ccgtataacc tcagcactct ggaagacctg      2820
aacaccagat ggaagcttct gcaggtggcc gtcgaggacc gagtcaggca gctgcatgaa      2880
gcccacaggg actttggtcc agcatctcag cactttcttt ccacgtctgt ccagggtccc      2940
tgggagagag ccatctcgcc aaacaaagtg ccctactata tcaaccacga gactcaaaca      3000
acttgctggg accatcccaa aatgacagag ctctaccagt ctttagctga cctgaataat      3060
gtcagattct cagcttatag gactgccatg aaactccgaa gactgcagaa ggcccttgc       3120 ttggatctct tgagcctgtc agctgcatgt gatgccttgg accagcacaa cctcaagcaa      3180
aatgaccagc ccatggatat cctgcagatt attaattgtt tgaccactat ttatgaccgc      3240
ctggagcaag agcacaacaa tttggtcaac gtccctctct gcgtggatat gtgtctgaac      3300
tggctgctga atgtttatga tacgggacga acagggagga tccgtgtcct gtcttttaaa      3360
actggcatca tttccctgtg taaagcacat ttggaagaca agtacagata ccttttcaag      3420
caagtggcaa gttcaacagg attttgtgac cagcgcaggc tgggcctcct tctgcatgat      3480
tctatccaaa ttccaagaca gttgggtgaa gttgcatcct ttgggggcag taacattgag      3540
ccaagtgtcc ggagctgctt ccaatttgct aataataagc cagagatcga agcggccctc      3600
ttcctagact ggatgagact ggaaccccag tccatggtgt ggctgcccgt cctgcacaga      3660
gtggctgctg cagaaactgc caagcatcag gccaaatgta acatctgcaa agagtgtcca      3720
atcattggat tcaggtacag gagtctaaag cactttaatt atgacatctg ccaaagctgc      3780 ttttttttctg gtcgagttgc aaaaggccat aaaatgcact atcccatggt ggaatattgc      3840
actccgacta catcaggaga agatgttcga gactttgcca aggtactaaa aaacaaattt      3900
cgaaccaaaa ggtattttgc gaagcatccc cgaatgggct acctgccagt gcagactgtc      3960
ttagaggggg acaacatgga aactcccgac acaatgtag                            3999
```

<210> SEQ ID NO 7
<211> LENGTH: 1667
<212> TYPE: DNA
<213> ORGANISM: Homo sapiens

<400> SEQUENCE: 7

```
atgctttggt gggaagaagt agaggactgt tatgaaagag aagatgttca aaagaaaaca       60
ttcacaaaat gggtaaatgc acaattttct aagtttggga gcagcatat tgagaacctc       120 ttcagtgacc tacaggatgg gaggcgcctc ctagacctcc tcgaaggcct gacagggcaa      180
aaactgccaa agaaaaagg atccacaaga gttcatgccc tgaacaatgt caacaaggca       240
ctgcgggttt tgcagaacaa taatgttgat ttagtgaata ttggaagtac tgacatcgta      300
gatggaaatc ataaactgac tcttggtttg atttggaata taatcctcca ctggcaggtc      360
aaaaatgtaa tgaaaaatat catggctgga ttgcaaccaa ccaacagtga aaagattctc      420
ctgagctggg tccgacaatc aactcgtaat tatccacagg ttaatgtaat caacttcacc      480
accagctggt ctgatggcct ggctttgaat gctctcatcc atagtcatag gccagaccta      540
tttgactgga atagtgtggt ttgccagcag tcagccacac aacgactgga acatgcattc      600
aacatcgcca gatatcaatt aggcatagag aaactactcg atcctgaaga tgttgatacc      660
```

```
acctatccag ataagaagtc catcttaatg tacatcacat cactcttcca agttttgcct      720
caacaagtga gcattgaagc catccaggaa gtggaaatgt tgccaaggcc acctaaagtg      780
actaaagaag aacattttca gttacatcat caaatgcact attctcaaca gatcacggtc      840
agtctagcac agggatatga gagaacttct tcccctaagc ctcgattcaa gagctatgcc      900
tacacacagg ctgcttatgt caccacctct gaccctacac ggagcccatt tccttcacag      960
catttggaag ctcctgaaga caagtcattt ggcagttcat tgatggagag tgaagtaaac     1020
ctggaccgtt atcaaacagc tttagaagaa gtattatcgt ggcttctttc tgctgaggac     1080
acattgcaag cacaaggaga gatttctaat gatgtggaag tggtgaaaga ccagtttcat     1140
actcatgagg ggtacatgat ggatttgaca gcccatcagg gccgggttgg taatattcta     1200
caattgggaa gtaagctgat tggaacagga aaattatcag aagatgaaga aactgaagta     1260
caagagcaga tgaatctcct aaattcaaga tgggaatgcc tcagggtagc tagcatggaa     1320
aaacaaagca atttacatag agttttaatg gatctccaga atcagaaact gaaagagttg     1380
aatgactggc taacaaaaac agaagaaaga acaggaaaaa tggaggaaga gcctcttgga     1440
cctgatcttg aagacctaaa acgccaagta caacaacata aggtgcttca agaagatcta     1500
gaacaagaac aagtcagggt caattctctc actcacatgg tggtggtagt tgatgaatct     1560
agtggagatc acgcaactgc tgctttggaa gaacaactta aggtattggg agatcgatgg     1620
gcaaacatct gtagatggac agaagaccgc tgggttcttt tacaaga                   1667

<210> SEQ ID NO 8
<211> LENGTH: 147
<212> TYPE: DNA
<213> ORGANISM: Homo sapiens

<400> SEQUENCE: 8
ggcaaagcag cctgacctag ctcctggact gaccactatt ggagcctctc ctactcagac       60
tgttactctg gtgacacaac ctgtggttac taaggaaact gccatctcca aactagaaat      120
gccatcttcc ttgatgttgg aggtacc                                          147

<210> SEQ ID NO 9
<211> LENGTH: 3858
<212> TYPE: DNA
<213> ORGANISM: Homo sapiens

<400> SEQUENCE: 9
attttcacca tggtttggtg ggaagaagta gaggactgtt atgaaagaga agatgttcaa       60
aagaaaacat tcacaaaatg ggtaaatgca caatttttcta agtttgggaa gcagcatatt      120
gagaacctct tcagtgacct acaggatggg aggcgcctcc tagacctcct cgaaggcctg      180
acagggcaaa aactgccaaa agaaaaagga tccacaagag ttcatgccct gaacaatgtc      240
aacaaggcac tgcgggtttt gcagaacaat aatgttgatt tagtgaatat tggaagtact      300
gacatcgtag atgaaaatca taaactgact cttggtttga tttggaatat aatcctccac      360
tggcaggtca aaaatgtaat gaaaaatatc atggctggat tgcaacaaac caacagtgaa      420
aagattctcc tgagctgggt ccgacaatca actcgtaatt atccacaggt taatgtaatc      480
aacttcacca ccagctggtc tgatggcctg gctttgaatg ctctcatcca tagtcataggg     540 ccagacctat ttgactggaa tagtgtggtt tgccagcagt cagccacaca acgactggaa      600
catgcattca acatcgccag atatcaatta ggcatagaga aactactcga tcctgaagat      660
```

```
gttgatacca cctatccaga taagaagtcc atcttaatgt acatcacatc actcttccaa    720
gttttgcctc aacaagtgag cattgaagcc atccaggaag tggaaatgtt gccaaggcca    780
cctaaagtga ctaaagaaga acattttcag ttacatcatc aaatgcacta ttctcaacag    840
atcacggtca gtctagcaca gggatatgag agaacttctt cccctaagcc tcgattcaag    900
agctatgcct acacacaggc tgcttatgtc accacctctg accctacacg gagcccattt    960
ccttcacagc atttggaagc tcctgaagac aagtcatttg gcagttcatt gatggagagt   1020
gaagtaaacc tggaccgtta tcaaacagct ttagaagaag tattatcgtg gcttcttcct   1080
gctgaggaca cattgcaagc acaaggagag atttctaatg atgtggaagt ggtgaaagac   1140
cagtttcata ctcatgaggg gtacatgatg gatttgacag cccatcaggg ccgggttggt   1200
aatattctac aattgggaag taagctgatt ggaacaggaa aattatcaga agatgaagaa   1260
actgaagtac aagagcagat gaatctccta aattcaagat gggaatgcct cagggtagct   1320
agcatggaaa acaaagcaa tttacataga gtttttaatgg atctccagaa tcagaaactg   1380
aaagagttga atgactggct aacaaaaaca gaagaaagaa caaggaaaat ggaggaagag   1440
cctcttggac ctgatcttga agacctaaaa cgccaagtac aacaacataa ggtgcttcaa   1500
gaagatctag aacaagaaca agtcagggtc aattctctca ctcacatggt ggtggtagtt   1560
gatgaatcta gtggagatca cgcaactgct gcttttggaag aacaacttaa ggtattggga   1620
gatcgatggg caaacatctg tagatggaca gaagaccgct gggttctttt acaagacact   1680
catagattac tgcaacagtt ccccctggac ctggaaaagt ttcttgcctg cttacagaa    1740
gctgaaacaa ctgccaatgt cctacaggat gctacccgta aggaaaggct cctagaagac   1800
tccaagggag taaagagct gatgaaacaa tggcaagacc tccaaggtga aattgaagct   1860
cacacagatg tttatcacaa cctggatgaa acagccaaa aaatcctgag atccctggaa   1920
ggttccgatg atgcagtcct gttacaaaga cgtttggata acatgaactt caagtggagt   1980
gaacttcgga aaaagtctct caacattagg tcccatttgg aagccagttc tgaccagtgg   2040
aagcgtctgc acctttctct gcaggaactt ctggtgtggc tacagctgaa agatgatgaa   2100
ttaagccggc aggcacctat tggaggcgac ttttccagcag ttcagaagca gaacgatgta   2160
catagggcct tcaagaggga attgaaaact aaagaacctg taatcatgag tactcttgag   2220
actgtacgaa tatttctgac agagcagcct ttggaaggac tagagaaact ctaccaggag   2280
cccagagagc tgcctcctga ggagagagcc cagaatgtca ctcggcttct acgaaagcag   2340
gctgaggagg tcaatactga gtgggaaaaa ttgaacctgc actccgctga ctggcagaga   2400
aaaatagatg agaccttga aagactccag gaacttcaag aggccacgga tgagctggac   2460
ctcaagctgc gccaagctga ggtgatcaag ggatcctggc agcccgtggg cgatctcctc   2520
attgactctc tccaagatca cctcgagaaa gtcaaggcac ttcgaggaga aattgcgcct   2580
ctgaaagaga acgtgagcca cgtcaatgac cttgctcgcc agcttaccac tttgggcatt   2640
cagctctcac cgtataacct cagcactctg gaagacctga acaccagatg gaagcttctg   2700
caggtggccg tcgaggaccg agtcaggcag ctgcatgaag cccacaggga ctttggtcca   2760
gcatctcagc actttctttc cacgtctgtc cagggtccct gggagagagc catctcgcca   2820
aacaaagtgc cctactatat caaccacgag actcaaacaa cttgctggga ccatcccaaa   2880
atgacagagc tctaccagtc tttagctgac ctgaataatg tcagattctc agcttatagg   2940
actgccatga aactccgaag actgcagaag gccctttgct tggatctctt gagcctgtca   3000
gctgcatgtg atgccttgga ccagcacaac ctcaagcaaa atgaccagcc catggatatc   3060
```

```
ctgcagatta ttaattgttt gaccactatt tatgaccgcc tggagcaaga gcacaacaat    3120
ttggtcaacg tccctctctg cgtggatatg tgtctgaact ggctgctgaa tgtttatgat    3180
acgggacgaa cagggaggat ccgtgtcctg tcttttaaaa ctggcatcat ttccctgtgt    3240
aaagcacatt tggaagacaa gtacagatac cttttcaagc aagtggcaag ttcaacagga    3300
ttttgtgacc agcgcaggct gggcctcctt ctgcatgatt ctatccaaat tccaagacag    3360
ttgggtgaag ttgcatcctt tgggggcagt aacattgagc caagtgtccg gagctgcttc    3420
caatttgcta ataataagcc agagatcgaa gcggccctct tcctagactg gatgagactg    3480
gaaccccagt ccatggtgtg gctgcccgtc ctgcacagag tggctgctgc agaaactgcc    3540
aagcatcagg ccaaatgtaa catctgcaaa gagtgtccaa tcattggatt caggtacagg    3600
agtctaaagc actttaatta tgacatctgc caaagctgct ttttttctgg tcgagttgca    3660
aaaggccata aaatgcacta tcccatggtg gaatattgca ctccgactac atcaggagaa    3720
gatgttcgag actttgccaa ggtactaaaa acaaatttc gaaccaaaag gtattttgcg    3780
aagcatcccc gaatgggcta cctgccagtg cagactgtct tagaggggga caacatggaa    3840
actcccgaca caatgtag                                                 3858

<210> SEQ ID NO 10
<211> LENGTH: 3531
<212> TYPE: DNA
<213> ORGANISM: Homo sapiens

<400> SEQUENCE: 10
attttcacca tggtttggtg ggaagaagta gaggactgtt atgaaagaga agatgttcaa      60
aagaaaacat tcacaaaatg ggtaaatgca caatttttcta agtttgggaa gcagcatatt     120
gagaacctct tcagtgacct acaggatggg aggcgcctcc tagacctcct cgaaggcctg     180
acagggcaaa aactgccaaa agaaaaagga tccacaagag ttcatgccct gaacaatgtc     240
aacaaggcac tgcgggtttt gcagaacaat aatgttgatt tagtgaatat tggaagtact     300
gacatcgtag atggaaatca taaactgact cttggtttga tttggaatat aatcctccac     360
tggcaggtca aaaatgtaat gaaaaatatc atggctggat tgcaacaaac caacagtgaa     420
aagattctcc tgagctgggt ccgacaatca actcgtaatt atccacaggt taatgtaatc     480
aacttcacca ccagctggtc tgatggcctg gctttgaatg ctctcatcca tagtcatagg     540
ccagacctat ttgactggaa tagtgtggtt tgccagcagt cagccacaca acgactggaa     600
catgcattca acatcgccag atatcaatta ggcatagaga aactactcga tcctgaagat     660
gttgatacca cctatccaga taagaagtcc atcttaatgt acatcacatc actcttccaa     720
gttttgcctc aacaagtgag cattgaagcc atccaggaag tggaaatgtt gccaaggcca     780
cctaaagtga ctaaagaaga acattttcag ttacatcatc aaatgcacta ttctcaacag     840
atcacggtca gtctagcaca gggatatgag agaacttctt cccctaagcc tcgattcaag     900
agctatgcct acacacaggc tgcttatgtc accacctctg accctacacg agcccatttt     960
ccttcacagc atttggaagc tcctgaagac aagtcatttg gcagttcatt gatggagagt    1020
gaagtaaacc tggaccgtta tcaaacagct ttagaagaag tattatcgtg gcttctttct    1080
gctgaggaca cattgcaagc acaaggagag atttctaatg atgtggaagt ggtgaaagac    1140
cagtttcata tctcatgagg gtacatgatg gatttgacag cccatcaggg ccgggttggt    1200
aatattctac aattgggaag taagctgatt ggaacaggaa aattatcaga agatgaagaa    1260
```

-continued

```
actgaagtac aagagcagat gaatctccta aattcaagat gggaatgcct cagggtagct    1320
agcatggaaa aacaaagcaa tttacataga actcatagat tactgcaaca gttccccctg    1380
gacctggaaa agtttcttgc ctggcttaca aagctgaaa caactgccaa tgtcctacag     1440
gatgctaccc gtaaggaaag gctcctagaa gactccaagg gagtaaaaga gctgatgaaa    1500
caatggcaag acctccaagg tgaaattgaa gctcacacag atgtttatca caacctggat    1560
gaaaacagcc aaaaaatcct gagatccctg gaaggttccg atgatgcagt cctgttacaa    1620
agacgtttgg ataacatgaa cttcaagtgg agtgaacttc ggaaaaagtc tctcaacatt    1680
aggtcccatt tggaagccag ttctgaccag tggaagcgtc tgcacctttc tctgcaggaa    1740
cttctggtgt ggctacagct gaaagatgat gaattaagcc ggcaggcacc tattggaggc    1800
gactttccag cagttcagaa gcagaacgat gtacataggg ccttcaagag ggaattgaaa    1860
actaaagaac ctgtaatcat gagtactctt gagactgtac gaatatttct gacagagcag    1920
cctttggaag gactagagaa actctaccag gagcccagag agctgcctcc tgaggagaga    1980
gcccagaatg tcactcggct tctacgaaag caggctgagg aggtcaatac tgagtgggaa    2040
aaattgaacc tgcactccgc tgactggcag agaaaaatag atgagaccct tgaaagactc    2100
caggaacttc aagaggccac ggatgagctg gacctcaagc tgcgccaagc tgaggtgatc    2160
aagggatcct ggcagcccgt gggcgatctc ctcattgact ctctccaaga tcacctcgag    2220
aaagtcaagg cacttcgagg agaaattgcg cctctgaaag agaacgtgag ccacgtcaat    2280
gaccttgctc gccagcttac cactttgggc attcagctct caccgtataa cctcagcact    2340
ctggaagacc tgaacaccag atggaagctt ctgcaggtgg ccgtcgagga ccgagtcagg    2400
cagctgcatg aagcccacag ggactttggt ccagcatctc agcactttct tccacgtct    2460 gtccagggtc cctgggagag agccatctcg ccaaacaaag tgccctacta tatcaaccac    2520
gagactcaaa caacttgctg ggaccatccc aaaatgacag agctctacca gtctttagct    2580
gacctgaata atgtcagatt ctcagcttat aggactgcca tgaaactccg aagactgcag    2640
aaggcccttt gcttggatct cttgagcctg tcagctgcat gtgatgcctt ggaccagcac    2700
aacctcaagc aaaatgacca gcccatggat atcctgcaga ttattaattg tttgaccact    2760
atttatgacc gcctggagca agagcacaac aatttggtca acgtccctct ctgcgtggat    2820
atgtgtctga actggctgct gaatgtttat gatacgggac gaacagggag gatccgtgtc    2880
ctgtctttta aaactggcat catttccctg tgtaaagcac atttggaaga caagtacaga    2940
taccttttca gcaagtggc aagttcaaca ggattttgtg accagcgcag gctgggcctc    3000
cttctgcatg attctatcca aattccaaga cagttgggtg aagttgcatc ctttggggc    3060 agtaacattg agccaagtgt ccggagctgc ttccaatttg ctaataataa gccagagatc    3120
gaagcggccc tcttcctaga ctggatgaga ctggaacccc agtccatggt gtggctgccc    3180
gtcctgcaca gagtggctgc tgcagaaact gccaagcatc aggccaaatg taacatctgc    3240
aaagagtgtc caatcattgg attcaggtac aggagtctaa agcactttaa ttatgacatc    3300
tgccaaagct gctttttttc tggtcgagtt gcaaaaggcc ataaaatgca ctatcccatg    3360
gtggaatatt gcactccgac tacatcagga gaagatgttc gagactttgc caaggtacta    3420
aaaaacaaat ttcgaaccaa aaggtatttt gcgaagcatc cccgaatggg ctacctgcca    3480
gtgcagactg tcttagaggg ggacaacatg gaaactcccg acacaatgta g             3531
```

<210> SEQ ID NO 11
<211> LENGTH: 1340

```
<212> TYPE: DNA
<213> ORGANISM: Homo sapiens

<400> SEQUENCE: 11
atgctttggt gggaagaagt agaggactgt tatgaaagag aagatgttca aaagaaaaca      60
ttcacaaaat gggtaaatgc acaattttct aagtttggga agcagcatat tgagaacctc     120
ttcagtgacc tacaggatgg gaggcgcctc ctagacctcc tcgaaggcct gacagggcaa     180
aaactgccaa agaaaaagg atccacaaga gttcatgccc tgaacaatgt caacaaggca     240
ctgcgggttt tgcagaacaa taatgttgat ttagtgaata ttggaagtac tgacatcgta     300
gatggaaatc ataaactgac tcttggtttg atttggaata aatcctcca ctggcaggtc      360 aaaaatgtaa tgaaaatat catggctgga ttgcaaccaa ccaacagtga aaagattctc      420
ctgagctggg tccgacaatc aactcgtaat tatccacagg ttaatgtaat caacttcacc     480
accagctggt ctgatggcct ggctttgaat gctctcatcc atagtcatag gccagaccta     540
tttgactgga atagtgtggt ttgccagcag tcagccacac aacgactgga acatgcattc     600
aacatcgcca gatatcaatt aggcatagag aaactactcg atcctgaaga tgttgatacc     660
acctatccag ataagaagtc catcttaatg tacatcacat cactcttcca agttttgcct     720
caacaagtga gcattgaagc catccaggaa gtggaaatgt tgccaaggcc acctaaagtg     780
actaaagaag aacattttca gttacatcat caaatgcact attctcaaca gatcacggtc     840
agtctagcac agggatatga gagaacttct tcccctaagc ctcgattcaa gagctatgcc     900
tacacacagg ctgcttatgt caccacctct gaccctacac ggagcccatt tccttcacag     960
catttggaag ctcctgaaga caagtcattt ggcagttcat tgatggagag tgaagtaaac    1020
ctggaccgtt atcaaacagc tttagaagaa gtattatcgt ggcttctttc tgctgaggac    1080
acattgcaag cacaggagaa gatttctaat gatgtggaag tggtgaaaga ccagtttcat    1140
actcatgagg ggtacatgat ggatttgaca gcccatcagg gccgggttgg taatattcta    1200
caattgggaa gtaagctgat tggaacagga aaattatcag aagatgaaga aactgaagta    1260
caagagcaga tgaatctcct aaattcaaga tgggaatgcc tcagggtagc tagcatggaa    1320
aaacaaagca atttacatag                                                1340

<210> SEQ ID NO 12
<211> LENGTH: 3510
<212> TYPE: DNA
<213> ORGANISM: Homo sapiens

<400> SEQUENCE: 12
attttcacca tggtttggtg ggaagaagta gaggactgtt atgaaagaga agatgttcaa      60
aagaaaacat tcacaaaatg ggtaaatgca caattttcta agtttgggaa gcagcatatt     120
gagaacctct tcagtgacct acaggatggg aggcgcctcc tagacctcct cgaaggcctg     180
acagggcaaa aactgccaaa agaaaaagga tccacaagag ttcatgccct gaacaatgtc     240
aacaaggcac tgcgggtttt gcagaacaat aatgttgatt tagtgaatat tggaagtact     300
gacatcgtag atggaaatca taaactgact cttggtttga tttggaatat aatcctccac     360
tggcaggtca aaaatgtaat gaaaatatc atggctggat tgcaaacaaac caacagtgaa     420 aagattctcc tgagctgggt ccgacaatca actcgtaatt atccacaggt taatgtaatc     480
aacttcacca ccagctggtc tgatggcctg gctttgaatg ctctcatcca tagtcatagg     540
ccagacctat ttgactggaa tagtgtggtt tgccagcagt cagccacaca acgactggaa     600
```

```
catgcattca acatcgccag atatcaatta ggcatagaga aactactcga tcctgaagat    660
gttgatacca cctatccaga taagaagtcc atcttaatgt acatcacatc actcttccaa    720
gttttgcctc aacaagtgag cattgaagcc atccaggaag tggaaatgtt gccaaggcca    780
cctaaagtga ctaaagaaga acattttcag ttacatcatc aaatgcacta ttctcaacag    840
atcacggtca gtctagcaca gggatatgag agaacttctt cccctaagcc tcgattcaag    900
agctatgcct acacacaggc tgcttatgtc accacctctg accctacacg agcccattt     960
ccttcacagc atttggaagc tcctgaagac aagtcatttg gcagttcatt gatggagagt   1020
gaagtaaacc tggaccgtta tcaaacagct ttagaagaag tattatcgtg gcttcttct    1080
gctgaggaca cattgcaagc acaaggagag atttctaatg atgtggaagt ggtgaaagac   1140
cagtttcata ctcatgaggg gtacatgatg gatttgacag cccatcaggg ccgggttggt   1200
aatattctac aattgggaag taagctgatt ggaacaggaa aattatcaga agatgaagaa   1260
actgaagtac aagagcagat gaatctccta aattcaagat gggaatgcct cagggtagct   1320
agcatggaaa acaaagcaa tttacataga gttttaatgg atctccagaa tcagaaactg    1380
aaagagttga atgactggct aacaaaaaca gaagaaagaa caaggaaaat ggaggaagag   1440
cctcttggac ctgatcttga agacctaaaa cgccaagtac aacaacataa ggtgcttcaa   1500
gaagatctag aacaagaaca agtcagggtc aattctctca ctcacatggt ggtggtagtt   1560
gatgaatcta gtggagatca cgcaactgct gctttggaag aacaacttaa ggtattggga   1620
gatcgatggg caaacatctg tagatggaca gaagaccgct gggttctttt acaagacagt   1680
tctgaccagt ggaagcgtct gcacctttct ctgcaggaac ttctggtgtg gctacagctg   1740
aaagatgatg aattaagccg gcaggcacct attggaggcg actttccagc agttcagaag   1800
cagaacgatg tacatagggc cttcaagagg gaattgaaaa ctaaagaacc tgtaatcatg   1860
agtactcttg agactgtacg aatatttctc acagagcagc ttttggaagg actagagaaa   1920
ctctaccagg agcccagaga gctgcctcct gaggagagag cccagaatgt cactcggctt   1980
ctacgaaagc aggctgagga ggtcaatact gagtgggaaa aattgaacct gcactccgct   2040
gactggcaga gaaaaataga tgagaccctt gaaagactcc aggaacttca agaggccacg   2100
gatgagctgg acctcaagct gcgccaagct gaggtgatca agggatcctg gcagcccgtg   2160
ggcgatctcc tcattgactc tctccaagat cacctcgaga aagtcaaggc acttcgagga   2220
gaaattgcgc ctctgaaaga aacgtgagc cacgtcaatg accttgctcg ccagcttacc    2280
actttgggca ttcagctctc accgtataac ctcagcactc tggaagacct gaacaccaga   2340
tggaagcttc tgcaggtggc cgtcgaggac cgagtcaggc agctgcatga agcccacagg   2400
gactttggtc cagcatctca gcactttctt ccacgtctg tccagggtcc ctgggagaga    2460
gccatctcgc caaacaaagt gccctactat atcaaccacg agactcaaac aacttgctgg   2520
gaccatccca aaatgacaga gctctaccag tcttttagctg acctgaataa tgtcagattc   2580
tcagcttata ggactgccat gaaactccga agactgcaga aggcccttg cttggatctc    2640
ttgagcctgt cagctgcatg tgatgccttg gaccagcaca acctcaagca aaatgaccag   2700
cccatggata tcctgcagat tattaattgt ttgaccacta tttatgaccg cctggagcaa   2760
gagcacaaca atttggtcaa cgtccctctc tgcgtggata tgtgtctgaa ctggctgctg   2820
aatgtttatg atacgggacg aacagggagg atccgtgtcc tgtcttttaa aactggcatc   2880
atttccctgt gtaaagcaca tttggaagac aagtacagat acctttttcaa gcaagtggca    2940
agttcaacag gattttgtga ccagcgcagg ctgggcctcc ttctgcatga ttctatccaa   3000
```

| | |
|---|---|
| attccaagac agttgggtga agttgcatcc tttgggggca gtaacattga gccaagtgtc | 3060 |
| cggagctgct tccaatttgc taataataag ccagagatcg aagcggccct cttcctagac | 3120 |
| tggatgagac tggaacccca gtccatggtg tggctgcccg tcctgcacag agtggctgct | 3180 |
| gcagaaactg ccaagcatca ggccaaatgt aacatctgca aagagtgtcc aatcattgga | 3240 |
| ttcaggtaca ggagtctaaa gcactttaat tatgacatct gccaaagctg cttttttct | 3300 |
| ggtcgagttg caaaaggcca taaaatgcac tatcccatgg tggaatattg cactccgact | 3360 |
| acatcaggag aagatgttcg agactttgcc aaggtactaa aaacaaatt tcgaaccaaa | 3420 |
| aggtattttg cgaagcatcc ccgaatgggc tacctgccag tgcagactgt cttagagggg | 3480 |
| gacaacatgg aaactcccga cacaatgtag | 3510 |

<210> SEQ ID NO 13
<211> LENGTH: 1821
<212> TYPE: DNA
<213> ORGANISM: Homo sapiens

<400> SEQUENCE: 13

| | |
|---|---|
| cagttctgac cagtggaagc gtctgcacct ttctctgcag gaacttctgg tgtggctaca | 60 |
| gctgaaagat gatgaattaa gccggcaggc acctattgga ggcgactttc agcagttca | 120 |
| gaagcagaac gatgtacata gggccttcaa gagggaattg aaaactaaag aacctgtaat | 180 |
| catgagtact cttgagactg tacgaatatt tctgacagag cagcctttgg aaggactaga | 240 |
| gaaactctac caggagccca gagagctgcc tcctgaggag agagcccaga atgtcactcg | 300 |
| gcttctacga aagcaggctg aggaggtcaa tactgagtgg gaaaaattga acctgcactc | 360 |
| cgctgactgg cagagaaaaa tagatgagac ccttgaaaga ctccaggaac ttcaagaggc | 420 |
| cacggatgag ctggacctca agctgcgcca agctgaggtg atcaagggat cctggcagcc | 480 |
| cgtgggcgat ctcctcattg actctctcca agatcacctc gagaaagtca aggcacttcg | 540 |
| aggagaaatt gcgcctctga agagaacgt gagccacgtc aatgaccttg ctcgccagct | 600 |
| taccactttg ggcattcagc tctcaccgta taacctcagc actctggaag acctgaacac | 660 |
| cagatggaag cttctgcagg tggccgtcga ggaccgagtc aggcagctgc atgaagccca | 720 |
| cagggacttt ggtccagcat ctcagcactt tctttccacg tctgtccagg gtccctggga | 780 |
| gagagccatc tcgccaaaca aagtgcccta ctatatcaac cacgagactc aaacaacttg | 840 |
| ctgggaccat cccaaaatga cagagctcta ccagtctta gctgacctga ataatgtcag | 900 |
| attctcagct tataggactg ccatgaaaact ccgaagactg cagaaggccc tttgcttgga | 960 |
| tctcttgagc ctgtcagctg catgtgatgc cttggaccag cacaacctca gcaaaatga | 1020 |
| ccagcccatg gatatcctgc agattattaa ttgtttgacc actatttatg accgcctgga | 1080 |
| gcaagagcac aacaatttgg tcaacgtccc tctctgcgtg gatatgtgtc tgaactggct | 1140 |
| gctgaatgtt tatgatacgg gacgaacagg gaggatccgt gtcctgtctt ttaaaactgg | 1200 |
| catcatttcc ctgtgtaaag cacatttgga agacaagtac agatacccttt tcaagcaagt | 1260 |
| ggcaagttca acaggatttt gtgaccagcg caggctgggc ctccttctgc atgattctat | 1320 |
| ccaaattcca agacagttgg gtgaagttgc atcctttggg ggcagtaaca ttgagccaag | 1380 |
| tgtccggagc tgcttccaat ttgctaataa taagccagag atcgaagcgg ccctcttcct | 1440 |
| agactggatg agactggaac cccagtccat ggtgtggctg cccgtcctgc acagagtggc | 1500 |
| tgctgcagaa actgccaagc atcaggccaa atgtaacatc tgcaaagagt gtccaatcat | 1560 |

-continued

| | |
|---|---|
| tggattcagg tacaggagtc taaagcactt taattatgac atctgccaaa gctgctttt | 1620 |
| ttctggtcga gttgcaaaag gccataaaat gcactatccc atggtggaat attgcactcc | 1680 |
| gactacatca ggagaagatg ttcgagactt tgccaaggta ctaaaaaaca aatttcgaac | 1740 |
| caaaaggtat tttgcgaagc atccccgaat gggctacctg ccagtgcaga ctgtcttaga | 1800 |
| gggggacaac atggaaactc c | 1821 |

<210> SEQ ID NO 14
<211> LENGTH: 3446
<212> TYPE: DNA
<213> ORGANISM: Homo sapiens

<400> SEQUENCE: 14

| | |
|---|---|
| attttcacca tggtttggtg ggaagaagta gaggactgtt atgaaagaga agatgttcaa | 60 |
| aagaaaacat tcacaaaatg ggtaaatgca caattttcta agtttgggaa gcagcatatt | 120 |
| gagaacctct tcagtgacct acaggatggg aggcgcctcc tagacctcct cgaaggcctg | 180 |
| acagggcaaa aactgccaaa agaaaaagga tccacaagag ttcatgccct gaacaatgtc | 240 |
| aacaaggcac tgcgggtttt gcagaacaat aatgttgatt tagtgaatat tggaagtact | 300 |
| gacatcgtag atggaaatca taaactgact cttggtttga tttggaatat aatcctccac | 360 |
| tggcaggtca aaaatgtaat gaaaaatatc atggctggat gcaacaaac caacagtgaa | 420 |
| aagattctcc tgagctgggt ccgacaatca actcgtaatt atccacaggt taatgtaatc | 480 |
| aacttcacca ccagctggtc tgatggcctg gctttgaatg ctctcatcca tagtcatagg | 540 |
| ccagacctat ttgactggaa tagtgtggtt tgccagcagt cagccacaca acgactggaa | 600 |
| catgcattca acatcgccag atatcaatta ggcatagaga aactactcga tcctgaagat | 660 |
| gttgatacca cctatccaga taagaagtcc atcttaatgt acatcacatc actcttccaa | 720 |
| gttttgcctc aacaagtgag cattgaagcc atccaggaag tggaaatgtt gccaaggcca | 780 |
| cctaaagtga ctaaagaaga acattttcag ttacatcatc aaatgcacta ttctcaacag | 840 |
| atcacggtca gtctagcaca gggatatgag agaacttctt cccctaagcc tcgattcaag | 900 |
| agctatgcct acacacaggc tgcttatgtc accacctctg accctacacg gagcccattt | 960 |
| ccttcacagc atttggaagc tcctgaagac aagtcatttg cagttcatt gatggagagt | 1020 |
| gaagtaaaacc tggaccgtta tcaaacagct ttagaagaag tattatcgtg gcttcttttct | 1080 |
| gctgaggaca cattgcaagc acaaggagag attttctaatg atgtggaagt ggtgaaagac | 1140 |
| cagtttcata ctcatgaggg gtacatgatg gatttgacag cccatcaggg ccgggttggt | 1200 |
| aatattctac aattgggaag taagctgatt ggaacaggaa aattatcaga agatgaagaa | 1260 |
| actgaagtac aagagcagat gaatctccta aattcaagat gggaatgcct cagggtagct | 1320 |
| agcatggaaa aacaaagcaa tttacataga gttttaatgg atctccagaa tcgaaactga | 1380 |
| aagagttgaa tgactggcta acaaaaacag aagaaagaac aaggaaaatg gaggaagagc | 1440 |
| ctcttggacc tgatcttgaa gacctaaaaac gccaagtaca caacataag gtgcttcaag | 1500 |
| aagatctaga acaagaacaa gtcagggtca attctctcac tcacatggtg gtggtagttg | 1560 |
| atgaatctag tggagatcac gcaactgctg ctttggaaga acaacttaag gtattgggag | 1620 |
| atcgatgggc aaacatctgt agatggacag aagaccgctg ggttcttta caagacatcc | 1680 |
| ttctcaaatg gcaacgtctt actgaagaac agtgcctttt tagtgcatgg ctttcagaaa | 1740 |
| aagaagatgc agtgaacaag attcacacaa ctggctttaa agatcaaaat gaaatgttat | 1800 |
| caagtcttca aaaactggcc gttttaaaag cggatctaga aagaaaaag caatccatgg | 1860 |

| | |
|---|---:|
| gcaaactgta ttcactcaaa caagatcttc tttcaacact gaagaataag tcagtgaccc | 1920 |
| agaagacgga agcatggctg ataactttg cccggtgttg ggataattta gtccaaaaac | 1980 |
| ttgaaaagag tacagcacag acccttgaaa gactccagga acttcaagag gccacggatg | 2040 |
| agctggacct caagctgcgc caagctgagg tgatcaaggg atcctggcag cccgtgggcg | 2100 |
| atctcctcat tgactctctc caagatcacc tcgagaaagt caaggcactt cgaggagaaa | 2160 |
| ttgcgcctct gaaagagaac gtgagccacg tcaatgacct tgctcgccag cttaccactt | 2220 |
| tgggcattca gctctcaccg tataacctca gcactctgga agacctgaac accagatgga | 2280 |
| agcttctgca ggtggccgtc gaggaccgag tcaggcagct gcatgaagcc cacagggact | 2340 |
| tggtccagc atctcagcac tttctttcca cgtctgtcca gggtccctgg agagagcca | 2400 |
| tctcgccaaa caaagtgccc tactatatca accacgagac tcaaacaact tgctgggacc | 2460 |
| atcccaaaat gacagagctc taccagtctt tagctgacct gaataatgtc agattctcag | 2520 |
| cttataggac tgccatgaaa ctccgaagac tgcagaaggc cctttgcttg gatctcttga | 2580 |
| gcctgtcagc tgcatgtgat gccttggacc agcacaacct caagcaaaat gaccagccca | 2640 |
| tggatatcct gcagattatt aattgtttga ccactattta tgaccgcctg gagcaagagc | 2700 |
| acaacaattt ggtcaacgtc cctctctgcg tggatatgtg tctgaactgg ctgctgaatg | 2760 |
| tttatgatac gggacgaaca gggaggatcc gtgtcctgtc ttttaaaact ggcatcattt | 2820 |
| ccctgtgtaa agcacatttg aagacaagt acagatacct tttcaagcaa gtggcaagtt | 2880 |
| caacaggatt ttgtgaccag cgcaggctgg gcctccttct gcatgattct atccaaattc | 2940 |
| caagacagtt gggtgaagtt gcatcctttg ggggcagtaa cattgagcca agtgtccgga | 3000 |
| gctgcttcca atttgctaat aataagccag agatcgaagc ggccctcttc ctagactgga | 3060 |
| tgagactgga accccagtcc atggtgtggc tgcccgtcct gcacagagtg gctgctgcag | 3120 |
| aaactgccaa gcatcaggcc aaatgtaaca tctgcaaaga gtgtccaatc attggattca | 3180 |
| ggtacaggag tctaaagcac tttaattatg acatctgcca aagctgcttt ttttctggtc | 3240 |
| gagttgcaaa aggccataaa atgcactatc ccatggtgga atattgcact ccgactacat | 3300 |
| caggagaaga tgttcgagac tttgccaagg tactaaaaaa caaatttcga accaaaaggt | 3360 |
| attttgcgaa gcatccccga tgggctacc tgccagtgca gactgtctta gagggggaca | 3420 |
| acatggaaac tcccgacaca atgtag | 3446 |

<210> SEQ ID NO 15
<211> LENGTH: 1434
<212> TYPE: DNA
<213> ORGANISM: Homo sapiens

<400> SEQUENCE: 15

| | |
|---|---:|
| gacccttgaa agactccagg aacttcaaga ggccacggat gagctggacc tcaagctgcg | 60 |
| ccaagctgag gtgatcaagg gatcctggca gcccgtgggc gatctcctca ttgactctct | 120 |
| ccaagatcac ctcgagaaag tcaaggcact tcgaggagaa attgcgcctc tgaaagagaa | 180 |
| cgtgagccac gtcaatgacc ttgctcgcca gcttaccact ttgggcattc agctctcacc | 240 |
| gtataacctc agcactctgg aagacctgaa caccagatgg aagcttctgc aggtggccgt | 300 |
| cgaggaccga gtcaggcagc tgcatgaagc ccacagggac tttggtccag catctcagca | 360 |
| cttttctttcc acgtctgtcc agggtccctg gagagagcc atctcgccaa acaaagtgcc | 420 |
| ctactatatc aaccacgaga ctcaaacaac ttgctgggac catcccaaaa tgacagagct | 480 |

```
ctaccagtct ttagctgacc tgaataatgt cagattctca gcttatagga ctgccatgaa      540
actccgaaga ctgcagaagg ccctttgctt ggatctcttg agcctgtcag ctgcatgtga      600
tgccttggac cagcacaacc tcaagcaaaa tgaccagccc atggatatcc tgcagattat      660
taattgtttg accactattt atgaccgcct ggagcaagag cacaacaatt tggtcaacgt      720
ccctctctgc gtggatatgt gtctgaactg gctgctgaat gtttatgata cgggacgaac      780
agggaggatc cgtgtcctgt cttttaaaac tggcatcatt tccctgtgta aagcacattt      840
ggaagacaag tacagatacc ttttcaagca agtggcaagt tcaacaggat tttgtgacca      900
gcgcaggctg ggcctccttc tgcatgattc tatccaaatt ccaagacagt ggggtgaagt      960
tgcatccttt gggggcagta acattgagcc aagtgtccgg agctgcttcc aatttgctaa     1020
taataagcca gagatcgaag cggccctctt cctagactgg atgagactgg aaccccagtc     1080
catggtgtgg ctgcccgtcc tgcacagagt ggctgctgca gaaactgcca agcatcaggc     1140
caaatgtaac atctgcaaag agtgtccaat cattggattc aggtacagga gtctaaagca     1200
ctttaattat gacatctgcc aaagctgctt tttttctggt cgagttgcaa aaggccataa     1260
aatgcactat cccatggtgg aatattgcac tccgactaca tcaggagaag atgttcgaga     1320
ctttgccaag gtactaaaaa acaaatttcg aaccaaaagg tattttgcga agcatccccg     1380
aatgggctac ctgccagtgc agactgtctt agaggggac aacatggaaa ctcc            1434
```

<210> SEQ ID NO 16
<211> LENGTH: 28
<212> TYPE: DNA
<213> ORGANISM: Artificial Sequence
<220> FEATURE:
<223> OTHER INFORMATION: Synthetic Construct

<400> SEQUENCE: 16
attttcacca tggtttggtg ggaagaag                                           28

<210> SEQ ID NO 17
<211> LENGTH: 25
<212> TYPE: DNA
<213> ORGANISM: Artificial Sequence
<220> FEATURE:
<223> OTHER INFORMATION: Synthetic Construct

<400> SEQUENCE: 17
cagcctgacc tagctcctgg actga                                              25

<210> SEQ ID NO 18
<211> LENGTH: 25
<212> TYPE: DNA
<213> ORGANISM: Artificial Sequence
<220> FEATURE:
<223> OTHER INFORMATION: Synthetic Construct

<400> SEQUENCE: 18
actcatagat tactgcaaca gttcc                                              25

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
agttctgacc agtggaagcg                                                    20

```
<210> SEQ ID NO 20
<211> LENGTH: 22
<212> TYPE: DNA
<213> ORGANISM: Artificial Sequence
<220> FEATURE:
<223> OTHER INFORMATION: Synthetic Construct

<400> SEQUENCE: 20
acccttgaaa gactccagga ac                                             22

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
tctatgtaaa ttgctttgtt                                                20

<210> SEQ ID NO 22
<211> LENGTH: 25
<212> TYPE: DNA
<213> ORGANISM: Artificial Sequence
<220> FEATURE:
<223> OTHER INFORMATION: Synthetic Construct

<400> SEQUENCE: 22
gtcttgtaaa agaacccagc ggtct                                          25

<210> SEQ ID NO 23
<211> LENGTH: 25
<212> TYPE: DNA
<213> ORGANISM: Artificial Sequence
<220> FEATURE:
<223> OTHER INFORMATION: Synthetic Construct

<400> SEQUENCE: 23
ctgtgctgta ctcttttcaa gtttt                                          25

<210> SEQ ID NO 24
<211> LENGTH: 25
<212> TYPE: DNA
<213> ORGANISM: Artificial Sequence
<220> FEATURE:
<223> OTHER INFORMATION: Synthetic Construct

<400> SEQUENCE: 24
aggtacctcc aacatcaagg aagat                                          25

<210> SEQ ID NO 25
<211> LENGTH: 30
<212> TYPE: DNA
<213> ORGANISM: Artificial Sequence
<220> FEATURE:
<223> OTHER INFORMATION: Synthetic Construct

<400> SEQUENCE: 25
ctacattgtg tcgggagttt ccatgttgtc                                     30

<210> SEQ ID NO 26
<211> LENGTH: 955
<212> TYPE: DNA
<213> ORGANISM: Homo sapiens
```

<400> SEQUENCE: 26

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg      120
gccaactcca tcactagggg ttcctagatc agcttgcatg cccactacgg gtctaggctg     180
cccatgtaag gaggcaaggc ctggggacac ccgagatgcc tggttataat taacccagac    240
atgtggctgc ccccccccc caacacctg ctgcctgagc ctcaccccca cccggtgcc       300
tgggtcttag gctctgtaca ccatggagga gaagctcgct ctaaaaataa ccctgtccct    360
ggtggatccc ctgcatgccc aatcaaggct gtggggact gagggcaggc tgtaacaggc     420
ttggggggcca gggcttatac gtgcctggga ctcccaaagt attactgttc catgttcccg   480
gcgaagggcc agctgtcccc cgccagctag actcagcact tagtttagga accagtgagc    540
aagtcagccc ttggggcagc ccatacaagg ccatggggct gggcaagctg cacgcctggg    600
tccggggtgg gcacggtgcc cgggcaacga gctgaaagct catctgctct caggggcccc    660
tccctgggga cagcccctcc tggctagtca caccctgtag gctcctctat ataacccagg    720
ggcacagggg ctgcccccgg gtcactcgag aggcctaata aagagctcag atgcatcgat    780
cagagtgtgt tggttttttg tgtgagatct aggaacccct agtgatggag ttggccactc    840
cctctctgcg cgctcgctcg ctcactgagg ccgcccgggg aaagcccggg cgtcgggcga    900
cctttggtcg cccggcctca gtgagcgagc gagcgcgcag agagggagtg gccaa          955
```

<210> SEQ ID NO 27
<211> LENGTH: 5149
<212> TYPE: DNA
<213> ORGANISM: Homo sapiens

<400> SEQUENCE: 27

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg      120
gccaactcca tcactagggg ttcctagatc tgaattcgag cttgcatgcc cactacgggt     180
ctaggctgcc catgtaagga ggcaaggcct ggggacaccc gagatgcctg ttataatta     240
acccagacat gtggctgccc ccccccccc aacacctgct gcctgagcct caccccccacc    300
ccggtgcctg ggtcttaggc tctgtacacc atggaggaga agctcgctct aaaaataacc    360
ctgtccctgg tggatcccct gcatgcccaa tcaaggctgt ggggactga gggcaggctg     420
taacaggctt gggggccagg gcttatacgt gcctgggact cccaaagtat tactgttcca    480
tgttcccggc gaagggccag ctgtcccccg ccagctagac tcagcactta gtttaggaac   540
cagtgagcaa gtcagccctt ggggcagccc atacaaggcc atgggctgg gcaagctgca    600
cgcctgggtc cggggtgggc acggtgcccg ggcaacgagc tgaaagctca tctgctctca   660
ggggcccctc cctggggaca gcccctcctg gctagtcaca ccctgtaggc tcctctatat    720
aacccagggg cacaggggct gcccccgggt cactcgaatt ttcaccatgg tttggtggga    780
agaagtagag gactgttatg aaagagaaga tgttcaaaag aaaacattca caaatgggt    840
aaatgcacaa ttttctaagt ttgggaagca gcatattgag aacctcttca gtgacctaca    900
ggatgggagg cgcctcctag acctcctcga aggcctgaca gggcaaaaac tgccaaaga    960
aaaaggatcc acaagagttc atgccctgaa caatgtcaac aaggcactgc gggttttgca    1020
gaacaatatg ttgatttag tgaatattgg aagtactgac atcgtagatg gaatcataa      1080
actgactctt ggtttgattt ggaatataat cctccactgg caggtcaaaa atgtaatgaa    1140
```

-continued

```
aaatatcatg gctggattgc aacaaaccaa cagtgaaaag attctcctga gctgggtccg      1200
acaatcaact cgtaattatc cacaggttaa tgtaatcaac ttcaccacca gctggtctga      1260
tggcctggct ttgaatgctc tcatccatag tcataggcca gacctatttg actggaatag      1320
tgtggtttgc cagcagtcag ccacacaacg actggaacat gcattcaaca tcgccagata      1380
tcaattaggc atagagaaac tactcgatcc tgaagatgtt gataccacct atccagataa      1440
gaagtccatc ttaatgtaca tcacatcact cttccaagtt ttgcctcaac aagtgagcat      1500
tgaagccatc caggaagtgg aaatgttgcc aaggccacct aaagtgacta agaagaaca       1560
ttttcagtta catcatcaaa tgcactattc tcaacagatc acggtcagtc tagcacaggg      1620
atatgagaga acttcttccc ctaagcctcg attcaagagc tatgcctaca cacaggctgc      1680
ttatgtcacc acctctgacc ctacacggag cccatttcct tcacagcatt tggaagctcc      1740
tgaagacaag tcatttggca gttcattgat ggagagtgaa gtaaacctgg accgttatca      1800
aacagcttta gaagaagtat tatcgtggct tctttctgct gaggacacat tgcaagcaca      1860
aggagagatt tctaatgatg tggaagtggt gaaagaccag tttcatactc atgaggggta      1920
catgatggat ttgacagccc atcagggccg ggttggtaat attctacaat tgggaagtaa      1980
gctgattgga acaggaaaat tatcagaaga tgaagaaact gaagtacaag agcagatgaa      2040
tctcctaaat tcaagatggg aatgcctcag ggtagctagc atggaaaaac aaagcaattt      2100
acatagagtt ttaatggatc tccagaatca gaaactgaaa gagttgaatg actggctaac      2160
aaaaacagaa gaaagaacaa ggaaaatgga ggaagagcct cttggacctg atcttgaaga      2220
cctaaaacgc caagtacaac aacataaggt gcttcaagaa gatctagaac aagaacaagt      2280
cagggtcaat tctctcactc acatggtggt ggtagttgat gaatctagtg gagatcacgc      2340
aactgctgct ttggaagaac aacttaaggt attgggagat cgatgggcaa acatctgtag      2400
atggacagaa gaccgctggg ttcttttaca agacatcctt ctcaaatggc aacgtcttac      2460
tgaagaacag tgccttttta gtgcatggct ttcagaaaaa gaagatgcag tgaacaagat      2520
tcacacaact ggctttaaag atcaaaatga aatgttatca agtcttcaaa aactggccgt      2580
tttaaaagcg gatctagaaa agaaaaagca atccatgggc aaactgtatt cactcaaaca      2640
agatcttctt tcaacactga gaataagtc agtgacccag aagacggaag catggctgga      2700
taactttgcc cggtgttggg ataatttagt ccaaaaactt gaaaagagta cagcacagac      2760
tcatagatta ctgcaacagt tcccctgga cctggaaaag tttcttgcct ggcttacaga       2820
agctgaaaca actgccaatg tcctacagga tgctacccgt aaggaaaggc tcctagaaga      2880
ctccaaggga gtaaaagagc tgatgaaaca atggcaagac ctccaaggtg aaattgaagc      2940
tcacacagat gtttatcaca acctggatga aaacagccaa aaaatcctga gatccctgga      3000
aggttccgat gatgcagtcc tgttacaaag acgtttggat aacatgaact tcaagtggag      3060
tgaacttcgg aaaaagtctc tcaacattag gtcccatttg gaagccagtt ctgaccagtg      3120
gaagcgtctg caccttttctc tgcaggaact tctggtgtgg ctacagctga agatgatga     3180
attaagccgg caggcaccta ttggaggcga cttttccagca gttcagaagc agaacgatgt      3240
acataggcc ttcaagaggg aattgaaaac taaagaacct gtaatcatga gtactcttga       3300
gactgtacga atatttctga cagagcagcc tttggaagga ctagagaaac tctaccagga      3360
gcccagagag ctgcctcctg aggagagagc ccagaatgtc actcggcttc tacgaaagca      3420
ggctgaggag gtcaatactg agtgggaaaa attgaacctg cactccgctg actggcagag      3480
```

```
aaaaatagat gagacccttg aaagactcca ggaacttcaa gaggccacgg atgagctgga    3540
cctcaagctg cgccaagctg aggtgatcaa gggatcctgg cagcccgtgg gcgatctcct    3600
cattgactct ctccaagatc acctcgagaa agtcaaggca cttcgaggag aaattgcgcc    3660
tctgaaagag aacgtgagcc acgtcaatga ccttgctcgc cagcttacca ctttgggcat    3720
tcagctctca ccgtataacc tcagcactct ggaagacctg aacaccagat ggaagcttct    3780
gcaggtggcc gtcgaggacc gagtcaggca gctgcatgaa gcccacaggg actttggtcc    3840
agcatctcag cactttcttt ccacgtctgt ccagggtccc tgggagagag ccatctcgcc    3900
aaacaaagtg ccctactata tcaaccacga gactcaaaca acttgctggg accatcccaa    3960
aatgacagag ctctaccagt ctttagctga cctgaataat gtcagattct cagcttatag    4020
gactgccatg aaactccgaa gactgcagaa ggcccctttgc ttggatctct tgagcctgtc    4080
agctgcatgt gatgccttgg accagcacaa cctcaagcaa aatgaccagc ccatggatat    4140
cctgcagatt attaattgtt tgaccactat ttatgaccgc ctggagcaag agcacaacaa    4200
tttggtcaac gtccctctct gcgtggatat gtgtctgaac tggctgctga atgtttatga    4260
tacgggacga acaggagga tccgtgtcct gtcttttaaa actggcatca tttccctgtg    4320
taaagcacat ttggaagaca agtacagata ccttttcaag caagtggcaa gttcaacagg    4380
attttgtgac cagcgcaggc tgggcctcct tctgcatgat tctatccaaa ttccaagaca    4440
gttgggtgaa gttgcatcct ttgggggcag taacattgag ccaagtgtcc ggagctgctt    4500
ccaatttgct aataataagc cagagatcga agcggccctc ttcctagact ggatgagact    4560
ggaaccccag tccatggtgt ggctgcccgt cctgcacaga gtggctgctg cagaaactgc    4620
caagcatcag gccaaatgta acatctgcaa agagtgtcca atcattggat tcaggtacag    4680
gagtctaaag cactttaatt atgacatctg ccaaagctgc tttttttctg gtcgagttgc    4740
aaaaggccat aaaatgcact atcccatggt ggaatattgc actccgacta catcaggaga    4800
agatgttcga gactttgcca aggtactaaa aaacaaattt cgaaccaaaa ggtattttgc    4860
gaagcatccc cgaatgggct acctgccagt gcagactgtc ttagaggggg acaacatgga    4920
aactcccgac acaatgtagt cgagaggcct aataaagagc tcagatgcat cgatcagagt    4980
gtgttggttt tttgtgtgag atctaggaac ccctagtgat ggagttggcc actccctctc    5040
tgcgcgctcg ctcgctcact gaggccgccc gggcaaagcc cgggcgtcgg gcgacctttg    5100
gtcgcccggc ctcagtgagc gagcgagcgc gcagagaggg agtggccaa              5149
```

<210> SEQ ID NO 28
<211> LENGTH: 4966
<212> TYPE: DNA
<213> ORGANISM: Homo sapiens

<400> SEQUENCE: 28

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctagatc tgaattcgag cttgcatgcc cactacgggt     180
ctaggctgcc catgtaagga ggcaaggcct ggggacaccc gagatgcctg gttataatta     240
acccagacat gtggctgccc ccccccccc aacacctgct gcctgagcct cacccccacc     300
ccggtgcctg ggtcttaggc tctgtacacc atggaggaga agctcgctct aaaaataacc     360
ctgtccctgg tggatcccct gcatgcccaa tcaggctgt gggggactga ggcaggctg      420
taacaggctt gggggccagg gcttatacgt gcctgggact cccaaagtat tactgttcca     480
```

```
tgttcccggc gaagggccag ctgtcccccg ccagctagac tcagcactta gtttaggaac    540
cagtgagcaa gtcagccctt ggggcagccc atacaaggcc atgggctgg gcaagctgca    600
cgcctgggtc cggggtgggc acggtgcccg ggcaacgagc tgaaagctca tctgctctca    660
ggggcccctc cctggggaca gcccctcctg gctagtcaca ccctgtaggc tcctctatat    720
aacccagggg cacaggggct gccccgggt cactcgaatt ttcaccatgg tttggtggga    780
agaagtagag gactgttatg aaagagaaga tgttcaaaag aaaacattca caaaatgggt    840
aaatgcacaa ttttctaagt ttgggaagca gcatattgag aacctcttca gtgacctaca    900
ggatgggagg cgcctcctag acctcctcga aggcctgaca gggcaaaaac tgccaaaaga    960
aaaaggatcc acaagagttc atgccctgaa caatgtcaac aaggcactgc gggttttgca   1020
gaacaataat gttgatttag tgaatattgg aagtactgac atcgtagatg aaatcataa    1080
actgactctt ggtttgattt ggaatataat cctccactgg caggtcaaaa atgtaatgaa   1140
aaatatcatg gctggattgc aacaaaccaa cagtgaaaag attctcctga gctgggtccg   1200
acaatcaact cgtaattatc acaggttaa tgtaatcaac ttcaccacca gctggtctga   1260
tggcctggct ttgaatgctc tcatccatag tcataggcca gacctatttg actggaatag   1320
tgtggtttgc cagcagtcag ccacacaacg actggaacat gcattcaaca tcgccagata   1380
tcaattaggc atagagaaac tactcgatcc tgaagatgtt gataccacct atccagataa   1440
gaagtccatc ttaatgtaca tcacatcact cttccaagtt ttgcctcaac aagtgagcat   1500
tgaagccatc caggaagtgg aaatgttgcc aaggccacct aaagtgacta agaagaaca   1560
ttttcagtta catcatcaaa tgcactattc tcaacagatc acggtcagtc tagcacaggg   1620
atatgagaga acttcttccc ctaagcctcg attcaagagc tatgcctaca cacaggctgc   1680
ttatgtcacc acctctgacc ctacacggag cccatttcct tcacagcatt tggaagctcc   1740
tgaagacaag tcatttggca gttcattgat ggagagtgaa gtaaacctgg accgttatca   1800
aacagcttta gaagaagtat tatcgtggct tctttctgct gaggacacat tgcaagcaca   1860
aggagagatt tctaatgatg tggaagtggt gaaagaccag tttcatactc atgaggggta   1920
catgatggat ttgacagccc atcagggccg ggttggtaat attctacaat gggaagtaa    1980
gctgattgga acaggaaaat tatcagaaga tgaagaaact gaagtacaag agcagatgaa   2040
tctcctaaat tcaagatggg aatgcctcag ggtagctagc atggaaaaac aaagcaattt   2100
acatagagtt ttaatggatc tccagaatca gaaactgaaa gagttgaatg actggctaac   2160
aaaaacagaa gaaagaacaa ggaaaatgga ggaagagcct cttggacctg atcttgaaga   2220
cctaaaacgc caagtacaac aacataaggt gcttcaagaa gatctagaac aagaacaagt   2280
cagggtcaat tctctcactc acatggtggt ggtagttgat gaatctagtg gagatcacgc   2340
aactgctgct ttgaagaac aacttaaggt attgggagat cgatgggcaa acatctgtag   2400
atggacagaa gaccgctggg ttcttttaca agaccagcct gacctagctc ctggactgac   2460
cactattgga gcctctccta ctcagactgt tactctggtg acacaacctg tggttactaa   2520
ggaaactgcc atctccaaac tagaaatgcc atcttccttg atgttggagg tacctactca   2580
tagattactg caacagttcc ccctggacct ggaaaagttt cttgcctggc ttacagaagc   2640
tgaaacaact gccaatgtcc tacaggatgc tacccgtaag gaaaggctcc tagaagactc   2700
caagggagta aaaagagctga tgaaacaatg gcaagacctc aaggtgaaa ttgaagctca   2760
cacagatgtt tatcacaacc tggatgaaaa cagccaaaaa atcctgagat ccctggaagg   2820
```

```
ttccgatgat gcagtcctgt tacaaagacg tttggataac atgaacttca agtggagtga    2880
acttcggaaa aagtctctca acattaggtc ccatttggaa gccagttctg accagtggaa    2940
gcgtctgcac ctttctctgc aggaacttct ggtgtggcta cagctgaaag atgatgaatt    3000
aagccggcag gcacctattg gaggcgactt tccagcagtt cagaagcaga acgatgtaca    3060
tagggccttc aagagggaat tgaaaactaa agaacctgta atcatgagta ctcttgagac    3120
tgtacgaata tttctgacag agcagccttt ggaaggacta gagaaactct accaggagcc    3180
cagagagctg cctcctgagg agagagccca gaatgtcact cggcttctac gaaagcaggc    3240
tgaggaggtc aatactgagt gggaaaaatt gaacctgcac tccgctgact ggcagagaaa    3300
aatagatgag acccttgaaa gactccagga acttcaagag gccacggatg agctggacct    3360
caagctgcgc caagctgagg tgatcaaggg atcctggcag cccgtgggcg atctcctcat    3420
tgactctctc caagatcacc tcgagaaagt caaggcactt cgaggagaaa ttgcgcctct    3480
gaaagagaac gtgagccacg tcaatgacct tgctcgccag cttaccactt tgggcattca    3540
gctctcaccg tataacctca gcactctgga agacctgaac accagatgga agcttctgca    3600
ggtggccgtc gaggaccgag tcaggcagct gcatgaagcc cacagggact ttggtccagc    3660
atctcagcac tttctttcca cgtctgtcca gggtccctgg gagagagcca tctcgccaaa    3720
caaagtgccc tactatatca accacgagac tcaaacaact tgctgggacc atcccaaaat    3780
gacagagctc taccagtctt tagctgacct gaataatgtc agattctcag cttataggac    3840
tgccatgaaa ctccgaagac tgcagaaggc cctttgcttg gatctcttga gcctgtcagc    3900
tgcatgtgat gccttggacc agcacaacct caagcaaaat gaccagccca tggatatcct    3960
gcagattatt aattgtttga ccactatttt tgaccgcctg gagcaagagc acaacaattt    4020
ggtcaacgtc cctctctgcg tggatatgtg tctgaactgg ctgctgaatg tttatgatac    4080
gggacgaaca gggaggatcc gtgtcctgtc ttttaaaact ggcatcattt ccctgtgtaa    4140
agcacatttg gaagacaagt acagatacct tttcaagcaa gtggcaagtt caacaggatt    4200
ttgtgaccag cgcaggctgg gcctccttct gcatgattct atccaaattc aagacagtt    4260
gggtgaagtt gcatcctttg ggggcagtaa cattgagcca agtgtccgga gctgcttcca    4320
atttgctaat aataagccag agatcgaagc ggccctcttc ctagactgga tgagactgga    4380
accccagtcc atggtgtggc tgcccgtcct gcacagagtg gctgctgcag aaactgccaa    4440
gcatcaggcc aaatgtaaca tctgcaaaga gtgtccaatc attggattca ggtacaggag    4500
tctaaagcac tttaattatg acatctgcca aagctgcttt ttttctggtc gagttgcaaa    4560
aggccataaa atgcactatc ccatggtgga atattgcact ccgactacat caggagaaga    4620
tgttcgagac tttgccaagg tactaaaaaa caaatttcga accaaaaggt attttgcgaa    4680
gcatccccga atgggctacc tgccagtgca gactgtctta gagggggaca acatggaaac    4740
tcccgacaca atgtagtcga gaggcctaat aaagagctca gatgcatcga tcagagtgtg    4800
ttggttttttt gtgtgagatc taggaacccc tagtgatgga gttggccact ccctctctgc    4860
gcgctcgctc gctcactgag gccgcccggg caaagcccgg gcgtcgggcg acctttggtc    4920
gcccggcctc agtgagcgag cgagcgcgca gagagggagt ggccaa                   4966
```

<210> SEQ ID NO 29
<211> LENGTH: 4825
<212> TYPE: DNA
<213> ORGANISM: Homo sapiens

<400> SEQUENCE: 29

```
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcctagatc tgaattcgag cttgcatgcc cactacgggt   180
ctaggctgcc catgtaagga ggcaaggcct ggggacaccc gagatgcctg gttataatta   240
acccagacat gtggctgccc cccccccccc aacacctgct gcctgagcct caccccacc    300
ccggtgcctg ggtcttaggc tctgtacacc atggaggaga agctcgctct aaaaataacc   360
ctgtccctgg tggatcccct gcatgcccaa tcaaggctgt gggggactga gggcaggctg   420
taacaggctt gggggccagg gcttatacgt gcctgggact cccaaagtat tactgttcca   480
tgttcccggc gaagggccag ctgtcccccg ccagctagac tcagcactta gtttaggaac   540
cagtgagcaa gtcagccctt ggggcagccc atacaaggcc atgggctgg gcaagctgca   600
cgcctgggtc cggggtgggc acggtgcccg gcaacgagc tgaaagctca tctgctctca   660
ggggcccctc cctggggaca gcccctcctg gctagtcaca ccctgtaggc tcctctatat   720
aacccagggg cacaggggct gccccgggt cactcgaatt ttcaccatgg tttggtggga   780
agaagtagag gactgttatg aaagagaaga tgttcaaaag aaaacattca caaaatgggt   840
aaatgcacaa ttttctaagt ttgggaagca gcatattgag aacctcttca gtgacctaca   900
ggatgggagg cgcctcctag acctcctcga aggcctgaca gggcaaaaac tgccaaaaga   960
aaaaggatcc acaagagttc atgccctgaa caatgtcaac aaggcactgc gggttttgca  1020
gaacaataat gttgatttag tgaatattgg aagtactgac atcgtagatg aaatcataa   1080
actgactctt ggtttgattt ggaatataat cctccactgg caggtcaaaa atgtaatgaa  1140
aaatatcatg gctggattgc aacaaaccaa cagtgaaaag attctcctga ctgggtccg   1200
acaatcaact cgtaattatc cacaggttaa tgtaatcaac ttcaccacca gctggtctga  1260
tggcctggct ttgaatgctc tcatccatag tcataggcca gacctatttg actgaaatag  1320
tgtggtttgc cagcagtcag ccacacaacg actggaacat gcattcaaca tcgccagata  1380
tcaattaggc atagagaaac tactcgatcc tgaagatgtt gataccacct atccagataa  1440
gaagtccatc ttaatgtaca tcacatcact cttccaagtt ttgcctcaac aagtgagcat  1500
tgaagccatc caggaagtgg aaatgttgcc aaggccacct aaagtgacta agaagaaca   1560
tttttcagtta catcatcaaa tgcactattc tcaacagatc acggtcagtc tagcacaggg  1620
atatgagaga acttcttccc ctaagcctcg attcaagagc tatgcctaca cacaggctgc  1680
ttatgtcacc acctctgacc ctacacggag cccatttcct tcacagcatt tggaagctcc  1740
tgaagacaag tcatttggca gttcattgat ggagagtgaa gtaaacctgg accgttatca  1800
aacagcttta gaagaagtat tatcgtggct tctttctgct gaggacacat tgcaagcaca  1860
aggagagatt tctaatgatg tggaagtggt gaaagaccag tttcatactc atgagggta   1920
catgatggat ttgacagccc atcagggccg ggttggtaat attctacaat tgggaagtaa  1980
gctgattgga acaggaaaat tatcagaaga tgaagaaact gaagtacaag agcagatgaa  2040
tctcctaaat tcaagatggg aatgcctcag ggtagctagc atggaaaaac aaagcaattt  2100
acatagagtt ttaatggatc tccagaatca gaaactgaaa gagttgaatg actggctaac  2160
aaaaacagaa gaaagaacaa ggaaaatgga ggaagagcct cttggacctg atcttgaaga  2220
cctaaaacgc caagtacaac aacataaggt gcttcaagaa gatctagaac aagaacaagt  2280
cagggtcaat tctctcactc acatggtggt ggtagttgat gaatctagtg gagatcacgc  2340
```

```
aactgctgct ttggaagaac aacttaaggt attgggagat cgatgggcaa acatctgtag    2400
atggacagaa gaccgctggg ttcttttaca agacactcat agattactgc aacagttccc    2460
cctggacctg gaaaagtttc ttgcctggct tacagaagct gaaacaactg ccaatgtcct    2520
acaggatgct acccgtaagg aaaggctcct agaagactcc aagggagtaa aagagctgat    2580
gaaacaatgg caagacctcc aaggtgaaat tgaagctcac acagatgttt atcacaacct    2640
ggatgaaaac agccaaaaaa tcctgagatc cctggaaggt tccgatgatg cagtcctgtt    2700
acaaagacgt ttggataaca tgaacttcaa gtggagtgaa cttcggaaaa agtctctcaa    2760
cattaggtcc catttggaag ccagttctga ccagtggaag cgtctgcacc tttctctgca    2820
ggaacttctg gtgtggctac agctgaaaga tgatgaatta gccggcagg cacctattgg    2880 aggcgacttt ccagcagttc agaagcagaa cgatgtacat agggccttca gagggaatt    2940 gaaaactaaa gaacctgtaa tcatgagtac tcttgagact gtacgaatat ttctgacaga    3000
gcagcctttg gaaggactag agaaactcta ccaggagccc agagagctgc ctcctgagga    3060
gagagcccag aatgtcactc ggcttctacg aaagcaggct gaggaggtca atactgagtg    3120
ggaaaaattg aacctgcact ccgctgactg gcagagaaaa atagatgaga cccttgaaag    3180
actccaggaa cttcaagagg ccacggatga gctggacctc aagctgcgcc aagctgaggt    3240
gatcaaggga tcctggcagc ccgtgggcga tctcctcatt gactctctcc aagatcacct    3300
cgagaaagtc aaggcacttc gaggagaaat tgcgcctctg aaagagaacg tgagccacgt    3360
caatgacctt gctcgccagc ttaccacttt gggcattcag ctctcaccgt ataacctcag    3420
cactctggaa gacctgaaca ccagatggaa gcttctgcag gtggccgtcg aggaccgagt    3480
caggcagctg catgaagccc acagggactt tggtccagca tctcagcact ttcttttccac    3540 gtctgtccag ggtccctggg agagagccat ctcgccaaac aaagtgccct actatatcaa    3600
ccacgagact caaacaactt gctgggacca tcccaaaatg acagagctct accagtcttt    3660
agctgacctg aataatgtca gattctcagc ttataggact gccatgaaac tccgaagact    3720
gcagaaggcc ctttgcttgg atctcttgag cctgtcagct gcatgtgatg ccttggacca    3780
gcacaacctc aagcaaaatg accagcccat ggatatcctg cagattatta attgtttgac    3840
cactatttat gaccgcctgg agcaagagca caacaatttg gtcaacgtcc ctctctgcgt    3900
ggatatgtgt ctgaactggc tgctgaatgt ttatgatacg ggacgaacag ggaggatccg    3960
tgtcctgtct tttaaaactg gcatcatttc cctgtgtaaa gcacatttgg aagacaagta    4020
cagatacctt ttcaagcaag tggcaagttc aacaggattt tgtgaccagc gcaggctggg    4080
cctccttctg catgattcta tccaaattcc aagacagttg ggtgaagttg catcctttgg    4140
gggcagtaac attgagccaa gtgtccggag ctgcttccaa tttgctaata ataagccaga    4200
gatcgaagcg gccctcttcc tagactggat gagactggaa ccccagtcca tggtgtggct    4260 gccccgtcctg cacagagtgg ctgctgcaga aactgccaag catcaggcca aatgtaacat    4320
ctgcaaagag tgtccaatca ttggattcag gtacaggagt ctaaagcact ttaattatga    4380
catctgccaa agctgctttt tttctggtcg agttgcaaaa ggccataaaa tgcactatcc    4440
catggtggaa tattgcactc cgactacatc aggagaagat gttcgagact tgccaaggt    4500 actaaaaaac aaatttcgaa ccaaaaggta ttttgcgaag catccccgaa tgggctacct    4560
gccagtgcag actgtcttag aggggacaa catggaaact cccgacacaa tgtagtcgag    4620
aggcctaata aagagctcag atgcatcgat cagagtgtgt tggtttttg tgtgagatct    4680 aggaacccct agtgatggag ttggccactc cctctctgcg cgctcgctcg ctcactgagg    4740
```

```
ccgcccgggc aaagcccggg cgtcgggcga cctttggtcg cccggcctca gtgagcgagc    4800
gagcgcgcag agagggagtg gccaa                                         4825

<210> SEQ ID NO 30
<211> LENGTH: 4498
<212> TYPE: DNA
<213> ORGANISM: Homo sapiens

<400> SEQUENCE: 30
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctagatc tgaattcgag cttgcatgcc cactacgggt     180
ctaggctgcc catgtaagga ggcaaggcct ggggacaccc gagatgcctg gttataatta     240
acccagacat gtggctgccc cccccccccc aacacctgct gcctgagcct cacccccacc     300
ccggtgcctg ggtcttaggc tctgtacacc atggaggaga agctcgctct aaaaataacc     360
ctgtccctgg tggatcccct gcatgcccaa tcaaggctgt gggggactga ggcaggctg     420 taacaggctt gggggccagg gcttatacgt gcctgggact cccaaagtat tactgttcca     480
tgttcccggc aagggccag ctgtcccccg ccagctagac tcagcactta gtttaggaac      540
cagtgagcaa gtcagccctt ggggcagccc atacaaggcc atgggctgg gcaagctgca     600 cgcctgggtc cggggtgggc acggtgcccg ggcaacgagc tgaaagctca tctgctctca     660
ggggcccctc cctggggaca gcccctcctg gctagtcaca ccctgtaggc tcctctatat     720
aacccagggg cacaggggct gcccccgggt cactcgaatt ttcaccatgg tttggtggga     780
agaagtagag gactgttatg aaagagaaga tgttcaaaag aaaacattca caaaatgggt     840
aaatgcacaa ttttctaagt ttgggaagca gcatattgag aacctcttca gtgacctaca     900
ggatgggagg cgcctcctag acctcctcga aggcctgaca gggcaaaaac tgccaaaaga     960
aaaaggatcc acaagagttc atgccctgaa caatgtcaac aaggcactgc gggttttgca    1020
gaacaataat gttgatttag tgaatatttg aagtactgac atcgtagatg gaaatcataa    1080
actgactctt ggtttgattt ggaatataat cctccactgg caggtcaaaa atgtaatgaa    1140
aaatatcatg gctggattgc aacaaaccaa cagtgaaaag attctcctga ctgggtccg     1200 acaatcaact cgtaattatc cacaggttaa tgtaatcaac ttcaccacca gctggtctga    1260
tggcctggct tgaatgctc tcatccatag tcataggcca gacctatttg actggaatag     1320
tgtggtttgc cagcagtcag ccacacaacg actggaacat gcattcaaca tcgccagata    1380
tcaattaggc atagagaaac tactcgatcc tgaagatgtt gataccacct atccagataa    1440
gaagtccatc ttaatgtaca tcacatcact cttccaagtt ttgcctcaac aagtgagcat    1500
tgaagccatc caggaagtgg aaatgttgcc aaggccacct aaagtgacta agaagaaca     1560 ttttcagtta catcatcaaa tgcactattc tcaacagatc acggtcagtc tagcacaggg    1620
atatgagaga acttcttccc ctaagcctcg attcaagagc tatgcctaca cacaggctgc    1680
ttatgtcacc acctctgacc ctacacggag cccatttcct tcacagcatt ggaagctcc    1740 tgaagacaag tcatttggca gttcattgat ggagagtgaa gtaaacctgg accgttatca    1800
aacagcttta gaagaagtat tatcgtggct tctttctgct gaggacacat tgcaagcaca    1860
aggagagatt tctaatgatg tggaagtggt gaaagaccag tttcatactc atgagggta    1920 catgatggat ttgacagccc atcagggccg ggttggtaat attctacaat tgggaagtaa    1980
```

```
gctgattgga acaggaaaat tatcagaaga tgaagaaact gaagtacaag agcagatgaa    2040
tctcctaaat tcaagatggg aatgcctcag ggtagctagc atggaaaaac aaagcaattt    2100
acatagaact catagattac tgcaacagtt cccctggac  ctggaaaagt ttcttgcctg    2160
gcttacagaa gctgaaacaa ctgccaatgt cctacaggat gctacccgta aggaaaggct    2220
cctagaagac tccaagggag taaaagagct gatgaaacaa tggcaagacc tccaaggtga    2280
aattgaagct cacacagatg tttatcacaa cctggatgaa acagccaaa  aaatcctgag    2340 atccctggaa ggttccgatg atgcagtcct gttacaaaga cgtttggata acatgaactt    2400
caagtggagt gaacttcgga aaaagtctct caacattagg tcccatttgg aagccagttc    2460
tgaccagtgg aagcgtctgc accttctct  gcaggaactt ctggtgtggc tacagctgaa    2520
agatgatgaa ttaagccggc aggcacctat tggaggcgac tttccagcag ttcagaagca    2580
gaacgatgta catagggcct tcaagaggga attgaaaact aaagaacctg taatcatgag    2640
tactcttgag actgtacgaa tatttctgac agagcagcct ttggaaggac tagagaaact    2700
ctaccaggag cccagagagc tgcctcctga ggagagagcc cagaatgtca ctcggcttct    2760
acgaaagcag gctgaggagg tcaatactga gtgggaaaaa ttgaacctgc actccgctga    2820
ctggcagaga aaaatagatg agaccttga  aagactccag gaacttcaag aggccacgga    2880
tgagctggac ctcaagctgc gccaagctga ggtgatcaag ggatcctggc agcccgtggg    2940
cgatctcctc attgactctc tccaagatca cctcgagaaa gtcaaggcac ttcgaggaga    3000
aattgcgcct ctgaaagaga acgtgagcca cgtcaatgac cttgctcgcc agcttaccac    3060
tttgggcatt cagctctcac cgtataacct cagcactctg gaagacctga acaccagatg    3120
gaagcttctg caggtggccg tcgaggaccg agtcaggcag ctgcatgaag cccacaggga    3180
ctttggtcca gcatctcagc actttctttc cacgtctgtc cagggtccct gggagagagc    3240
catctcgcca aacaaagtgc cctactatat caaccacgag actcaaacaa cttgctggga    3300
ccatcccaaa atgacagagc tctaccagtc tttagctgac ctgaataatg tcagattctc    3360
agcttatagg actgccatga aactccgaag actgcagaag gccctttgct ggatctctt    3420 gagcctgtca gctgcatgtg atgccttgga ccagcacaac ctcaagcaaa atgaccagcc    3480
catggatatc ctgcagatta ttaattgttt gaccactatt tatgaccgcc tggagcaaga    3540
gcacaacaat ttggtcaacg tccctctctg cgtggatatg tgtctgaact ggctgctgaa    3600
tgtttatgat acgggacgaa cagggaggat ccgtgtcctg tctttaaaa  ctggcatcat    3660 ttccctgtgt aaagcacatt tggaagacaa gtacagatac cttttcaagc aagtggcaag    3720
ttcaacagga ttttgtgacc agcgcaggct gggcctcctt ctgcatgatt ctatccaaat    3780
tccaagacag ttgggtgaag ttgcatcctt tggggggcagt aacattgagc caagtgtccg    3840
gagctgcttc caatttgcta ataataagcc agagatcgaa gcggccctct cctagactg     3900 gatgagactg aaccccagt  ccatggtgtg gctgcccgtc ctgcacagag tggctgctgc    3960
agaaactgcc aagcatcagg ccaaatgtaa catctgcaaa gagtgtccaa tcattggatt    4020
caggtacagg agtctaaagc actttaatta tgacatctgc caaagctgct tttttctgg    4080 tcgagttgca aaaggccata aaatgcacta tcccatggtg aatattgca  ctccgactac    4140 atcaggagaa gatgttcgag actttgccaa ggtactaaaa aacaaatttc gaaccaaaag    4200
gtattttgcg aagcatcccc gaatgggcta cctgccagtg cagactgtct tagaggggga    4260
caacatggaa actcccgaca caatgtagtc gagaggccta ataaagagct cagatgcatc    4320
gatcagagtg tgttggtttt ttgtgtgaga tctaggaacc cctagtgatg gagttggcca    4380
```

```
ctccctctct gcgcgctcgc tcgctcactg aggccgcccg ggcaaagccc gggcgtcggg    4440
cgacctttgg tcgcccggcc tcagtgagcg agcgagcgcg cagagaggga gtggccaa      4498

<210> SEQ ID NO 31
<211> LENGTH: 4476
<212> TYPE: DNA
<213> ORGANISM: Homo sapiens

<400> SEQUENCE: 31
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctagatc tgaattcgag cttgcatgcc cactacgggt     180
ctaggctgcc catgtaagga ggcaaggcct ggggacaccc gagatgcctg gttataatta     240
acccagacat gtggctgccc cccccccccc aacacctgct gcctgagcct cacccccacc     300
ccggtgcctg ggtcttaggc tctgtacacc atggaggaga agctcgctct aaaaataacc     360
ctgtccctgg tggatcccct gcatgcccaa tcaaggctgt gggggactga ggcaggctg      420 taacaggctt gggggccagg gcttatacgt gcctgggact cccaaagtat tactgttcca     480
tgttcccggc aagggccag ctgtcccccg ccagctagac tcagcactta gtttaggaac      540
cagtgagcaa gtcagcccctt ggggcagccc atacaaggcc atgggctgg gcaagctgca     600 cgcctgggtc cggggtgggc acggtgcccg ggcaacgagc tgaaagctca tctgctctca     660
ggggcccctc cctggggaca gcccctcctg gctagtcaca ccctgtggct cctctatata     720 acccagggc acagggctg ccccccgggtc actcgaattt tcaccatggt ttggtgggaa       780
gaagtagagg actgttatga agagaagat gttcaaaaga aaacattcac aaaatgggta      840
aatgcacaat tttctaagtt tgggaagcag catattgaga acctcttcag tgacctacag     900
gatgggaggc gcctcctaga cctcctcgaa ggcctgacag gcaaaaaact gccaaaagaa     960
aaaggatcca caagagttca tgccctgaac aatgtcaaca aggcactgcg gttttgcag    1020 aacaataatg ttgatttagt gaatattgga agtactgaca tcgtagatgg aaatcataaa    1080
ctgactcttg gtttgatttg aatataatc ctccactggc aggtcaaaaa tgtaatgaaa     1140
aatatcatgg ctggattgca acaaaccaac agtgaaaaga ttctcctgag ctgggtccga    1200
caatcaactc gtaattatcc acaggttaat gtaatcaact tcaccaccag ctggtctgat    1260
ggcctggctt tgaatgctct catccatagt cataggccag acctatttga ctggaatagt    1320
gtggtttgcc agcagtcagc cacacaacga ctggaacatg cattcaacat cgccagatat    1380
caattaggca tagagaaact actcgatcct gaagatgttg ataccaccta tccagataag    1440
aagtccatct taatgtacat cacatcactc ttccaagttt tgcctcaaca agtgagcatt    1500
gaagccatcc aggaagtgga aatgttgcca aggccaccta agtgactaa agaagaacat     1560 tttcagttac atcatcaaat gcactattct caacagatca cggtcagtct agcacaggga    1620
tatgagagaa cttcttcccc taagcctcga ttcaagagct atgcctacac acaggctgct    1680
tatgtcacca cctctgaccc tacacggagc ccatttcctt cacagcattt ggaagctcct    1740
gaagacaagt catttggcag ttcattgatg gagagtgaag taaacctgga ccgttatcaa    1800
acagctttag aagaagtatt atcgtggctt ctttctgctg aggacacatt gcaagcacaa    1860
ggagagattt ctaatgatgt ggaagtggt aaagaccagt ttcatactca tgaggggtac     1920
atgatggatt tgacagccca tcaggccgg gttggtaata ttctacaatt gggaagtaag     1980
```

```
ctgattggaa caggaaaatt atcagaagat gaagaaactg aagtacaaga gcagatgaat   2040
ctcctaaatt caagatggga atgcctcagg gtagctagca tggaaaaaca aagcaattta   2100
catagagttt taatggatct ccagaatcag aaactgaaag agttgaatga ctggctaaca   2160
aaaacagaag aaagaacaag gaaaatggag gaagagcctc ttggacctga tcttgaagac   2220
ctaaaacgcc aagtacaaca acataaggtg cttcaagaag atctagaaca agaacaagtc   2280
agggtcaatt ctctcactca catggtggtg gtagttgatg aatctagtgg agatcacgca   2340
actgctgctt tggaagaaca acttaaggta ttgggagatc gatgggcaaa catctgtaga   2400
tggacagaag accgctgggt tcttttacaa gacagttctg accagtggaa gcgtctgcac   2460
ctttctctgc aggaacttct ggtgtggcta cagctgaaag atgatgaatt aagccggcag   2520
gcacctattg gaggcgactt tccagcagtt cagaagcaga acgatgtaca tagggccttc   2580
aagagggaat tgaaaactaa agaacctgta atcatgagta ctcttgagac tgtacgaata   2640
tttctgacag agcagccttt ggaaggacta gagaaactct accaggagcc cagagagctg   2700
cctcctgagg agagagccca gaatgtcact cggcttctac gaaagcaggc tgaggaggtc   2760
aatactgagt gggaaaaatt gaacctgcac tccgctgact ggcagagaaa aatagatgag   2820
acccttgaaa gactccagga acttcaagag gccacggatg agctggacct caagctgcgc   2880
caagctgagg tgatcaaggg atcctggcag cccgtgggcg atctcctcat tgactctctc   2940
caagatcacc tcgagaaagt caaggcactt cgaggagaaa ttgcgcctct gaaagagaac   3000
gtgagccacg tcaatgacct tgctcgccag cttaccactt tgggcattca gctctcaccg   3060
tataacctca gcactctgga agacctgaac accagatgga agcttctgca ggtggccgtc   3120
gaggaccgag tcaggcagct gcatgaagcc cacaggdact ttggtccagc atctcagcac   3180
tttcttccca cgtctgtcca gggtccctgg gagagagcca tctcgccaaa caaagtgccc   3240
tactatatca accacgagac tcaaacaact tgctgggacc atcccaaaat gacagagctc   3300
taccagtctt tagctgacct gaataatgtc agattctcag cttataggac tgccatgaaa   3360
ctccgaagac tgcagaaggc cctttgcttg gatctcttga gcctgtcagc tgcatgtgat   3420
gccttggacc agcacaacct caagcaaaat gaccagccca tggatatcct gcagattatt   3480
aattgtttga ccactattta tgaccgcctg gagcaagagc acaacaattt ggtcaacgtc   3540
cctctctgcg tggatatgtg tctgaactgg ctgctgaatg tttatgatac gggacgaaca   3600
gggaggatcc gtgtcctgtc ttttaaaact ggcatcattt ccctgtgtaa agcacatttg   3660
gaagacaagt acagatacct tttcaagcaa gtggcaagtt caacaggatt ttgtgaccag   3720
cgcaggctgg gcctccttct gcatgattct atccaaattc aagacagtt gggtgaagtt   3780 gcatcctttg ggggcagtaa cattgagcca agtgtccgga gctgcttcca atttgctaat   3840
aataagccag agatcgaagc ggccctcttc ctagactgga tgagactgga accccagtcc   3900
atggtgtggc tgcccgtcct gcacagagtg gctgctgcag aaactgccaa gcatcaggcc   3960
aaatgtaaca tctgcaaaga gtgtccaatc attggattca ggtacaggag tctaaagcac   4020
tttaattatg acatctgcca aagctgcttt tttctggtc gagttgcaaa aggccataaa   4080
atgcactatc ccatggtgga atattgcact ccgactacat caggagaaga tgttcgagac   4140
tttgccaagg tactaaaaaa caaatttcga accaaaaggt attttgcgaa gcatccccga   4200
atgggctacc tgccagtgca gactgtctta gaggggaca acatggaaac tcccgacaca   4260
atgtagtcga gaggcctaat aaagagctca gatgcatcga tcagagtgtg ttggtttttt   4320
gtgtgagatc taggaacccc tagtgatgga gttggccact ccctctctgc gcgctcgctc   4380
```

```
gctcactgag gccgcccggg caaagcccgg gcgtcgggcg acctttggtc gcccggcctc    4440
agtgagcgag cgagcgcgca gagagggagt ggccaa                              4476

<210> SEQ ID NO 32
<211> LENGTH: 4414
<212> TYPE: DNA
<213> ORGANISM: Homo sapiens

<400> SEQUENCE: 32
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctagatc tgaattcgag cttgcatgcc cactacgggt     180
ctaggctgcc catgtaagga ggcaaggcct ggggacaccc gagatgcctg gttataatta     240
acccagacat gtggctgccc cccccccccc aacacctgct gcctgagcct cacccccacc     300
ccggtgcctg ggtcttaggc tctgtacacc atggaggaga agctcgctct aaaaataacc     360
ctgtccctgg tggatcccct gcatgcccaa tcaaggctgt gggggactga ggcaggctg      420 taacaggctt gggggccagg gcttatacgt gcctgggact cccaaagtat tactgttcca     480
tgttcccggc aagggccag ctgtcccccg ccagctagac tcagcactta gtttaggaac      540
cagtgagcaa gtcagccctt ggggcagccc atacaaggcc atgggctgg gcaagctgca      600 cgcctgggtc cggggtgggc acggtgcccg ggcaacgagc tgaaagctca tctgctctca     660
ggggcccctc cctggggaca gcccctcctg gctagtcaca ccctgtaggc tcctctatat     720
aacccagggg cacaggggct gccccgggt cactcgaatt ttcaccatgg tttggtggga      780
agaagtagag gactgttatg aaagagaaga tgttcaaaag aaaacattca caaatgggt      840 aaatgcacaa ttttctaagt ttgggaagca gcatattgag aacctcttca gtgacctaca     900
ggatgggagg cgcctcctag acctcctcga aggcctgaca gggcaaaaac tgccaaaga      960 aaaaggatcc acaagagttc atgccctgaa caatgtcaac aaggcactgc gggttttgca    1020
gaacaataat gttgatttag tgaatattgg aagtactgac atcgtagatg gaaatcataa    1080
actgactctt ggtttgattt ggaatataat cctccactgg caggtcaaaa atgtaatgaa    1140
aaatatcatg gctggattgc aacaaaccaa cagtgaaaag attctcctga ctgggtccg    1200 acaatcaact cgtaattatc cacaggttaa tgtaatcaac ttcaccacca gctggtctga    1260
tggcctggct ttgaatgctc tcatccatag tcataggcca gacctatttg actgaaatag    1320
tgtggtttgc cagcagtcag ccacacaacg actggaacat gcattcaaca tcgccagata    1380
tcaattaggc atagagaaac tactcgatcc tgaagatgtt gataccacct atccagataa    1440
gaagtccatc ttaatgtaca tcacatcact cttccaagtt ttgcctcaac aagtgagcat    1500
tgaagccatc caggaagtgg aaatgttgcc aaggccacct aaagtgacta agaagaaca    1560 ttttcagtta catcatcaaa tgcactattc tcaacagatc acggtcagtc tagcacaggg    1620
atatgagaga acttcttccc ctaagcctcg attcaagagc tatgcctaca cacaggctgc    1680
ttatgtcacc acctctgacc ctacacggag cccatttcct tcacagcatt ggaagctcc     1740 tgaagacaag tcatttggca gttcattgat ggagagtgaa gtaaacctgg accgttatca    1800
aacagcttta gaagaagtat tatcgtggct tctttctgct gaggacacat tgcaagcaca    1860
aggagagatt tctaatgatg tggaagtggt gaaagaccag tttcatactc atgagggta    1920 catgatggat ttgacagccc atcagggccg ggttggtaat attctacaat tgggaagtaa    1980
```

```
gctgattgga acaggaaaat tatcagaaga tgaagaaact gaagtacaag agcagatgaa    2040
tctcctaaat tcaagatggg aatgcctcag ggtagctagc atggaaaaac aaagcaattt    2100
acatagagtt ttaatggatc tccagaatca gaaactgaaa gagttgaatg actggctaac    2160
aaaaacagaa gaaagaacaa ggaaaatgga ggaagagcct cttggacctg atcttgaaga    2220
cctaaaacgc caagtacaac aacataaggt gcttcaagaa gatctagaac aagaacaagt    2280
cagggtcaat tctctcactc acatggtggt ggtagttgat gaatctagtg gagatcacgc    2340
aactgctgct ttggaagaac aacttaaggt attgggagat cgatgggcaa acatctgtag    2400
atggacagaa gaccgctggg ttcttttaca agacatcctt ctcaaatggc aacgtcttac    2460
tgaagaacag tgccttttta gtgcatggct ttcagaaaaa gaagatgcag tgaacaagat    2520
tcacacaact ggctttaaag atcaaaatga aatgttatca agtcttcaaa aactggccgt    2580
tttaaaagcg gatctagaaa agaaaaagca atccatgggc aaactgtatt cactcaaaca    2640
agatcttctt tcaacactga gaataagtca agtgacccag aagacggaag catggctgga    2700
taactttgcc cggtgttggg ataatttagt ccaaaaactt gaaaagagta cagcacagac    2760
ccttgaaaga ctccaggaac ttcaagaggc cacggatgag ctggacctca agctgcgcca    2820
agctgaggtg atcaagggat cctggcagcc cgtgggcgat ctcctcattg actctctcca    2880
agatcacctc gagaaagtca aggcacttcg aggagaaatt gcgcctctga agagaacgt    2940 gagccacgtc aatgaccttg ctcgccagct taccactttg ggcattcagc tctcaccgta    3000
taacctcagc actctggaag acctgaacac cagatggaag cttctgcagg tggccgtcga    3060
ggaccgagtc aggcagctgc atgaagccca cagggacttt ggtccagcat ctcagcactt    3120
tctttccacg tctgtccagg gtccctggga gagagccatc tcgccaaaca aagtgcccta    3180
ctatatcaac cacgagactc aaacaacttg ctgggaccat cccaaaatga cagagctcta    3240
ccagtcttta gctgacctga ataatgtcag attctcagct tataggactg ccatgaaact    3300
ccgaagactg cagaaggccc tttgcttgga tctcttgagc ctgtcagctg catgtgatgc    3360
cttggaccag cacaacctca gcaaaaatga ccagcccatg gatatcctgc agattattaa    3420
ttgtttgacc actatttatg accgcctgga gcaagagcac aacaatttgg tcaacgtccc    3480
tctctgcgtg gatatgtgtc tgaactggct gctgaatgtt tatgatacgg acgaacagg    3540 gaggatccgt gtcctgtctt ttaaaactgg catcatttcc ctgtgtaaag cacatttgga    3600
agacaagtac agatacctt tcaagcaagt ggcaagttca acaggatttt gtgaccagcg    3660
caggctgggc ctccttctgc atgattctat ccaaattcca agacagttgg gtgaagttgc    3720
atcctttggg ggcagtaaca ttgagccaag tgtccggagc tgcttccaat ttgctaataa    3780
taagccagag atcgaagcgg ccctcttcct agactggatg agactggaac cccagtccat    3840
ggtgtggctg cccgtcctgc acagagtggc tgctgcagaa actgccaagc atcaggccaa    3900
atgtaacatc tgcaaagagt gtccaatcat ggattcagg tacaggagtc taaagcactt    3960
taattatgac atctgccaaa gctgcttttt ttctggtcga gttgcaaaag gccataaaat    4020
gcactatccc atggtggaat attgcactcc gactacatca ggagaagatg ttcgagactt    4080
tgccaaggta ctaaaaaaca aatttcgaac caaaaggtat tttgcgaagc atccccgaat    4140
gggctacctg ccagtgcaga ctgtcttaga ggggacaac atggaaactc ccgacacaat    4200
gtagtcgaga ggcctaataa agagctcaga tgcatcgatc agagtgtgtt ggttttttgt    4260
gtgagatcta ggaaccccta gtgatggagt tggccactcc ctctctgcgc gctcgctcgc    4320
tcactgaggc cgcccgggca agcccgggc gtcgggcgac cttggtcgc ccggcctcag    4380
```

```
tgagcgagcg agcgcgcaga gagggagtgg ccaa                                  4414

<210> SEQ ID NO 33
<211> LENGTH: 987
<212> TYPE: DNA
<213> ORGANISM: Homo sapiens

<400> SEQUENCE: 33
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctagatc tgaattcggt acccgttaca taacttacgg     180
taaatggccc gcctggctga ccgcccaacg accccgccc attgacgtca ataatgacgt      240
atgttcccat agtaacgcca atagggactt ccattgacg tcaatgggtg gagtatttac      300
ggtaaactgc ccacttggca gtacatcaag tgtatcatat gccaagtacg cccctattg      360 acgtcaatga cggtaaatgg cccgcctggc attatgccca gtacatgacc ttatgggact     420
ttcctacttg gcagtacatc tacgtattag tcatcgctat taccatggtg atgcggtttt     480
ggcagtacat caatgggcgt ggatagcggt ttgactcacg ggatttcca gtctccacc      540 ccattgacgt caatgggagt ttgttttggc accaaaatca acgggacttt ccaaaatgtc     600
gtaacaactc cgccccattg acgcaaatgg gcggtaggcg tgtacggtgg gaggtctata     660
taagcagagc tcgtttagtg aaccgtcaga tcgcctggag acgccatcca cgctgtttg      720 acctccatag aagacaccgg gaccgatcca gcctccggac tctagaggat ccggtactcg     780
agaggcctaa taagagctc agatgcatcg atcagagtgt gttggttttt tgtgtgagat     840
ctaggaaccc ctagtgatgg agttggccac tccctctctg cgcgctcgct cgctcactga     900
ggccgcccgg gcaaagcccg ggcgtcgggc gacctttggt cgcccggcct cagtgagcga     960
gcgagcgcgc agagagggag tggccaa                                         987

<210> SEQ ID NO 34
<211> LENGTH: 4990
<212> TYPE: DNA
<213> ORGANISM: Homo sapiens

<400> SEQUENCE: 34
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctagatc tgaattcggt acccgttaca taacttacgg     180
taaatggccc gcctggctga ccgcccaacg accccgccc attgacgtca ataatgacgt      240
atgttcccat agtaacgcca atagggactt ccattgacg tcaatgggtg gagtatttac      300
ggtaaactgc ccacttggca gtacatcaag tgtatcatat gccaagtacg cccctattg      360 acgtcaatga cggtaaatgg cccgcctggc attatgccca gtacatgacc ttatgggact     420
ttcctacttg gcagtacatc tacgtattag tcatcgctat taccatggtg atgcggtttt     480
ggcagtacat caatgggcgt ggatagcggt ttgactcacg ggatttcca gtctccacc      540 ccattgacgt caatgggagt ttgttttggc accaaaatca acgggacttt ccaaaatgtc     600
gtaacaactc cgccccattg acgcaaatgg gcggtaggcg tgtacggtgg gaggtctata     660
taagcagagc tcgtttagtg aaccgtcaga tcgcctggag acgccatcca cgctgtttg      720 acctccatag aagacaccgg gaccgatcca gcctccggac tctagaggat ccggtactcg     780
```

```
aattttcacc atggtttggt gggaagaagt agaggactgt tatgaaagag aagatgttca    840
aaagaaaaca ttcacaaaat gggtaaatgc acaattttct aagtttggga agcagcatat    900
tgagaacctc ttcagtgacc tacaggatgg gaggcgcctc ctagacctcc tcgaaggcct    960
gacagggcaa aaactgccaa agaaaaagg atccacaaga gttcatgccc tgaacaatgt   1020
caacaaggca ctgcgggttt tgcagaacaa taatgttgat ttagtgaata ttggaagtac   1080
tgacatcgta gatggaaatc ataaactgac tcttggtttg atttggaata taatcctcca   1140
ctggcaggtc aaaaatgtaa tgaaaaatat catggctgga ttgcaacaaa ccaacagtga   1200
aaagattctc ctgagctggg tccgacaatc aactcgtaat tatccacagg ttaatgtaat   1260
caacttcacc accagctggt ctgatggcct ggctttgaat gctctcatcc atagtcatag   1320
gccagaccta tttgactgga atagtgtggt ttgccagcag tcagccacac aacgactgga   1380
acatgcattc aacatcgcca gatatcaatt aggcatagag aaactactcg atcctgaaga   1440
tgttgatacc acctatccag ataagaagtc catcttaatg tacatcacat cactcttcca   1500
agttttgcct caacaagtga gcattgaagc catccaggaa gtggaaatgt tgccaaggcc   1560
acctaaagtg actaaagaag aacattttca gttacatcat caaatgcact attctcaaca   1620
gatcacggtc agtctagcac agggatatga gagaacttct tcccctaagc ctcgattcaa   1680
gagctatgcc tacacacagg ctgcttatgt caccacctct gacctacac ggagcccatt    1740
tccttcacag catttggaag ctcctgaaga caagtcattt ggcagttcat tgatggagag   1800
tgaagtaaac ctggaccgtt atcaaacagc tttagaagaa gtattatcgt ggcttctttc   1860
tgctgaggac acattgcaag cacaaggaga gatttctaat gatgtggaag tggtgaaaga   1920
ccagtttcat actcatgagg ggtacatgat ggatttgaca gcccatcagg gccgggttgg   1980
taatattcta caattgggaa gtaagctgat tggaacagga aaattatcag aagatgaaga   2040
aactgaagta caagagcaga tgaatctcct aaattcaaga tgggaatgcc tcagggtagc   2100
tagcatggaa aaacaaagca atttacatag agttttaatg gatctccaga atcagaaact   2160
gaaagagttg aatgactggc taacaaaaac agaagaaaga acaaggaaaa tggaggaaga   2220
gcctcttgga cctgatcttg aagacctaaa acgccaagta caacaacata aggtgcttca   2280
agaagatcta gaacaagaac aagtcagggt caattctctc actcacatgg tggtggtagt   2340
tgatgaatct agtggagatc acgcaactgc tgctttggaa gaacaactta aggtattggg   2400
agatcgatgg gcaaacatct gtagatggac agaagaccgc tgggttcttt tacaagacca   2460
gcctgaccta gctcctggac tgaccactat tggagcctct cctactcaga ctgttactct   2520
ggtgacacaa cctgtggtta ctaaggaaac tgccatctcc aaactagaaa tgccatcttc   2580
cttgatgttg gaggtaccta ctcatagatt actgcaacag ttcccctgg acctggaaaa    2640
gtttcttgcc tggcttacag aagctgaaac aactgccaat gtcctacagg atgctacccg   2700
taaggaaagg ctcctagaag actccaaggg agtaaaagag ctgatgaaac aatggcaaga   2760
cctccaaggt gaaattgaag ctcacacaga tgtttatcac aacctggatg aaaacagcca   2820
aaaaatcctg agatccctgg aaggttccga tgatgcagtc ctgttacaaa gacgtttgga   2880
taacatgaac ttcaagtgga gtgaacttcg gaaaagtct ctcaacatta ggtcccattt    2940
ggaagccagt tctgaccagt ggaagcgtct gcacctttct ctgcaggaac ttctggtgtg   3000
gctacagctg aaagatgatg aattaagccg gcaggcacct attggaggcg actttccagc   3060
agttcagaag cagaacgatg tacatagggc cttcaagagg gaattgaaaa ctaaagaacc   3120
tgtaatcatg agtactcttg agactgtacg aatatttctg acagagcagc ctttggaagg   3180
```

| | |
|---|---:|
| actagagaaa ctctaccagg agcccagaga gctgcctcct gaggagagag cccagaatgt | 3240 |
| cactcggctt ctacgaaagc aggctgagga ggtcaatact gagtgggaaa aattgaacct | 3300 |
| gcactccgct gactggcaga gaaaaataga tgagacccct gaaagactcc aggaacttca | 3360 |
| agaggccacg gatgagctgg acctcaagct gcgccaagct gaggtgatca agggatcctg | 3420 |
| gcagcccgtg ggcgatctcc tcattgactc tctccaagat cacctcgaga agtcaaggc | 3480 |
| acttcgagga gaaattgcgc ctctgaaaga gaacgtgagc cacgtcaatg accttgctcg | 3540 |
| ccagcttacc actttgggca ttcagctctc accgtataac ctcagcactc tggaagacct | 3600 |
| gaacaccaga tggaagcttc tgcaggtggc cgtcgaggac cgagtcaggc agctgcatga | 3660 |
| agcccacagg gactttggtc cagcatctca gcactttctt ccacgtctg tccagggtcc | 3720 |
| ctgggagaga gccatctcgc caaacaaagt gccctactat atcaaccacg agactcaaac | 3780 |
| aacttgctgg gaccatccca aaatgacaga gctctaccag tctttagctg acctgaataa | 3840 |
| tgtcagattc tcagcttata ggactgccat gaaactccga agactgcaga aggccctttg | 3900 |
| cttggatctc ttgagcctgt cagctgcatg tgatgccttg gaccagcaca acctcaagca | 3960 |
| aaatgaccag cccatggata tcctgcagat tattaattgt ttgaccacta tttatgaccg | 4020 |
| cctggagcaa gagcacaaca atttggtcaa cgtccctctc tgcgtggata tgtgtctgaa | 4080 |
| ctggctgctg aatgtttatg atacgggacg aacaggagg atccgtgtcc tgtcttttaa | 4140 |
| aactggcatc atttccctgt gtaaagcaca tttggaagac aagtacagat acctttcaa | 4200 |
| gcaagtggca agttcaacag gattttgtga ccagcgcagg ctgggcctcc ttctgcatga | 4260 |
| ttctatccaa attccaagac agttgggtga agttgcatcc tttgggggca gtaacattga | 4320 |
| gccaagtgtc cggagctgct tccaatttgc taataataag ccagagatcg aagcggccct | 4380 |
| cttcctagac tggatgagac tggaacccca gtccatggtg tggctgcccg tcctgcacag | 4440 |
| agtggctgct gcagaaactg ccaagcatca ggccaaatgt aacatctgca aagagtgtcc | 4500 |
| aatcattgga ttcaggtaca ggagtctaaa gcactttaat tatgacatct gccaaagctg | 4560 |
| ctttttttct ggtcgagttg caaaaggcca taaaatgcac tatcccatgg tggaatattg | 4620 |
| cactccgact acatcaggag aagatgttcg agactttgcc aaggtactaa aaaacaaatt | 4680 |
| tcgaaccaaa aggtattttg cgaagcatcc ccgaatgggc tacctgccag tgcagactgt | 4740 |
| cttagagggg gacaacatgg aaactcccga cacaatgtag tcgagaggcc taataaagag | 4800 |
| ctcagatgca tcgatcagag tgtgttggtt ttttgtgtga gatctaggaa cccctagtga | 4860 |
| tggagttggc cactccctct ctgcgcgctc gctcgctcac tgaggccgcc cgggcaaagc | 4920 |
| ccgggcgtcg ggcgaccttt ggtcgcccgg cctcagtgag cgagcgagcg cgcagagagg | 4980 |
| gagtggccaa | 4990 |

<210> SEQ ID NO 35
<211> LENGTH: 4848
<212> TYPE: DNA
<213> ORGANISM: Homo sapiens

<400> SEQUENCE: 35

| | |
|---|---:|
| tggccactcc ctctctgcgc gctcgctcgc tcactgaggc cgggcgacca aggtcgccc | 60 |
| gacgcccggg ctttgcccgg gcggcctcag tgagcgagcg agcgcgcaga gagggagtgg | 120 |
| ccaactccat cactagggt tcctagatct gaattcggta cccgttacat aacttacggt | 180 |
| aaatggcccg cctggctgac cgcccaacga ccccgccca ttgacgtcaa taatgacgta | 240 |

```
tgttcccata gtaacgccaa tagggacttt ccattgacgt caatgggtgg agtatttacg    300
gtaaactgcc cacttggcag tacatcaagt gtatcatatg ccaagtacgc cccctattga    360
cgtcaatgac ggtaaatggc ccgcctggca ttatgcccag tacatgacct tatgggactt    420
tcctacttgg cagtacatct acgtattagt catcgctatt accatggtga tgcggttttg    480
gcagtacatc aatgggcgtg gatagcggtt tgactcacgg ggatttccaa gtctccaccc    540
cattgacgtc aatgggagtt tgttttggca ccaaaatcaa cgggactttc caaaatgtcg    600
taacaactcc gccccattga cgcaaatggg cggtaggcgt gtacggtggg aggtctatat    660
aagcagagct cgtttagtga accgtcagat cgcctggaga cgccatccac gctgttttga    720
cctccataga agacaccggg accgatccag cctccggact ctagaggatc cggtactcga    780
attttcacca tggtttggtg ggaagaagta gaggactgtt atgaaagaga agatgttcaa    840
aagaaaacat tcacaaaatg ggtaaatgca caattttcta gtttgggaa gcagcatatt    900 gagaacctct tcagtgacct acaggatggg aggcgcctcc tagacctcct cgaaggcctg    960
acagggcaaa aactgccaaa agaaaaagga tccacaagag ttcatgccct gaacaatgtc   1020
aacaaggcac tgcgggtttt gcagaacaat aatgttgatt tagtgaatat tggaagtact   1080
gacatcgtag atggaaatca taaactgact cttggtttga tttggaatat aatcctccac   1140
tggcaggtca aaaatgtaat gaaaaatatc atggctggat tgcaacaaac caacagtgaa   1200
aagattctcc tgagctgggt ccgacaatca actcgtaatt atccacaggt taatgtaatc   1260
aacttcacca ccagctggtc tgatggcctg gctttgaatg ctctcatcca tagtcatagg   1320
ccagacctat ttgactggaa tagtgtggtt tgccagcagt cagccacaca acgactggaa   1380
catgcattca acatcgccag atatcaatta ggcatagaga aactactcga tcctgaagat   1440
gttgatacca cctatccaga taagaagtcc atcttaatgt acatcacatc actcttccaa   1500
gttttgcctc aacaagtgag cattgaagcc atccaggaag tggaaatgtt gccaaggcca   1560
cctaaagtga ctaaagaaga acattttcag ttacatcatc aaatgcacta ttctcaacag   1620
atcacggtca gtctagcaca gggatatgag agaacttctt cccctaagcc tcgattcaag   1680
agctatgcct acacacaggc tgcttatgtc accacctctg accctacacg gagcccattt   1740
ccttcacagc atttggaagc tcctgaagac aagtcatttg gcagttcatt gatggagagt   1800
gaagtaaacc tggaccgtta tcaaacagct ttagaagaag tattatcgtg gcttctttct   1860
gctgaggaca cattgcaagc acaaggagag atttctaatg atgtggaagt ggtgaaagac   1920
cagtttcata ctcatgaggg gtacatgatg gatttgacag cccatcaggg ccgggttggt   1980
aatattctac aattgggaag taagctgatt ggaacaggaa aattatcaga agatgaagaa   2040
actgaagtac aagagcagat gaatctccta aattcaagat gggaatgcct cagggtagct   2100
agcatggaaa acaaagcaa tttacataga gttttaatgg atctccagaa tcagaaactg   2160
aaagagttga atgactggct aacaaaaaca gaagaaagaa caaggaaaat ggaggaagag   2220
cctcttggac ctgatcttga agacctaaaa cgccaagtac aacaacataa ggtgcttcaa    2280
gaagatctag aacaagaaca agtcagggtc aattctctca ctcacatggt ggtggtagtt   2340
gatgaatcta gtggagatca cgcaactgct gctttggaag aacaacttaa ggtattggga   2400
gatcgatggg caaacatctg tagatggaca gaagaccgct gggttctttt acaagacact   2460
catagattac tgcaacagtt cccccctgga ctggaaaagt ttcttgcctg gcttacagaa   2520
gctgaaacaa ctgccaatgt cctacaggat gctacccgta aggaaggct cctagaagac   2580 tccaagggag taaaagagct gatgaaacaa tggcaagacc tccaaggtga aattgaagct   2640
```

```
cacacagatg tttatcacaa cctggatgaa aacagccaaa aaatcctgag atccctggaa    2700
ggttccgatg atgcagtcct gttacaaaga cgtttggata acatgaactt caagtggagt    2760
gaacttcgga aaaagtctct caacattagg tcccatttgg aagccagttc tgaccagtgg    2820
aagcgtctgc acctttctct gcaggaactt ctggtgtggc tacagctgaa agatgatgaa    2880
ttaagccggc aggcacctat tggaggcgac tttccagcag ttcagaagca gaacgatgta    2940
catagggcct tcaagaggga attgaaaact aaagaacctg taatcatgag tactcttgag    3000
actgtacgaa tatttctgac agagcagcct ttggaaggac tagagaaact ctaccaggag    3060
cccagagagc tgcctcctga ggagagagcc agaatgtca ctcggcttct acgaaagcag    3120
gctgaggagg tcaatactga gtgggaaaaa ttgaacctgc actccgctga ctggcagaga    3180
aaaatagatg agacccttga aagactccag gaacttcaag aggccacgga tgagctggac    3240
ctcaagctgc gccaagctga ggtgatcaag ggatcctggc agcccgtggg cgatctcctc    3300
attgactctc tccaagatca cctcgagaaa gtcaaggcac ttcgaggaga aattgcgcct    3360
ctgaaagaga acgtgagcca cgtcaatgac cttgctcgcc agcttaccac tttgggcatt    3420
cagctctcac cgtataacct cagcactctg gaagacctga acaccagatg gaagcttctg    3480
caggtggccg tcgaggaccg agtcaggcag ctgcatgaag cccacaggga ctttggtcca    3540
gcatctcagc actttctttc cacgtctgtc cagggtccct gggagagagc catctcgcca    3600
aacaaagtgc cctactatat caaccacgag actcaaacaa cttgctggga ccatcccaaa    3660
atgacagagc tctaccagtc tttagctgac ctgaataatg tcagattctc agcttatagg    3720
actgccatga aactccgaag actgcagaag gccctttgct ggatctcttg agcctgtca    3780 gctgcatgtg atgccttgga ccagcacaac ctcaagcaaa atgaccagcc catggatatc    3840
ctgcagatta ttaattgttt gaccactatt tatgaccgcc tggagcaaga gcacaacaat    3900
ttggtcaacg tccctctctg cgtggatatg tgtctgaact ggctgctgaa tgtttatgat    3960
acgggacgaa cagggaggat ccgtgtcctg tcttttaaaa ctggcatcat ttccctgtgt    4020
aaagcacatt tggaagacaa gtacagatac cttttcaagc aagtggcaag ttcaacagga    4080
ttttgtgacc agcgcaggct gggcctcctt ctgcatgatt ctatccaaat tccaagacag    4140
ttgggtgaag ttgcatcctt tggggggcagt aacattgagc caagtgtccg gagctgcttc    4200
caatttgcta ataataagcc agagatcgaa gcggccctct tcctagactg gatgagactg    4260
gaaccccagt ccatggtgtg gctgcccgtc ctgcacagag tggctgctgc agaaactgcc    4320
aagcatcagg ccaaatgtaa catctgcaaa gagtgtccaa tcattggatt caggtacagg    4380
agtctaaagc actttaatta tgacatctgc aaagctgct ttttttctgg tcgagttgca    4440
aaaggccata aaatgcacta tcccatggtg gaatattgca ctccgactac atcaggagaa    4500
gatgttcgag actttgccaa ggtactaaaa aacaaatttc gaaccaaaag gtattttgcg    4560
aagcatcccc gaatgggcta cctgccagtg cagactgtct tagagggga caacatggaa    4620 actcccgaca caatgtagtc gagaggccta ataaagagct cagatgcatc gatcagagtg    4680
tgttggtttt ttgtgtgaga tctaggaacc cctagtgatg gagttggcca ctccctctct    4740
gcgcgctcgc tcgctcactg aggccgcccg ggcaaagccc gggcgtcggg cgacctttgg    4800
tcgcccggcc tcagtgagcg agcgagcgcg cagagaggga gtggccaa                 4848
```

<210> SEQ ID NO 36
<211> LENGTH: 5060
<212> TYPE: DNA

<213> ORGANISM: Homo sapiens

<400> SEQUENCE: 36

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctagatc tgaattcggt accactacgg gtctaggctg     180
cccatgtaag gaggcaaggc ctgggacac  ccgagatgcc tggttataat taacccagac     240
atgtggctgc cccccccccc ccaacacctg ctgcctgagc ctcaccccca ccccggtgcc     300
tgggtcttag gctctgtaca ccatggagga gaagctcgct ctaaaaataa ccctgtccct     360
ggtggatcgg tacccgttac ataacttacg gtaaatggcc cgcctggctg accgcccaac     420
gacccccgcc cattgacgtc aataatgacg tatgttccca tagtaacgcc aatagggact     480
ttccattgac gtcaatgggt ggagtattta cggtaaactg cccacttggc agtacatcaa     540
gtgtatcata tgccaagtac gccccctatt gacgtcaatg acggtaaatg gcccgcctgg     600
cattatgccc agtacatgac cttatgggac tttcctactt ggcagtacat ctacgtatta     660
gtcatcgcta ttaccatggt gatgcggttt tggcagtaca tcaatgggcg tggatagcgg     720
tttgactcac ggggatttcc aagtctccac cccattgacg tcaatgggag tttgttttgg     780
caccaaaatc aacgggactt tccaaaatgt cgtaacaact ccgccccatt gacgcaaatg     840
ggcggtaggc gtgtacggtg ggaggtctat ataagcagag ctcgtttagt gaaccgtcag     900
atcgcctgga gacgccatcc acgctgtttt gacctccata gaagacaccg ggaccgatcc     960
agcctccgga ctctagagga tccggtactc gaattttcac catggtttgg tgggaagaag    1020
tagaggactg ttatgaaaga gaagatgttc aaaagaaaac attcacaaaa tgggtaaatg    1080
cacaattttc taagtttggg aagcagcata ttgagaacct cttcagtgac ctacaggatg    1140
ggaggcgcct cctagacctc ctcgaaggcc tgacagggca aaaactgcca aaagaaaaag    1200
gatccacaag agttcatgcc ctgaacaatg tcaacaaggc actgcgggtt ttgcagaaca    1260
ataatgttga tttagtgaat attgaagta ctgacatcgt agatgaaat cataaactga    1320
ctcttggttt gatttggaat ataatcctcc actggcaggt caaaaatgta atgaaaaata    1380
tcatggctgg attgcaacaa accaacagtg aaaagattct cctgagctgg gtccgacaat    1440
caactcgtaa ttatccacag gttaatgtaa tcaacttcac caccagctgg tctgatggcc    1500
tggctttgaa tgctctcatc catagtcata ggccagacct atttgactgg aatagtgtgg    1560
tttgccagca gtcagccaca caacgactgg aacatgcatt caacatcgcc agatatcaat    1620
taggcataga gaaactactc gatcctgaag atgttgatac cacctatcca gataagaagt    1680
ccatcttaat gtacatcaca tcactcttcc aagttttgcc tcaacaagtg agcattgaag    1740
ccatccagga agtggaaatg ttgccaaggc cacctaaagt gactaaagaa gaacattttc    1800
agttacatca tcaaatgcac tattctcaac agatcacggt cagtctagca cagggatatg    1860
agagaacttc ttcccctaag cctcgattca gagctatgc ctacacacag gctgcttatg    1920
tcaccaccct tgaccctaca cggagcccat tccttcaca gcatttggaa gctcctgaag    1980
acaagtcatt tggcagttca ttgatggaga gtgaagtaaa cctggaccgt tatcaaacag    2040
ctttagaaga agtattatcg tggcttcttt ctgctgagga cacattgcaa gcacaaggag    2100
agatttctaa tgatgtggaa gtggtgaaag accagtttca tactcatgag gggtacatga    2160
tggatttgac agcccatcag gccgggttg gtaatattct acaattggga agtaagctga    2220
ttggaacagg aaaattatca gaagatgaag aaactgaagt acaagagcag atgaatctcc    2280
```

```
taaattcaag atgggaatgc ctcagggtag ctagcatgga aaaacaaagc aatttacata    2340 gagtttaat ggatctccag aatcagaaac tgaaagagtt gaatgactgg ctaacaaaaa    2400
cagaagaaag aacaaggaaa atggaggaag agcctcttgg acctgatctt gaagacctaa    2460
aacgccaagt acaacaacat aaggtgcttc aagaagatct agaacaagaa caagtcaggg    2520
tcaattctct cactcacatg gtggtggtag ttgatgaatc tagtggagat cacgcaactg    2580
ctgctttgga agaacaactt aaggtattgg gagatcgatg ggcaaacatc tgtagatgga    2640
cagaagaccg ctgggttctt ttacaagaca ctcatagatt actgcaacag ttcccctgg     2700 acctggaaaa gtttcttgcc tggcttacag aagctgaaac aactgccaat gtcctacagg    2760
atgctacccg taaggaaagg ctcctagaag actccaaggg agtaaaagag ctgatgaaac    2820
aatggcaaga cctccaaggt gaaattgaag ctcacacaga tgtttatcac aacctggatg    2880
aaaacagcca aaaaatcctg agatccctgg aaggttccga tgatgcagtc ctgttacaaa    2940
gacgtttgga taacatgaac ttcaagtgga gtgaacttcg gaaaaagtct ctcaacatta    3000
ggtcccattt ggaagccagt tctgaccagt ggaagcgtct gcacctttct ctgcaggaac    3060
ttctggtgtg gctacagctg aaagatgatg aattaagccg gcaggcacct attggaggcg    3120
actttccagc agttcagaag cagaacgatg tacatagggc cttcaagagg gaattgaaaa    3180
ctaaagaacc tgtaatcatg agtactcttg agactgtacg aatatttctg acagagcagc    3240 cttggaagg actagagaaa ctctaccagg agcccagaga gctgcctcct gaggagagag    3300
cccagaatgt cactcggctt ctacgaaagc aggctgagga ggtcaatact gagtgggaaa    3360
aattgaacct gcactccgct gactggcaga gaaaaataga tgagacccct gaaagactcc    3420
aggaacttca agaggccacg gatgagctgg acctcaagct gcgccaagct gaggtgatca    3480
agggatcctg gcagcccgtg ggcgatctcc tcattgactc tctccaagat cacctcgaga    3540
aagtcaaggc acttcgagga gaaattgcgc ctctgaaaga gaacgtgagc cacgtcaatg    3600
accttgctcg ccagcttacc actttgggca ttcagctctc accgtataac ctcagcactc    3660
tggaagacct gaacaccaga tggaagcttc tgcaggtggc cgtcgaggac cgagtcaggc    3720
agctgcatga agcccacagg gactttggtc cagcatctca gcactttctt ccacgtctg    3780 tccagggtcc ctgggagaga gccatctcgc aaacaaagt gccctactat atcaaccacg    3840
agactcaaac aacttgctgg gaccatccca aaatgacaga gctctaccag tctttagctg    3900
acctgaataa tgtcagattc tcagcttata ggactgccat gaaactccga agactgcaga    3960 aggcccttg cttggatctc ttgagcctgt cagctgcatg tgatgccttg accagcaca    4020 acctcaagca aaatgaccag cccatggata tcctgcagat tattaattgt ttgaccacta    4080
tttatgaccg cctggagcaa gagcacaaca atttggtcaa cgtccctctc tgcgtggata    4140
tgtgtctgaa ctggctgctg aatgtttatg atacgggacg aacagggagg atccgtgtcc    4200
tgtcttttaa aactggcatc atttccctgt gtaaagcaca tttggaagac aagtacagat    4260
accttttcaa gcaagtggca agttcaacag gattttgtga ccagcgcagg ctgggcctcc    4320
ttctgcatga ttctatccaa attccaagac agttgggtga agttgcatcc tttgggggca    4380
gtaacattga gccaagtgtc cggagctgct tccaatttgc taataataag ccagagatcg    4440
aagcggccct cttcctagac tggatgagac tggaacccca gtccatggtg tggctgcccg    4500
tcctgcacag agtggctgct gcagaaactg ccaagcatca ggccaaatgt aacatctgca    4560
aagagtgtcc aatcattgga ttcaggtaca ggagtctaaa gcactttaat tatgacatct    4620
```

```
                                    -continued
gccaaagctg ctttttttct ggtcgagttg caaaaggcca taaaatgcac tatcccatgg    4680
tggaatattg cactccgact acatcaggag aagatgttcg agactttgcc aaggtactaa    4740
aaaacaaatt tcgaaccaaa aggtattttg cgaagcatcc ccgaatgggc tacctgccag    4800
tgcagactgt cttagagggg gacaacatgg aaactcccga cacaatgtag tcgagaggcc    4860
taataaagag ctcagatgca tcgatcagag tgtgttggtt ttttgtgtga gatctaggaa    4920
cccctagtga tggagttggc cactccctct ctgcgcgctc gctcgctcac tgaggccgcc    4980
cgggcaaagc ccgggcgtcg ggcgaccttt ggtcgcccgg cctcagtgag cgagcgagcg    5040
cgcagagagg gagtggccaa                                                5060
```